US010577371B2

(12) United States Patent
Lu et al.

(10) Patent No.: US 10,577,371 B2
(45) Date of Patent: Mar. 3, 2020

(54) SMALL MOLECULE HISTONE METHYLTRANSFERASE SUV39H1 INHIBITOR AND USES THEREOF

(71) Applicants: Augusta University Research Institute, Inc., Augusta, GA (US); Department of Veterans Affairs, Washington, DC (US)

(72) Inventors: Chunwan Lu, Augusta, GA (US); Iryna Lebedyeva, Augusta, GA (US); Kebin Liu, Augusta, GA (US)

(73) Assignees: Augusta University Research Institute, Inc., Augusta, GA (US); Department of Veterans Affairs, Washington, DC (US)

( * ) Notice: Subject to any disclaimer, the term of this patent is extended or adjusted under 35 U.S.C. 154(b) by 0 days.

(21) Appl. No.: 16/134,306

(22) Filed: Sep. 18, 2018

(65) Prior Publication Data
US 2019/0084987 A1    Mar. 21, 2019

Related U.S. Application Data

(60) Provisional application No. 62/559,747, filed on Sep. 18, 2017, provisional application No. 62/649,285, filed on Mar. 28, 2018.

(51) Int. Cl.
| C07D 487/04 | (2006.01) |
| A61K 45/06 | (2006.01) |
| A61P 35/00 | (2006.01) |
| A61K 39/395 | (2006.01) |
| A61K 31/407 | (2006.01) |
| C07K 16/28 | (2006.01) |
| A61K 39/00 | (2006.01) |

(52) U.S. Cl.
CPC .......... *C07D 487/04* (2013.01); *A61K 31/407* (2013.01); *A61K 39/3955* (2013.01); *A61K 45/06* (2013.01); *A61P 35/00* (2018.01); *C07K 16/2818* (2013.01); *A61K 2039/505* (2013.01); *C07K 2317/76* (2013.01)

(58) Field of Classification Search
None
See application file for complete search history.

(56) References Cited

U.S. PATENT DOCUMENTS

2015/0148292 A1*  5/2015  Boden ............... A61L 27/46
                                                                        514/8.8

OTHER PUBLICATIONS

Afshar-Sterle, Shoukat et al., "Fas Ligand-Mediated Immune Surveillance by T Cells is Essential for the Control of Spontaneous B Cell Lymphomas", Nat Med, 20(3):283-290 (2014).

Allan, R.S, et al., "An Epigenetic Silencing Pathway Controlling T Helper 2 Cell Lineage Commitment", Nature, 487:249-253 (2012). (Abstract Only).
Camus, Matthieu et al., "Coordination of Intratumoral Immune Reaction and Human Colorectal Cancer Recurrence", Cancer Res, 69(6):2685-2693 (2009).
Carter, Paul et al., "Studies on the Synthesis of the Antitumor Agent CC-1065. Synthesis of PDE I and PDE II, Inhibitors of Cyclic Adenosine-3',5'-Monophosphate Phosphodiesterase Using the 3,3'-Bipyrrole Strategy", J Am Chem Soc, 109:2711-2717 (1987).
Feng, Zijie et al., "Menin and Daxx Interact to Suppress Neuroendocrine Tumors through Epigenetic Control of the Membrane Metallo-Endopeptidase", Cancer Res, 77(2):401-411 (2017).
Fodor, Barna D. et al., "Mammalian Su(var) Genes in Chromatin Control", Annu Rev Cell Dev Biol, 26:471-501 (2010).
Fridman, Wolf Herman, et al., "Prognostic and Predictive Impact of Intra—and Peritumoral Immune Infiltrates", Cancer Res, 71(17):5601-5605 (2011).
Gabrilovich, Dmitry I. et al., "Coordinated Regulation of Myeloid Cells by Tumours", Nat Rev Immunol, 12(4):253-268 (2012).
Galon, J. et al., "Type, Density, and Location of Immune Cells Within Human Colorectal Tumors Predict Clinical Outcome", Science, 313:1960-1964 (2006). (Abstract Only).
Galon, Jerome et al., "The Adaptive Immunologic Microenvironment in Colorectal Cancer: A Novel Perspective", Cancer Res, 67(5):1883-1886 (2007).
Greiner, D. et al., "Identification of a Specific Inhibitor of the Histone Methyltransferase SU(VAR)3-9", Nat Chem Biol, 1:143-145 (2005). (Abstract Only).
Guinney, Justin et al., "The Consensus Molecular Subtypes of Colorectal Cancer", Nat Med, 21(11):1350-1356 (2015).
Hanahan, D. et al., "Hallmarks of Cancer: The Next Generation", Cell, 144:646-674 (2011). (Abstract Only).
Holmgaard, Rikke B. et al., "Timing of CSF-1/CSF-1R Signaling Blockade is Critical to Improving Responses to CTLA-4 Based Immunotherapy", Oncoimmunology, 5(7):e1151595 (2016).
Juneja, Vikram R. et al., "PD-L1 on Tumor Cells is Sufficient for Immune Evasion in Immunogenic Tumors and Inhibits CD8 T Cell Cytotoxicity", J Exp Med, 214(4):895-904 (2017).
Kagi, D. et al., "Fas and Perforin Pathways as Major Mechanisms of T Cell-Mediated Cytotoxicity", Science, 265:528-530 (1994). (Abstract Only).
Kroemer, Guido et al., "Colorectal Cancer: The First Neoplasia Found to be Under Immunosurveillance and the Last one to Respond to Immunotherapy?", Oncoimmunology, 4:e1058597 (2015).
Le, Dung T. et al., "PD-1 Blockade in Tumors with Mismatch-Repair Deficiency", N Engl J Med, 372:2509-2520 (2015).
Le, Dung T. et al., "A Blueprint to Advance Colorectal Cancer Immunotherapies", Cancer Immunol Res, 5(11):942-949 (2017).
Llosa, Nicolas J. et al., "The Vigorous Immune Microenvironment of Microsatellite Instable Colon Cancer is Balanced by Multiple Counter-Inhibitory Checkpoints" Cancer Discov, 5(1):43-51 (2015).

(Continued)

Primary Examiner — Alicia L Otton
(74) Attorney, Agent, or Firm — Smith, Gambrell & Russell, LLP

(57) ABSTRACT

Compositions for the inhibition of SUV39H1 methyltransferase activity and methods of use thereof are provided. The disclosed compositions may be used for treating certain types of cancer, inducing apoptosis in a cancer cell, increasing cell sensitivity to FasL-induced apoptosis, and overcoming cancer cell resistance to apoptosis and/or certain types of cancer immunotherapy.

18 Claims, 33 Drawing Sheets

(56) References Cited

OTHER PUBLICATIONS

Marisa, L. et al., "The Balance Between Cytotoxic T-Cell Lymphocytes and Immune Checkpoint Expression in the Prognosis of Colon Tumors", J Natl Cancer Inst, 110(1) (2018). (Abstract Only).
Masugi, Yohei et al., "Tumour CD274 (PD-L1) Expression and T Cells in Colorectal Cancer", Gut, 66:1463-1473 (2017).
Mlecnik, B. et al., "Comprehensive Intrametastatic Immune Quantification and Major Impact of Immunoscore on Survival", J Natl Cancer Inst, 110(1) (2018). (Abstract Only).
Moller, Peter et al., "Expression of APO-1 (CD95), A Member of the NGF/TNF Receptor Superfamily, in Normal and Neoplastic Colon Epithelium", Int J Cancer, 51:371-377 (1994).
Muller, Manuel M. et al., "A Two-State Activation Mechanism Controls the Histone Methyltransferase Suv39h1", Nat Chem Biol, 12:188-193 (2016).
Nizialek, Emily A. et al., "Cancer-Predisposition Gene KLLN Maintains Pericentric H3K9 Trimethylation Protecting Genomic Stability", Nucleic Acids Res, 44(8):3586-3594 (2016).
Olcina, M.M. et al., "H3K9me3 Facilitates Hypoxia-Induced p53-Dependent Apoptosis Through Repression of APAK", Oncogene, 35:793-799 (2016).
O'Reilly, Lorraine A. et al., "Membrane-Bound But Not Secreted Fas Ligand is Essential for Fas-Induced Apoptosis and Prevention of Autoimmunity and Cancer", Nature, 461:659-663 (2009).
Pace, Luigia et al., "The Epigenetic Control of Sternness in CD8(+) T Cell Fate Commitment", Science, 359:177-186 (2018).
Pages, Franck M.D. et al., "Effector Memory T Cells, Early Metastasis, and Survival in Colorectal Cancer", N Engl J Med, 353:2654-2666 (2005).
Paschall, Amy V. et al., "H3K9 Trimethylation Silences Fas Expression to Confer Colon Carcinoma Immune Escape and 5-Fluorouracil Chemoresistance", J Immunol, 195(4); 1868-1882 (2015).
Quintana, Francisco J. et al., "Aiolos Promotes TH17 Differentiation by Directly Silencing Il2 Expression", Nat Immunol, 13(8):770-777 (2012).
Rea, Stephen et al., "Regulation of Chromatin Structure by Site-Specific Histone H3 Methyltransferases", Nature, 406:593-599 (2000).
Rice, Judd C. et al., "Histone Methyltransferases Direct Different Degrees of Mmethylation to Define Distinct Chromatin Domains", Mol Cell, 12:1591-1598 (2003).
Ries, Carola H. et al., "Targeting Tumor-Associated Macrophages with Anti-CSF-1R Antibody Reveals a Strategy for Cancer Therapy", Cancer Cell, 25:846-859 (2014).
Russ, Brendan E. et al., "Distinct Epigenetic Signatures Delineate Transcriptional Programs During Virus-Specific CD8(+) T Cell Differentiation", Immunity, 41:853-865 (2014). (Abstract Only).
Russell, John H. et al., "Lymphocyte-Mediated Cytotoxicity", Annu Rev Immunol, 20:323-370 (2002).
Shankaran, Vijay et al., IFNgamma and Lymphocytes Prevent Primary Tumour Development and Shape Tumour Immunogenicity, Nature, 410:1107-1111 (2001).
Strater, J. et al., "In Situ Detection of Enterocytic Apoptosis in Normal Colonic Mucosa and in Familial Adenomatous Polyposis", Gut, 37:819-825 (1995).
Strater, Jorn et al., "CD95 (APO-1/Fas)-Mediated Apoptosis in Colon Epithelial Cells: A Possible Role in Ulcerative Colitis", Gastroenterology, 113:160-167 (1997).
Strater, J. et al., "Impaired CD95 Expression Predisposes for Recurrence in Curatively Resected Colon Carcinoma: Clinical Evidence for Immunoselection and CD95L Mediated Control of Minimal Residual Disease", Gut, 54:661-665 (2005).
Suryo Rahmanto, Yohan et al., "Inactivating ARID1A Tumor Suppressor Enhances TERT Transcription and Maintains Telomere Length in Cancer Cells", J Biol Chem, 291(18):9690-9699 (2016).
Tosolini, Marie et al., "Clinical Impact of Different Classes of Infiltrating T Cytotoxic and Helper Cells (Th1, Th2, Treg, Th17) in Patients with Colorectal Cancer", Cancer Res, 71:1263-1271 (2011).
Trott Oleg et al., "AutoDock Vina: Improving the Speed and Accuracy of Docking with a New Scoring Function, Efficient Optimization, and Multithreading", J Comput Chem, 31:455-461 (2010).
Von Reyher, Ulrike et al., "Colon Carcinoma Cells Use Different Mechanisms to Escape CD95-Mediated Apoptosis", Cancer Res, 58:526-534 (1998).
Wang, Tao et al., "Crystal Structure of the Human SUV39H1 Chromodomain and Its Recognition of Histone H3K9me2/3", PLOS One, 7(12):e52977 (2012).

* cited by examiner

C26H17ClN2O8S   MW:552.95

C27H19FN2O8S    MW:550.51

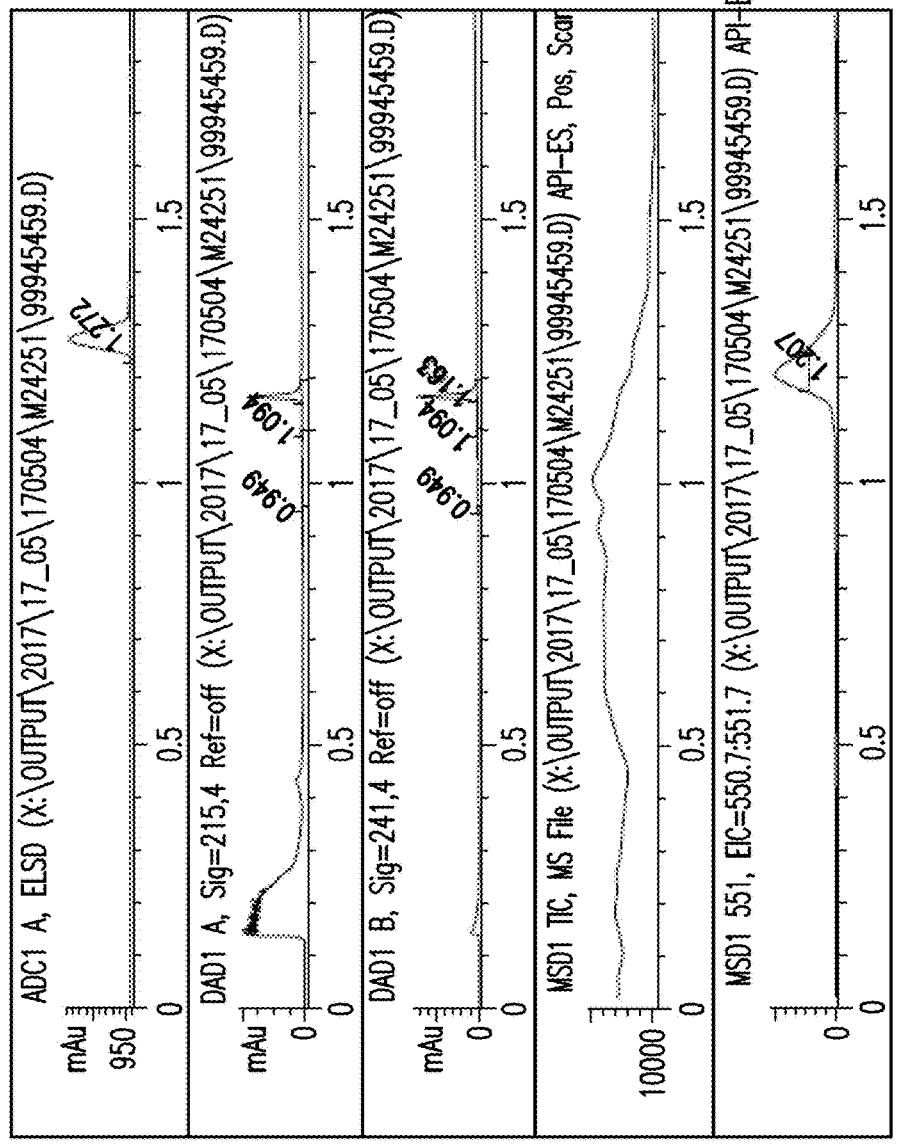
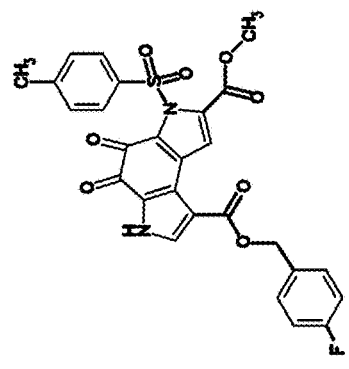
FIG. 4C

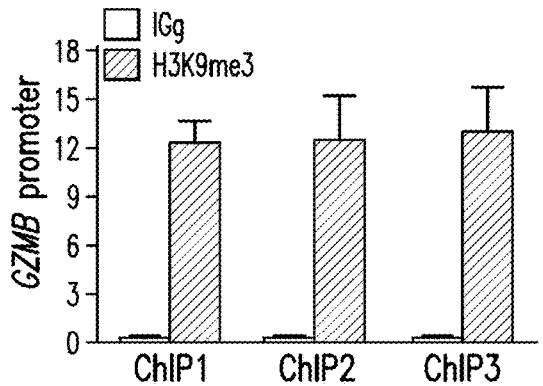
FIG. 9A
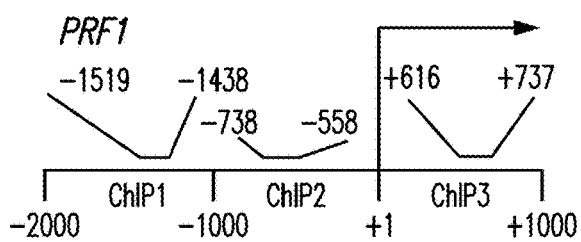
FIG. 9B
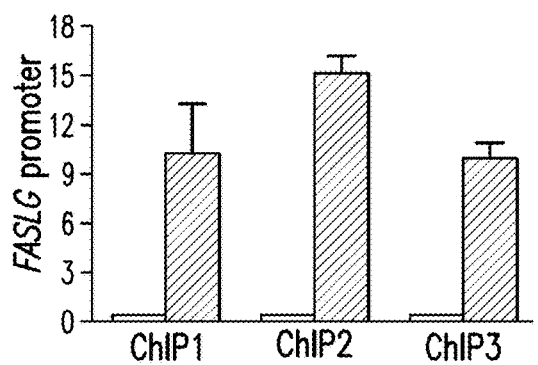
FIG. 9C
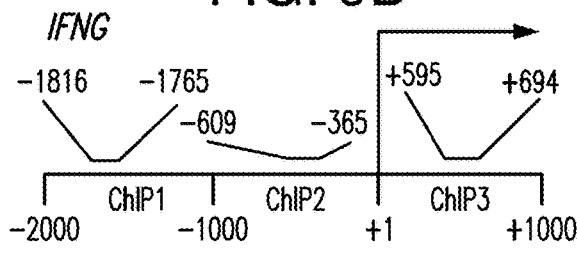
FIG. 9D
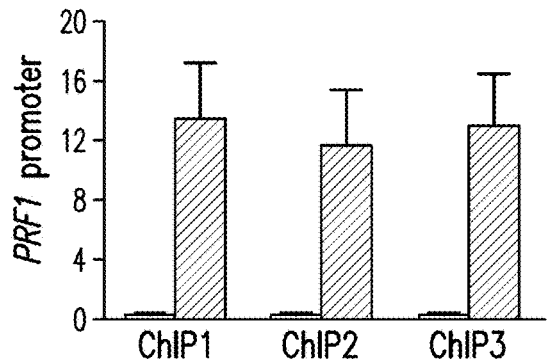
FIG. 9E
FIG. 9F
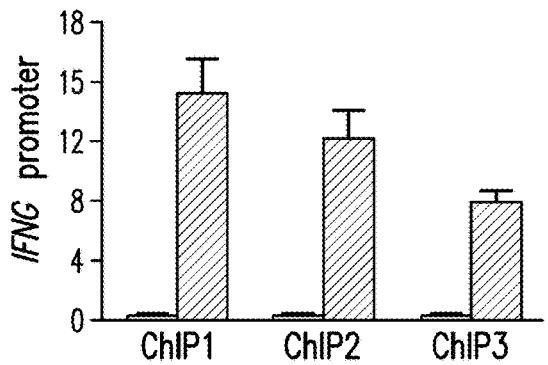
FIG. 9G
FIG. 9H

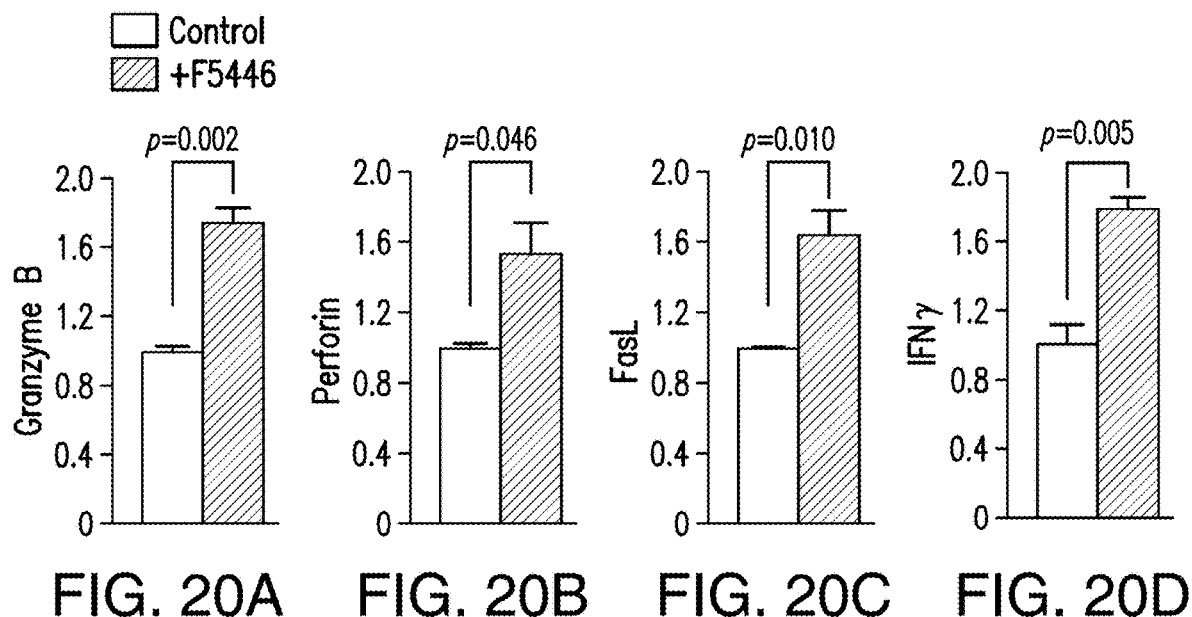
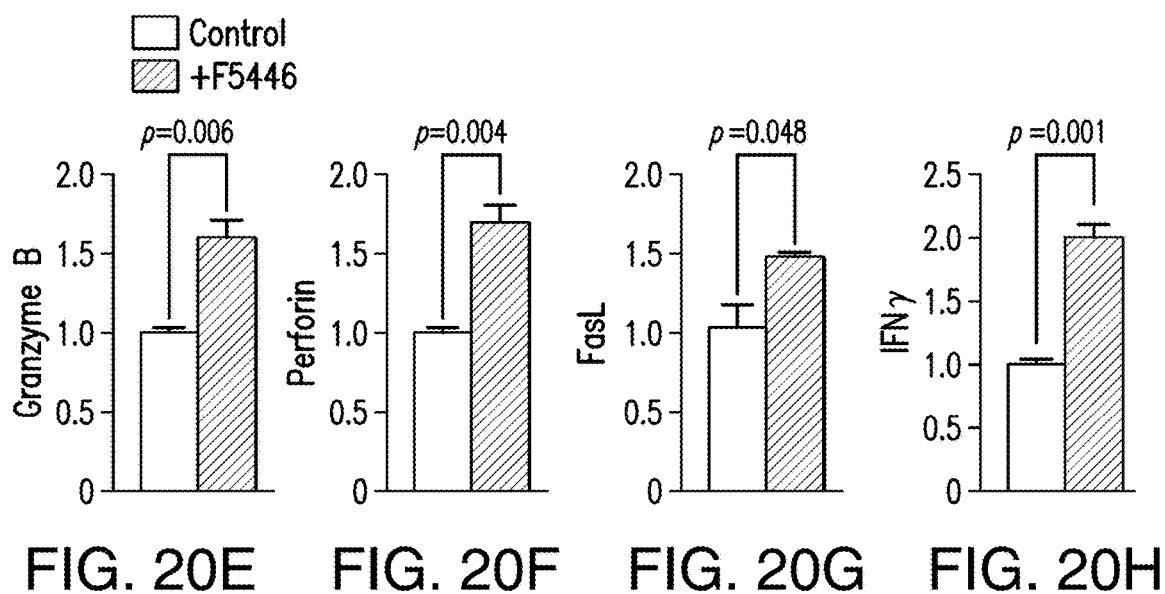

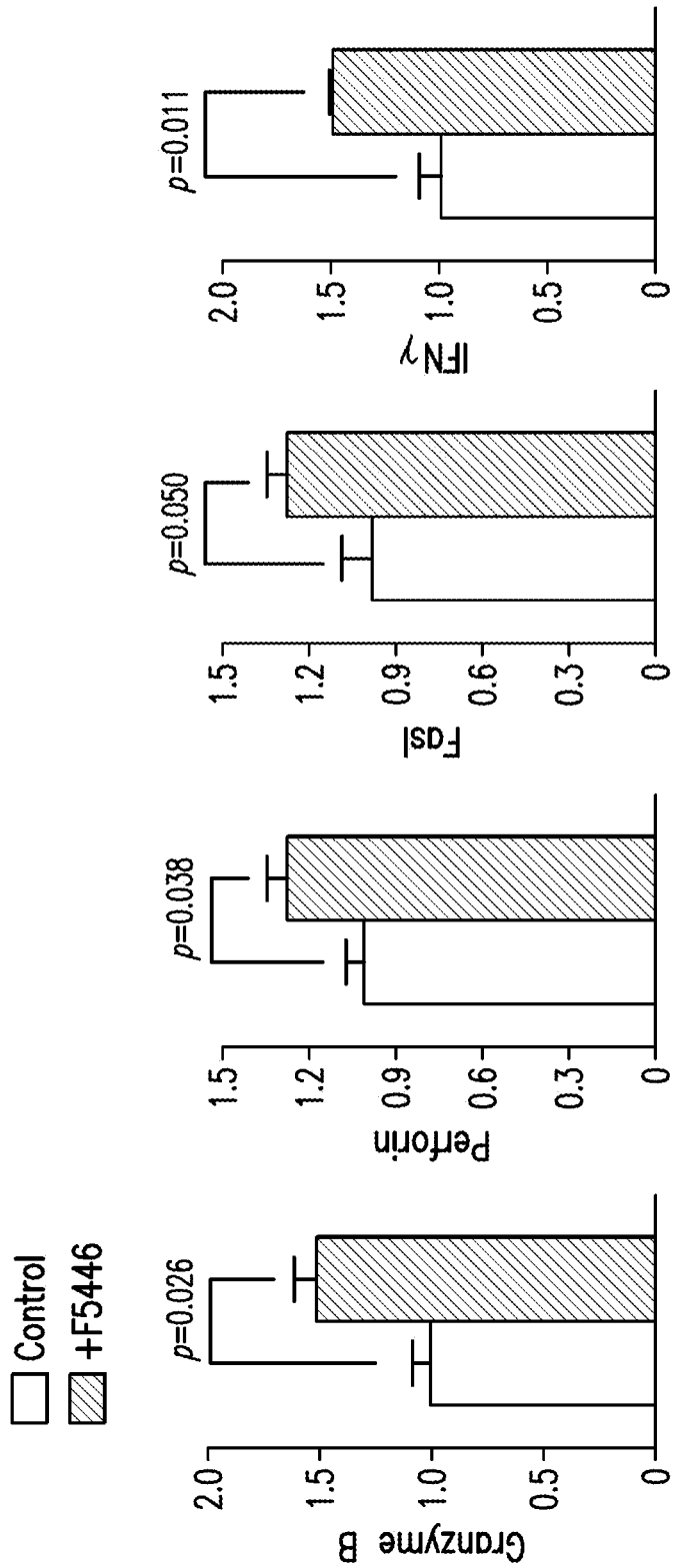

SMALL MOLECULE HISTONE METHYLTRANSFERASE SUV39H1 INHIBITOR AND USES THEREOF

CROSS-REFERENCE TO RELATED APPLICATIONS

This application claims benefit of and priority to U.S. Provisional Patent Application 62/559,747 filed on Sep. 18, 2017 and U.S. Provisional Patent Application 62/649,285 filed on Mar. 28, 2018, and where permitted all of which are incorporated in their entireties.

STATEMENT REGARDING FEDERALLY SPONSORED RESEARCH

This invention was made with government support under CA182518 awarded by the National Institutes of Health and under BX001962 awarded by the Department of Veterans Affairs. The government has certain rights in the invention.

FIELD OF THE INVENTION

The invention is generally directed to compositions for the inhibition of SUV39H1 methyltransferase activity, and methods of use thereof.

BACKGROUND OF THE INVENTION

Cancer is one of the leading causes of morbidity and mortality worldwide. Most types of cancer do not have a cure. Cancer immunotherapy, such as T cell-based immune checkpoint blockade immunotherapy, has recently emerged as an effective treatment that can result in durable efficacy in many types of human cancer. However, not all patients and types of cancer respond to immunotherapy. For instance, human colorectal cancer, except for microsatellite instability (MSI) colorectal cancer which accounts for less than 4% of human colon cancer, and pancreatic cancer do not respond to anti-PD-L1/PD-1 mAb immunotherapy.

While developing cancer therapies, researchers have focused on covalent modifications of DNA and histones, the two core components of eukaryotic chromatin, as the two major mechanisms of epigenetic regulation of gene expression. The methylation of lysine residues in histones, particularly in the N-terminal tails of histones H3 and H4 of the chromatin, play a fundamental role in the regulation of gene expression through modulating chromatin structure. Histone methyltransferase ("HMTase") catalyzes the methylation of histones to modify chromatin structure, thereby influencing gene expression patterns during cellular processes. Recent studies have established a fundamental role of HMTase activity in developing treatment for human diseases, particularly human cancers. Unlike genetic mutations of oncogenes and tumor suppressor genes, which are permanent alterations in the cancer genome, histone methylation is a reversible process, which has made HMTases attractive molecular targets for cancer therapy.

DNA methylation and histone acetylation have been extensively studied and efforts have been devoted to develop DNA methylation inhibitors (for example, Decitabine) and histone acetylase inhibitors (for example, SAHA). Due to the complex nature of their mechanism of action, HMTases are often an ignored area and development of HMTase inhibitors are still in its infancy. For instance, chaetocin and verticillin A are the only two SUV39H1 inhibitors. SUV39H1 is an HMTase that catalyzes H3K9 trimethylation ("H3K9me3"), which is a hallmark of a transcriptionally repressive chromatin structure. H3K9me3 is well-known to be a silencer of tumor suppressors. However, both chaetocin and verticillin A have multiple targets and are toxic in vivo.

Therefore, it is an object of the invention to provide small molecule HMTase inhibitors and methods of their use.

It is another object of the invention to provide compositions and methods for treating hyperproliferative conditions or a symptom thereof.

It is another object of the invention to provide compositions and methods for killing cancer cells in a subject in need thereof.

SUMMARY OF THE INVENTION

SUV39H1-inhibiting compounds are provided that are useful for, for example, activating cytotoxic T cell effectors including perforin, granzyme, FasL and IFNgamma in tumor-infiltrating T cells. Activating these T cell effectors reverse tumor-induced immune suppression to promote T cells to kill tumor cells to suppress tumor development. Additionally, these compounds can be used to treat certain types of cancer, induce apoptosis in a cancer cell of a patient, reduce cancer cell resistance to apoptosis, resistance to drug therapies, and/or resistance to certain types of immunotherapy, and increase cancer or tumor cell sensitivity to T cell-induced apoptosis.

One embodiment provides SUV39H1-inhibiting compounds defined according to formula (I) as follows:

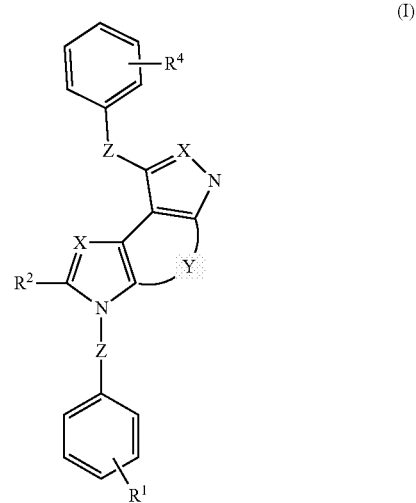

wherein:

$R^1$ and $R^4$ are each independently selected from —H, halogen, —$NO_2$, —$CH_3$, —O-alkyl, —N-alkyl, —S-alkyl, —$NH_2$, —COO—($C_1$-$C_{16}$)-alkyl, or —$CONR^5R^6$, $R^2$ is selected from —H, halogen, —O-alkyl, —N-alkyl, —S-alkyl, —($C_1$-$C_{33}$)-alkyl, -heteroaryl, -aryl, -acyl, or —COO—($C_1$-$C_{16}$)-alkyl, X is —CH or —N, Z is selected from —$SO_2$, —SO, —($C_1$-$C_{33}$) alkyl, —($C_1$-$C_{33}$) alkenyl, —CO(($CH_2$)$_n$), —O, —$SOCH_3$, —NS, or —S—S, Y is selected from —C=O—C=O, —($C_1$-$C_4$)-alkyl, —CH=CH—, —N, —O, —S, —$CH_2R^7CH_2$, —CNC, —CN, or —NC, $R^5$ and $R^6$ are each independently selected from —H, —($C_1$-$C_4$)-alkyl, —($C_1$-$C_3$)-alkoxy-($C_2$-$C_4$)-alkyl, or —OH—($C_2$-$C_4$)-alkyl, $R^7$ is —S, —O, or —N, and n is 1 to 33.

In certain embodiments of the compounds of formula (I), $R^1$ and $R^4$ are each independently selected from —H, —F, —Cl, —Br, —I, —$NO_2$, —$CH_3$, —O—($C_1$-$C_{20}$)-alkyl, —N—($C_1$-$C_{20}$)-alkyl, —S—($C_1$-$C_{20}$)-alkyl, —$NH_2$, —COO—($C_1$-$C_{16}$)-alkyl, or —CONR$^5$R$^6$, where $R^5$ and $R^6$ are each independently selected from —H, —($C_1$-$C_4$)-alkyl, —($C_1$-$C_3$)-alkoxy-($C_2$-$C_4$)-alkyl, or —OH—($C_2$-$C_4$)-alkyl; $R^2$ is selected from —H, —F, —Cl, —Br, —I, —O—($C_1$-$C_{20}$)-alkyl, —N—($C_1$-$C_{20}$)-alkyl, —S—($C_1$-$C_{20}$)-alkyl, —($C_1$-$C_{20}$)-alkyl, —($C_3$-$C_{20}$)-heteroaryl, —($C_6$-$C_{20}$)-aryl, acyl, or —COO—($C_1$-$C_{12}$)-alkyl; X is —CH or —N; Z is selected from —$SO_2$, —SO, —($C_1$-$C_{20}$) alkyl, —($C_1$-$C_{20}$) alkenyl, —CO(($CH_2$)$_n$), —O, —$SOCH_3$, —NS, or —SS, where n is 1 to 20; and Y is selected from —C=O—C=O, —($C_1$-$C_3$)-alkyl, —CH=CH—, —N, —O, —S, —$CH_2SCH_2$, —$CH_2OCH_2$, —$CH_2NCH_2$, —CNC, —CN, or —NC.

In other embodiments of the compounds of formula (I), $R^1$ and $R^4$ are each independently be selected from —H, —F, —Cl, —$NO_2$, —$CH_3$, —O—($C_1$-$C_{12}$)-alkyl, —N—($C_1$-$C_{12}$)-alkyl, —S—($C_1$-$C_{12}$)-alkyl, —$NH_2$, or —COO—($C_1$-$C_{12}$)-alkyl; $R^2$ is selected from —H, —F, —Cl, —Br, —I, —O—($C_1$-$C_{12}$)-alkyl, —N—($C_1$-$C_{12}$)-alkyl, —S—($C_1$-$C_{12}$)-alkyl, —($C_1$-$C_{12}$)-alkyl, —($C_3$-$C_{14}$)-heteroaryl, —($C_6$-$C_{14}$)-aryl, $R_y$—CO— where $R_y$ is a —($C_1$-$C_{12}$)-alkyl, —($C_3$-$C_6$)-cycloalkyl, or phenyl, or —COO—($C_1$-$C_4$)-alkyl; X is —CH or —N; Z is selected from —$SO_2$, —SO, —($C_1$-$C_{12}$) alkyl, —($C_1$-$C_{12}$) alkenyl, —CO(($CH_2$)$_n$), —O, or —$SOCH_3$, where n is 1 to 12; and Y is selected from —C=O—C=O, —($C_1$-$C_2$)-alkyl, or —CH=CH—.

In one embodiment, the disclosed SUV39H1-inhibiting compositions include the compound, 1-Benzyl 7-methyl 6-(4-chlorobenzenesulfonyl)-4,5-dioxo-3H,4H,5H,6H-pyrrolo[3,2-e]indole-1,7-dicarboxylate, having the following chemical structure:

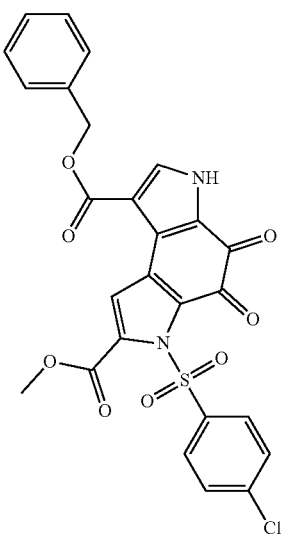 [SMILES: COC(=O)c1cc2c(n1S(=O)(=O)c1ccc(Cl)cc1)C(=O)C(=O)c1[nH]cc(C(=O)OCc3ccccc3)c1-2]

or an enantiomer, hydrate, pharmaceutically acceptable salt, stereoisomer, tautomer, or derivative thereof. Exemplary tautomers include, but are not limited to a keto-enol or lactam-lactim tautomer.

In another embodiment, the disclosed SUV39H1-inhibiting compositions include the compound, 1-(4-Fluorophenyl) methyl 7-methyl 6-(4-methylbenzenesulfonyl)-4,5-dioxo-3H,4H,5H,6H-pyrrolo[3,2-e]indole-1,7-dicarboxylate, having the following chemical structure:

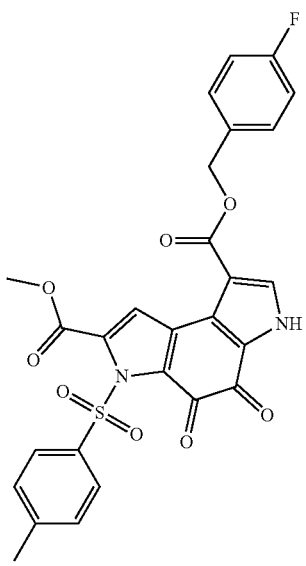 [SMILES: COC(=O)c1cc2c(n1S(=O)(=O)c1ccc(C)cc1)C(=O)C(=O)c1[nH]cc(C(=O)OCc3ccc(F)cc3)c1-2]

or an enantiomer, hydrate, pharmaceutically acceptable salt, or stereoisomer, or tautomer, or derivative thereof. Exemplary tautomers include, but are not limited to such a keto-enol or lactam-lactim tautomer One embodiment provides a pharmaceutical composition including the compound of formula (I), an enantiomer, hydrate, pharmaceutically acceptable salt, stereoisomer, tautomer, or derivative of the compound of formula (I), or any combination thereof, together with a pharmaceutically acceptable excipient. The compound(s) of formula (I) are present in the pharmaceutical composition in an amount effective to inhibit SUV39H1 methyltransferase activity in vivo or in vitro.

In certain embodiments, the pharmaceutical composition is formulated for parenteral administration, for example, intramuscular, intraperitoneal, intravitreal, intravenous, and subcutaneous administration. In other embodiments, the pharmaceutical composition is formulated for enteral administration. In still another embodiment, the pharmaceutical composition is formulated as an extended release formulation.

Another embodiment provides a method of treating cancer, for example, colorectal cancer or pancreatic cancer, by administering to a subject with cancer an effective amount of the SUV39H1-inhibiting compounds disclosed herein.

Still another embodiment provides a method of inducing apoptosis in a cancer cell of a subject by administering to a subject in need thereof an effective amount of the SUV39H1-inhibiting compounds disclosed herein.

Another embodiment provides a method for increasing FasL-induced apoptosis of cancer cells, for example, colorectal or pancreatic cancer cells, in a subject by administering to a subject in need thereof an effective amount of the SUV39H1-inhibiting compounds disclosed herein to increase cancer cell sensitivity to FasL-induced apoptosis. In one embodiment, the SUV39H1-inhibiting compounds are administered in an amount effective to increase expression of Fas receptor on tumor or cancer cells.

Yet another embodiment provides a method for increasing colorectal or pancreatic cancer cell sensitivity to cancer immunotherapy, for example, anti-PD-1/PD-L1 immunotherapy, by administering to a subject in need thereof an effective amount of the SUV39H1-inhibiting compounds disclosed herein to increase cancer cell sensitivity to apoptosis.

One embodiment provides a method for treating cancer in a subject in need thereof by administering a checkpoint inhibitor therapy in combination or alternation with an effective amount of one or more compounds according to formula I.

Another embodiment provides a pharmaceutical composition containing a checkpoint inhibitor and a compound according to formula I and a pharmaceutically acceptable excipient.

Another embodiment provides a method for treating cancer in a subject in need thereof by administering to the subject a pharmaceutical composition including one or more compounds according to Formulas I wherein the subject is non-responsive to cancer immunotherapy, for example where the subject is non-responsive to checkpoint inhibitor therapies.

Another embodiment provides a method for increasing T cell killing of tumor or cancer cells in a subject in need thereof by administering to the subject an effective amount of a pharmaceutical composition including one or more compounds according to formula I to increase Fas expression in the tumor or cancer cell.

One embodiment provides a method of reducing tumor burden in a subject in need thereof by administering to the subject an effective amount of a pharmaceutical composition including one or more compounds according to formula I to induce, promote, or enhance T cell mediated killing of tumor cells in the subject.

BRIEF DESCRIPTION OF THE DRAWINGS

Further features and advantages of the invention can be ascertained from the following detailed description that is provided in connection with the drawings described below:

FIG. 9 shows H3K9me3 expression levels in four promoter regions (GZMB, FIG. 9B; FASLG, FIG. 9D; PRF1, FIG. 9F; and IFNG, FIG. 9H) in resting mouse CD3+ T cells. The promoter structures of each gene and the ChIP PCR primers are indicated for GZMB (FIG. 9A), FASLG (FIG. 9C), PRF1 (FIG. 9E), and IFNG (FIG. 9G).

FIGS. 20A-20D are bar graphs that show expression levels of granzymeB (FIG. 20A), perforin (FIG. 20B), FasL (FIG. 20C) and IFNγ(FIG. 20D) in control mice (white bar) and $C_{57}$/BL6 mice treated with compound 1 (hatched bar). FIGS. 20E-20H are bar graphs that show expression levels of granzymeB (FIG. 20E), perforin (FIG. 20F), FasL (FIG. 20G) and IFNγ(FIG. 20H) in control mice (white bar) and BALB/C mice treated with compound 1 (hatched bar).

DETAILED DESCRIPTION

I. Definitions

Figure 1:
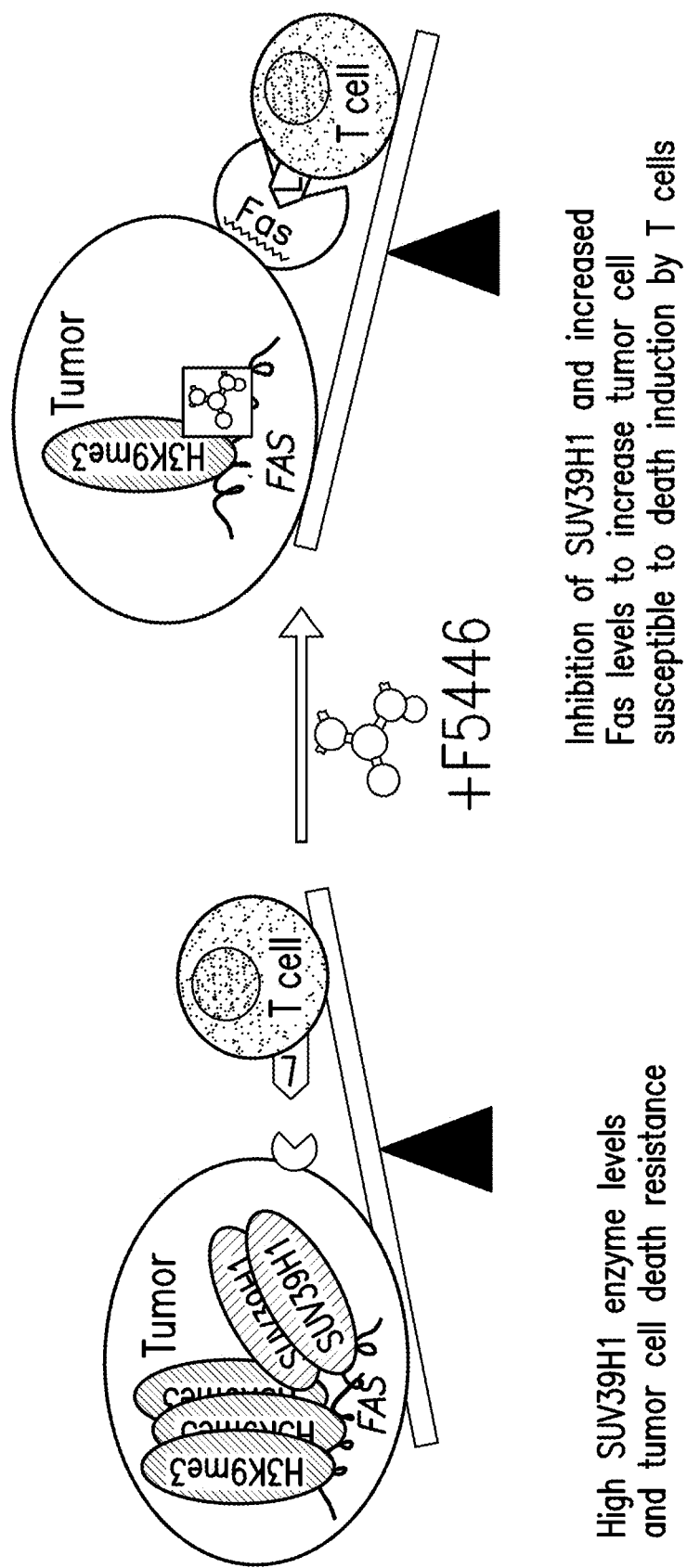
FIG. 1 is a schematic diagram showing the interplay between SUV39H1 levels, Fas levels, and tumor cell susceptibility to death.

As used herein, the singular forms "a," "an," and "the" include plural referents unless the context clearly dictates otherwise. For example, reference to "the method of treatment" includes reference to equivalent steps and methods known to those skilled in the art, and so forth.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments, the values may range in value either above or below the stated value in a range of approx. +/−5%; in other embodiments, the values may range in value either above or below the stated value in a range of approx. +/−2%; in other embodiments, the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The terms "treat," "treating," or "treatment" refers to alleviating, reducing, or inhibiting one or more symptoms or physiological aspects of a disease, disorder, syndrome, or condition. "Treatment" as used herein covers any treatment of a disease in a subject, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom.

The term "pharmaceutically-acceptable carrier" refers to one or more compatible solid or liquid fillers, diluents, or encapsulating substances that does not cause significant irritation to a human or other vertebrate animal and does not abrogate the biological activity and properties of the administered compound.

The terms "individual," "subject," and "patient" are used interchangeably herein, and refer to a mammal, including, but not limited to, humans, rodents, such as mice and rats, and other laboratory animals.

The term "cancer immunotherapy" refers to a treatment that uses the body's own immune system to help fight cancer. Cancer immunotherapies include, but are not limited to antibodies to treat cancer, immune checkpoint inhibitors, cancer vaccines, and cytokine therapy.

The term "checkpoint inhibitor" refers to drugs that target molecules like PD-1, PD-L1, and CTLA-4, which normally help keep the immune system in check.

The term "therapeutic failure", "non responder", "non-responsive" or "not respond" to treatment with a chemotherapeutic or immunotherapeutic agent, refers to a treated cancer patient not experiencing an improvement in at least one of the clinical parameters. This term also encompasses a poor response to therapy which indicates a very low level of response which is not clinically significant or sufficient. For example, low responsiveness to a chemotherapeutic or immunotherapeutic agent treatment may be reflected by poor survival.

The term, "alkyl," as used herein, refers to the radical of saturated or unsaturated aliphatic groups, including straight-chain alkyl, alkenyl, or alkynyl groups, branched-chain alkyl, alkenyl, or alkynyl groups, cycloalkyl, cyclcoalkenyl, cycloalkynyl groups, alkyl substituted cycloalkyl, cyclcoalkenyl, or cycloalkynyl groups, and cycloalkyl substituted alkyl, alkenyl, or alkynyl groups. Unless otherwise indicated, a straight chain or branched chain alkyl has 33 or fewer carbon atoms in its backbone, preferably 20 or fewer, and more preferably 12 or fewer.

The term, "alkyl," also includes one or more substitutions at one or more carbon atoms of the hydrocarbon radical as well as cycloalkyls, unsaturated alkyls, substituted alkyls, heteroalkyls. Suitable substituents include, but are not limited to, halogens, such as fluorine, chlorine, bromine, or iodine; hydroxyl; —NR₁R₂, wherein $R_1$ and $R_2$ are independently hydrogen, alkyl, or aryl, and wherein the nitrogen atom is optionally quaternized; —SR, wherein R is hydrogen, alkyl, or aryl; —CN; —NO₂; —COOH; carboxylate;

—COR, —COOR, or —CONR₂, wherein R is hydrogen, alkyl, or aryl; azide, aralkyl, alkoxyl, imino, phosphonate, phosphinate, silyl, ether, sulfonyl, sulfonamido, heterocyclic, aromatic or heteroaromatic moieties, —CF₃; —CN; —NCOCOCH₂CH₂; —NCOCOCHCH; —NCS; and combinations thereof.

The terms "alkenyl" and "alkynyl", as used herein, refer to unsaturated aliphatic groups analogous in length and possible substitution to the alkyls described above, but that contain at least one double or triple bond respectively.

The term "aryl" refers to a mono- or multi-cyclic aromatic radical having in the range of 6 up to 20 carbon atoms such as phenyl, naphthyl, tetrahydronapthyl, indanyl, and biphenyl.

The term, "heteroaryl," as used herein, refers to straight or branched chain, or cyclic carbon-containing radicals, or combinations thereof, having 3 to 20 carbon atoms where one or more of the carbon atoms are replaced by heteroatoms. Suitable heteroatoms include, but are not limited to, O, N, Si, P and S, where the nitrogen, phosphorous and sulfur atoms are optionally oxidized, and the nitrogen heteroatom is optionally quarternized. One of the rings may also be aromatic. Examples of heterocyclic and heteroaromatic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

The term, "acyl" as used herein, refers to alkylcarbonyl substituents.

II. Compositions for Inhibiting SUV39H1

The disclosed compositions inhibit SUV39H1, a histone methyltransferase ("HMTase") that catalyzes H3K9 trimethylation ("H3K9me3").

In one embodiment, the disclosed compositions include a compound according to general formula (I):

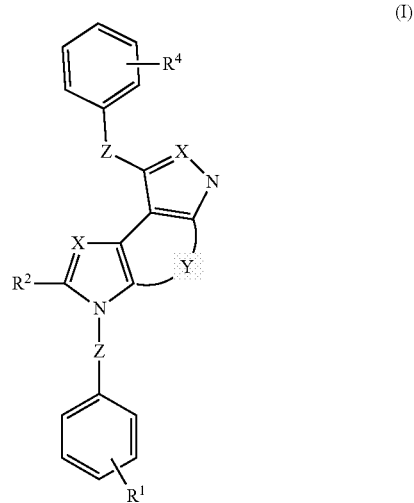

(I)

where:
$R^1$ and $R^4$ are each independently selected from —H, halogen, —NO₂, —CH₃, —O-alkyl, —N-alkyl, —S-alkyl, —NH₂, —COO—($C_1$-$C_{16}$)-alkyl, or —CONR⁵R⁶, $R^2$ is selected from —H, halogen, —O-alkyl, —N-alkyl, —S-alkyl, —($C_1$-$C_{33}$)-alkyl, -heteroaryl, -aryl, -acyl, or —COO—($C_1$-$C_{16}$)-alkyl, X is —CH or —N, Z is selected from —SO₂, —SO, —($C_1$-$C_{33}$)-alkyl, —($C_1$-$C_{33}$)-alkenyl, —CO((CH₂)$_n$), —O, —SOCH₃, —NS, or —S—S, Y is selected from —C═O—C═O, —($C_1$-$C_4$)-alkyl, —CH═CH—, —N, —O, —S, —CH₂R⁷CH₂, —CNC, —CN, or —NC, $R^5$ and $R^6$ are each independently selected from —H, —($C_1$-$C_4$)-alkyl, —($C_1$-$C_3$)-alkoxy-($C_2$-$C_4$)-alkyl, or —OH—($C_2$-$C_4$)-alkyl, $R^7$ is —S, —O, or —N, and n is 1 to 33.

In some embodiments, $R^1$ and $R^4$ may each independently be selected from —H, —F, —Cl, —Br, —I, —NO₂, —CH₃, —O—($C_1$-$C_{20}$)-alkyl, —N—($C_1$-$C_{20}$)-alkyl, —S—($C_1$-$C_{20}$)-alkyl, —NH₂, —COO—($C_1$-$C_{16}$)-alkyl, or —CONR⁵R⁶, where $R^5$ and $R^6$ are each independently selected from —H, —($C_1$-$C_4$)-alkyl, —($C_1$-$C_3$)-alkoxy-($C_2$-$C_4$)-alkyl, or —OH—($C_2$-$C_4$)-alkyl. In other embodiments, $R^1$ and $R^4$ may each independently be selected from —H, —F, —Cl, —NO₂, —CH₃, —O—($C_1$-$C_{12}$)-alkyl, —N—($C_1$-$C_{12}$)-alkyl, —S—($C_1$-$C_{12}$)-alkyl, —NH₂, or —COO—($C_1$-$C_{12}$)-alkyl. In still other embodiments, $R^1$ and $R^4$ may each independently be selected from —H, —F, —Cl, or —CH₃.

In certain embodiments, $R^2$ may be selected from —H, —F, —Cl, —Br, —I, —O—($C_1$-$C_{20}$)-alkyl, —N—($C_1$-$C_{20}$)-alkyl, —S—($C_1$-$C_{20}$)-alkyl, —($C_1$-$C_{20}$)-alkyl, —($C_3$-$C_{20}$)-heteroaryl, —($C_6$-$C_{20}$)-aryl, acyl, or —COO—($C_1$-

$C_{12}$)-alkyl. In other embodiments, $R^2$ may be selected from —H, —F, —Cl, —Br, —I, —O—($C_1$-$C_{12}$)-alkyl, —S—($C_1$-$C_{12}$)-alkyl, —($C_1$-$C_{12}$)-alkyl, —($C_3$-$C_{14}$)-heteroaryl, —($C_6$-$C_{14}$)-aryl, $R_y$—CO— where $R_y$ is a —($C_1$-$C_{12}$)-alkyl, —($C_3$-$C_6$)-cycloalkyl, or phenyl, or —COO—($C_1$-$C_4$)-alkyl. In still another embodiment, $R^2$ may be a —COO—($C_1$-$C_4$)-alkyl.

In some embodiments, Z may be selected from —$SO_2$, —SO, —($C_1$-$C_{20}$) alkyl, —($C_1$-$C_{20}$) alkenyl, —CO(($CH_2$)$_n$), —O, —$SOCH_3$, —NS, or —SS, where n is 1 to 20. In other embodiments, Z may be selected from —$SO_2$, —SO, —($C_1$-$C_{12}$) alkyl, —($C_1$-$C_{12}$) alkenyl, —CO(($CH_2$)$_n$), —O, or —$SOCH_3$, where n is 1 to 12. In yet another embodiment, Z may be selected from —$SO_2$, —SO, or —$SOCH_3$. In some embodiments, Z is —$SO_2$. In certain embodiments, Y is selected from —C═O—C═O, —($C_1$-$C_3$)-alkyl, —CH═CH—, —N, —O, —S, —$CH_2SCH_2$, —$CH_2OCH_2$, —$CH_2NCH_2$, —CNC, —CN, or —NC. In other embodiments, Y is selected from —C═O—C═O, —($C_1$-$C_2$)-alkyl, or —CH═CH—. In some embodiments, Y is —C═O—C═O.

In certain embodiments of the compounds of general formula (I), the aryl groups shown in formula (I) may each independently be replaced by a heteroaryl group. For example, the aryl rings in formula (I) may each independently be replaced by mono- or polycyclic aromatic hydrocarbyl radicals having 3 to 20 carbon atoms, where one or more of the carbon atoms are replaced by heteroatoms. Preferred heteroatoms are N, O, and S.

In one embodiment, the compounds of general formula (I) include the compound, 1-Benzyl 7-methyl 6-(4-chlorobenzenesulfonyl)-4,5-dioxo-3H,4H,5H,6H-pyrrolo[3,2-e]indole-1,7-dicarboxylate (hereinafter referred to as "compound 1" or "F5446"). Compound 1 has the following chemical structure:

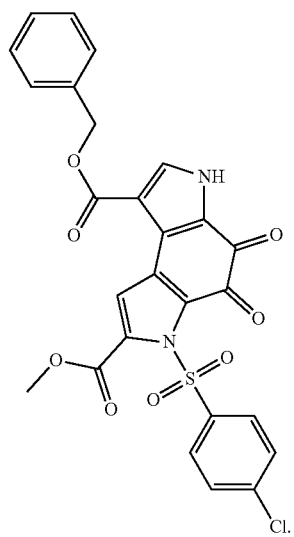

In another embodiment, the compounds of general formula (I) include the compound, 1-(4-Fluorophenyl)methyl 7-methyl 6-(4-methylbenzenesulfonyl)-4,5-dioxo-3H,4H,5H,6H-pyrrolo[3,2-e]indole-1,7-dicarboxylate (hereinafter referred to as "compound 2"). Compound 2 has the following chemical structure:

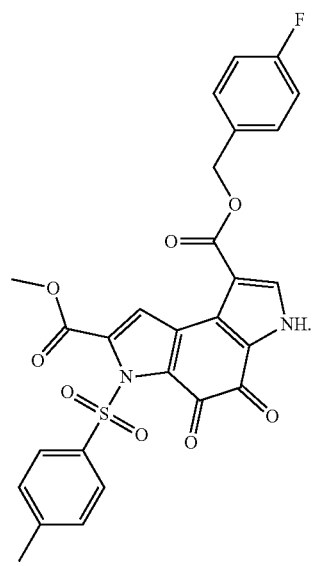

The disclosed compositions may further include enantiomers, hydrates, polymorphs, pharmaceutically acceptable salts, esters (saturated or unsaturated), structural analogs, isomers, tautomers, and derivatives of the compounds of general formula (I). As used herein, "compounds of general formula (I)" refer to any one or combination of compounds of general formula (I), and enantiomers, hydrates, polymorphs, pharmaceutically acceptable salts, esters, structural analogs, isomers, tautomers, and derivatives thereof.

In some embodiments, the disclosed compositions may include one or more derivatives of compounds of general formula (I). The term "derivative" or "derivatized" as used herein includes one or more chemical modifications of compounds of general formula (I) and enantiomers, hydrates, polymorphs, pharmaceutically acceptable salts, esters, structural analogs, isomers, or tautomers thereof. That is, a "derivative" may be a functional equivalent of a compound of general formula (I), which is capable of inducing the improved pharmacological functional activity and/or behavioral response in a given subject. Exemplary chemical modifications include, but are not limited to, replacement of an alkyl group with a homolog and replacement of hydrogen by a halo group, an alkyl group, an alkoxy group, a hydroxyl group, a carboxylate, an acyl group, or an amino group.

In other embodiments, compounds of general formula I may act as a model (for example, a template) for the development of other derivative compounds which are a functional equivalent of the compound and which are capable of inducing the improved pharmacological functional activity and/or behavioral response in a given subject.

Compounds of general formula I may be racemic compounds and/or optically active isomers thereof. In this regard, some of the compounds can have asymmetric carbon atoms, and therefore, can exist either as racemic mixtures or as individual optical isomers (enantiomers) or as tautomers, for example, keto-enol and lactam-lactim tautomers. Compounds described herein that contain a chiral center include all possible stereoisomers of the compound, including compositions including the racemic mixture of the two enantiomers, as well as compositions including each enantiomer individually, substantially free of the other enantiomer.

One embodiment provides an immunotherapy composition including 1-Benzyl 7-methyl 6-(4-chlorobenzenesulfonyl)-4,5-dioxo-3H,4H,5H,6H-pyrrolo[3,2-e]indole-1,7-dicarboxylate and a cancer immunotherapy, wherein 1-Benzyl 7-methyl 6-(4-chlorobenzenesulfonyl)-4,5-dioxo-3H,4H,5H,6H-pyrrolo[3,2-e]indole-1,7-dicarboxylate is in an amount effective to potentiate the activity of the cancer immunotherapy.

A. Pharmaceutical Compositions

Pharmaceutical compositions including compounds of general formula (I) are provided. In general, pharmaceutical compositions are provided including effective amounts of one or more compounds of general formula (I), and optionally pharmaceutically acceptable diluents, preservatives, solubilizers, emulsifiers, adjuvants, excipients, and/or carriers. Pharmaceutical compositions can be formulated for administration by parenteral (for example, intramuscular, intraperitoneal, intravitreally, intravenous (IV), or subcutaneous injection), enteral, transmucosal (for example, nasal, vaginal, rectal, or sublingual), or transdermal routes of administration or using bioerodible inserts including ocular inserts and can be formulated in dosage forms appropriate for each route of administration.

In some in vivo approaches, the compositions disclosed herein are administered to a subject in a therapeutically effective amount. As used herein, the term "effective amount" or "therapeutically effective amount" means a dosage sufficient to treat, inhibit, or alleviate one or more symptoms of the disease being treated or to otherwise provide a desired pharmacologic and/or physiologic effect. The precise dosage will vary according to a variety of factors such as subject-dependent variables (for example, age, immune system health, etc.).

In this aspect, the selected dosage depends upon the desired therapeutic effect, on the route of administration, and on the duration of the treatment desired. However, for the disclosed compositions, generally dosage levels of about 0.001 mg/kg to about 100 mg/kg of body weight are administered to mammals daily. In some embodiments, the disclosed compositions may be administered to a subject in a dosage level of about 0.5 mg/kg to about 50 mg/kg. For example, the disclosed compositions may be administered to a subject in a dosage level of about 0.5 mg/kg to about 5 mg/kg. Generally, for intravenous injection or infusion, the dosage may be lower.

In some embodiments, the compositions disclosed herein are administered in combination with one or more additional active agents, for example, small molecules or mAB. The combination therapies can include administration of the active agents together in the same admixture, or in separate admixtures. Therefore, in some embodiments, the pharmaceutical composition includes two, three, or more active agents. The pharmaceutical compositions can be formulated as a pharmaceutical dosage unit, referred to as a unit dosage form. Such compositions typically include an effective amount of one or more of the disclosed compounds. The different active agents can have the same or different mechanisms of action. In some embodiments, the combination results in an additive effect on the treatment of the disease or disorder. In some embodiments, the combinations result in a more than additive effect on the treatment of the disease or disorder.

In certain embodiments, the disclosed compositions are administered locally, for example, by injection directly into a site to be treated (for example, into a tumor). In other embodiments, the compositions are injected or otherwise administered directly into the vasculature onto vascular tissue at or adjacent to the intended site of treatment (for example, adjacent to a tumor). Typically, the local administration causes an increased localized concentration of the composition which is greater than that which can be achieved by systemic administration.

1. Formulations for Parenteral Administration

In some embodiments, the compositions disclosed herein are formulated for parenteral injection, for example in an aqueous solution. The formulation may also be in the form of a suspension or emulsion. As discussed above, pharmaceutical compositions are provided including effective amounts of one or more compounds of general formula I, and optionally pharmaceutically acceptable diluents, preservatives, solubilizers, emulsifiers, adjuvants, excipients, and/or carriers. Such compositions may optionally include one or more of the following: diluents, sterile water, buffered saline of various buffer content (for example, Tris-HCl, acetate, phosphate), pH and ionic strength, ionic liquids, and HPßCD; and additives such as detergents and solubilizing agents (for example, TWEEN®20 (polysorbate-20), TWEEN®80 (polysorbate-80)), anti-oxidants (for example, ascorbic acid, sodium metabisulfite), and preservatives (for example, Thimersol, benzyl alcohol) and bulking substances (for example, lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Enteral Administration

In some embodiments, the disclosed compositions are formulated for enteral administration including oral, sublingual, and rectal delivery. In one embodiment, the disclosed compositions are administered in solid dosage form. Suitable solid dosage forms include tablets, capsules, pills, solutions, suspensions, syrups, lozenges, cachets, pellets, powders, or granules or incorporation of the material into particulate preparations of polymeric compounds such as polylactic acid, polyglycolic acid, or into liposomes. In another embodiment, the disclosed compositions are administered in liquid dosage form. Examples of liquid dosage forms for enteral administration include pharmaceutically acceptable emulsions, solutions, suspensions, and syrups, which may contain other components including inert diluents; preservatives; binders; stabilizers; adjuvants such as wetting agents, emulsifying and suspending agents; and sweetening, flavoring, and perfuming agents.

Controlled release oral formulations, for example, delayed release or extended release formulations, may also be desirable. For example, the disclosed compounds may be encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings (for example, delayed release or extended release coatings) prior to incorporation into the finished dosage form. In still another embodiment, the disclosed compounds may be dispersed in a matrix material, which gels or emulsifies upon contact with an aqueous medium. Such matrices may be formulated as tablets or as fill materials for hard and soft capsules.

For enteral formulations, the location of release may be the stomach, the small intestine (the duodenum, the jejunum, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance, a coating impermeable to at least pH 5.0 is essential. Examples of common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™, cellulose acetate phthalate (CAP), Eudragit L™, Eudragit S™, and Shellac™. These coatings may be used as mixed films.

3. Formulations for Topical Administration

In other embodiments, the disclosed compositions are formulated for topical application. For example, the disclosed compositions can be formulated for application to the lungs, nasal, oral (sublingual, buccal), vaginal, or rectal mucosa.

The compositions can be delivered to the lungs while inhaling and traverse across the lung epithelial lining to the blood stream when delivered either as an aerosol or spray dried particles having an aerodynamic diameter of less than about 5 microns.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations can include penetration enhancers.

III. Methods of Use

The disclosed compositions can be used, for example, to inhibit methyltransferase activity, to treat certain types of cancer, to activate T cell effectors including perforin, granzyme, FasL and IFNgamma in tumor-infiltrating T cells, to induce apoptosis in a cancer cell of a subject, increase cell sensitivity to FasL-induced apoptosis in a subject, or increase cancer cell sensitivity to cancer immunotherapy.

In some embodiments, the effect of the composition on a subject is compared to a control. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or an average determined from measuring the symptom, pharmacologic, or physiologic indicator in one or more subjects that do not have the disease or condition to be treated (for example, healthy subjects). In some embodiments, the effect of the treatment is compared to a conventional treatment that is known in the art. For example, if the disease to be treated is cancer, the conventional treatment could be a chemotherapeutic agent.

A. Methods of Inhibiting Methyltransferase Activity

One embodiment provides a method for inhibiting methyltransferase in a subject in need thereof. For example, the compounds and compositions can be used to inhibit SUV39H1 methyltransferase activity in the subject.

SUV39H1 is an HMTase that catalyzes H3K9me3. H3K9me3 is known in the art to be a silencer of tumor suppressors, such as Fas. H3K9me3 also silences PRF1, GZMB, FASLG and IFNG in T cells (FIGS. 8A-D, 9A-H). In one embodiment, inhibition of methyltransferases including SUV39H1 can down-regulate or decrease H3K9me3 levels in T cell effector promoter regions to increase the expression of PRF1, GZMB, FASLG and IFNG in tumor-infiltrating T cells (FIGS. 16A-H, 20E-H, 21A-L). This action will reverse tumor-induced T cell suppression to enable T cells to kill tumor cells (FIGS. 17A, 17B, 18A, 18B, 19A-D). In another embodiment, inhibition of methyltransferases including SUV39H1 can down-regulate or decrease H3K9me3 levels in cancer cells to up-regulate or increase cell surface Fas receptor expression in tumor cells. This, in turn, increases the susceptibility of cancer cells to death induction by T cells.

FIG. 1 is an exemplary model showing the interplay between SUV39H1 levels, Fas levels, and tumor cell susceptibility to death. As shown in FIG. 1, high SUV39H1 enzyme levels are associated with tumor cell death resistance. By inhibiting SUV39H1, Fas receptor expression levels are increased in cancer or tumor cells, thereby increasing the susceptibility of cancer or tumor cells to Fas mediated apoptosis. T cells express FasL, and therefore increasing Fas receptor expression in cancer or tumor cells increases the susceptibility of the cancer and tumor cells to T cell mediated apoptosis.

The disclosed compositions are useful for inhibiting methyltransferase activity in a cancer cell of a patient, in particular SUV39H1 activity. One embodiment provides a method for inhibiting SUV39H1 methyltransferase activity in a cancer cell of a subject in need thereof by administering to the subject an effective amount of compositions containing a compound according to formula I.

B. Methods of Treating Cancer

In one embodiment, the disclosed compositions are administered to a subject having or suspected of having cancer in an amount effective to inhibit or reduce tumor growth. It has been discovered that the disclosed SUV39H1-inhibiting compositions provide for decreased H3K9me3 levels to: 1) increase the expression levels of perforin, granzyme B, FasL and IFNgamma in tumor-infiltrating T cells, which makes T cell cytotoxic to kill tumor cells; and 2) increase Fas expression levels in tumor cells, which in turn, increases the sensitivity of the tumor cells to T cell-induced cell death.

Exemplary types of cancer and related disorders that can be treated with the disclosed compositions include, but are not limited to, the following: acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease or non-Hodgkin's disease lymphomas (e.g., diffuse anaplastic lymphoma kinase (ALK) negative, large B-cell lymphoma (DLBCL); diffuse anaplastic lymphoma kinase (ALK) positive, large B-cell lymphoma (DLBCL); anaplastic lymphoma kinase (ALK) positive, ALK+ anaplastic large-cell lymphoma (ALCL), acute myeloid lymphoma (AML)); multiple myelomas such as, but not limited to, smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and cilliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In one embodiment, the disclosed compositions are administered to a subject having or suspected of having colorectal cancer (for example, colon and/or rectal). Without being bound by any particular theory, it is believed that H3K9me3-mediated silencing of T cell effectors including PRF1, GZMB, FASLG and IFNG leads to suppression of T cell function in host cancer immune surveillance to promote tumor growth and progression. Inhibition of SUV39H1 decreases H3K9me3 levels at the promoters of PRF1, GZMB, FASLG and IFNG to increase the expression of these 4 genes in T cells, resulting in significant killing of tumor cells by T cells. H3K9me3 also silences the tumor suppressor, Fas, which is an underlying mechanism of colon cancer resistance to cancer immunotherapy. It has been shown that the expression levels of SUV39H1 (which is an H3K9me3-specific HMTase) are significantly higher in both tumor cells and tumor-infiltrating T cells in colon carcinoma tissues than in normal colon tissues, while the expression levels of Fas are significantly lower in human colon carcinoma tissues than in normal colon tissues. However, it has been discovered that the disclosed SUV39H1-inhibiting compositions provide for decreased H3K9me3 levels in colon carcinoma cells (and increased Fas expression levels), which increases the susceptibility of colon carcinoma cells to death induction by T cells and allows for enhanced efficacy of colon cancer immunotherapy. Thus, the disclosed compositions are useful for inhibiting or reducing tumor growth associated with colorectal cancer.

In another embodiment, the disclosed compositions are administered to a subject having or suspected of having pancreatic cancer. In this aspect, the disclosed SUV39H1-inhibiting compositions provide for decreased H3K9me3 levels in pancreatic tumor-infiltrating T cells to increase the expression levels of perforin, granzyme B, FasL and IGNgamma to kill tumor cells to suppress pancreatic cancer. The disclosed compounds also decrease H3K9me3 level in pancreatic cancer cells (and increased Fas expression levels), which increases the susceptibility of pancreatic cancer cells to death induction by T cells and allows for enhanced efficacy of pancreatic cancer immunotherapy. Thus, the disclosed compositions can be useful for inhibiting or reducing tumor growth associated with pancreatic cancer.

In some embodiments, administration of the disclosed compositions induces apoptosis in a cancer cell of a patient. This embodiment provides for a method of inducing apoptosis in a cancer cell of a subject by administering to a subject in need thereof an effective amount of the disclosed compositions. For example, the disclosed compositions may induce apoptosis in colon carcinoma cells and/or pancreatic cancer cells.

In other embodiments, administration of the disclosed compositions increases cancer or tumor cell sensitivity to apoptosis, for example, FasL-induced apoptosis, and/or cancer immunotherapy. This embodiment provides for a method of overcoming cancer cell resistance to apoptosis and/or cancer immunotherapy by administering to a subject in need thereof an effective amount of the disclosed compositions. For instance, the disclosed compositions may overcome colon carcinoma cell resistance and/or pancreatic cancer cell resistance to FasL-induced apoptosis and/or cancer immunotherapy, such as anti-PD-1/PD-L1 immunotherapy.

C. Co-Therapies

In one embodiment, the disclosed compositions can be administered to a subject in need thereof in combination with: an antimicrobial such as an antibiotic, or an antifungal, or an antiviral, or an antiparasitic, or an essential oil, or a combination thereof.

The disclosed compositions can be administered to a subject in need thereof in combination or alternation with other therapies and therapeutic agents. In some embodiments, the disclosed compositions and the additional therapeutic agent are administered separately, but simultaneously, or in alternation. The disclosed compositions and the additional therapeutic agent can also be administered as part of the same composition. In other embodiments, the disclosed compositions and the second therapeutic agent are administered separately and at different times, but as part of the same treatment regime.

1. Treatment Regimes

The subject can be administered the disclosed compositions as a monotherapeutic agent to induce expression of perforin, granzyme, Fasl and IFNgamma in tumor-infiltrating T cells, which will reverse tumor-induced immune suppression of T cells to kill the tumor cells to repress cancer.

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 6 7, 14, 21, 28, 35, or 48 days prior to a first administration of second agent. The disclosed compositions can be the first or the second therapeutic agent.

The disclosed compositions and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary molecules include, but are not limited to, cytokines, chemotherapeutic agents, radionuclides, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, ligands that bind to Toll-Like Receptors (including but not limited to CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

The additional therapeutic agents are selected based on the condition, disorder or disease to be treated. For example, the disclosed compositions can be co-administered with one or more additional agents that function to enhance or promote an immune response or reduce or inhibit an immune response.

2. Antimicrobials

One embodiment provides compositions containing one or compounds according to formula I and an antimicrobial agent and methods of their use. For example, the disclosed compositions can be used in a preventive or prophylactic role in the treatment and prevention of disease as discussed above.

In some embodiments, the subject is administered the disclosed compositions and/or the antimicrobial at time of admission to the hospital to prevent further bacterial, fungal or viral complications. The antibiotic can target pathogens and the disclosed compositions can stimulate the immune system to provide an enhanced response to treat or prevent further infection or disease.

3. Chemotherapeutic Agents

One embodiment provides compositions containing one or compounds according to formula I and a chemotherapeutic agent and methods of their use. The disclosed compositions can be used as monotherapeutic agents, combined with one or more chemotherapeutic agents, or one or more pro-apoptotic agents other than compounds according to formula 1, or a combination thereof.

Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof. In some embodiments, the disclosed compositions can be combined with one or more monoclonal antibodies (mAB).

4. Immunomodulators a. PD-1 Antagonists

In some embodiments, the disclosed compositions are combined with or co-administered with a PD-1 antagonist. Programmed Death-1 (PD-1) is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response. Suitable PD-1 antagonists are described in U.S. Pat. Nos. 8,114,845, 8,609,089, and 8,709,416, which are specifically incorporated by reference herein in their entities, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as B7-H1 or B7-DC) in close proximity to a peptide antigen presented by major histocompatibility complex (MHC) (see, for example, Freeman, Proc. Natl. Acad. Sci. U.S.A, 105:10275-10276 (2008)). Therefore, proteins, antibodies or small molecules that prevent co-ligation of PD-1 and TCR on the T cell membrane are also useful PD-1 antagonists.

In some embodiments, the PD-1 receptor antagonists are small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor. Other PD-1 antagonists contemplated by the methods of this invention include antibodies that bind to PD-1 or ligands of PD-1, and other antibodies.

Suitable anti-PD-1 antibodies include, but are not limited to, those described in the following U.S. Pat. Nos. 7,332,582, 7,488,802, 7,521,051, 7,524,498, 7,563,869, 7,981,416, 8,088,905, 8,287,856, 8,580,247, 8,728,474, 8,779,105, 9,067,999, 9,073,994, 9,084,776, 9,205,148, 9,358,289, 9,387,247, 9,492,539, 9,492,540, all of which are incorporated by reference in their entireties.

See also Berger et al., Clin. Cancer Res., 14:30443051 (2008).

Exemplary anti-B7-H1 (also referred to as anti-PD-L1) antibodies include, but are not limited to, those described in the following U.S. Pat. Nos. 8,383,796, 9,102,725, 9,273,135, 9,393,301, and 9,580,507, all of which are specifically incorporated by reference herein in their entirety.

For anti-B7-DC (also referred to as anti-PD-L2) antibodies see U.S. Pat. Nos. 7,411,051, 7,052,694, 7,390,888, 8,188,238, and 9,255,147, all of which are specifically incorporated by reference herein in their entirety.

Other exemplary PD-1 receptor antagonists include, but are not limited to B7-DC polypeptides, including homologs and variants of these, as well as active fragments of any of the foregoing, and fusion proteins that incorporate any of these. In some embodiments, the fusion protein includes the soluble portion of B7-DC coupled to the Fc portion of an antibody, such as human IgG, and does not incorporate all or part of the transmembrane portion of human B7-DC.

The PD-1 antagonist can also be a fragment of a mammalian B7-H1, for example from mouse or primate, such as a human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as B7-H1 or B7-DC, and prevent binding to the endogenous PD-1 receptor, thereby preventing inhibitory signal transduction. B7-H1 has also been shown to bind the protein B7.1 (Butte et al., Immunity, Vol. 27, pp. 111-122, (2007)). Such fragments also include the soluble ECD portion of the PD-1 protein that includes mutations, such as the A99L mutation, that increases binding to the natural ligands (Molnar et al., PNAS, 105:10483-10488 (2008)). B7-1 or soluble fragments thereof, which can bind to the B7-H1 ligand and prevent binding to the endogenous PD-1 receptor, thereby preventing inhibitory signal transduction, are also useful.

PD-1 and B7-H1 anti-sense nucleic acids, both DNA and RNA, as well as siRNA molecules can also be PD-1 antagonists. Such anti-sense molecules prevent expression of PD-1 on T cells as well as production of T cell ligands, such as B7-H1, PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., J. Clin. Invest. 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

b. CTLA4 Antagonists

In some embodiments, the disclosed compositions are combined with or co-administered with one or more CTLA4 antagonists, for example an antagonistic anti-CTLA4 antibody. An example of an anti-CTLA4 antibody contemplated for use in the methods of the invention includes an antibody as described in U.S. Pat. No. 9,487,581

Dosages for anti-PD-1, anti-B7-H1, and anti-CTLA4 antibody, are known in the art and can be in the range of, for example, 0.1 to 100 mg/kg, or with shorter ranges of 1 to 50 mg/kg, or 10 to 20 mg/kg. An appropriate dose for a human subject can be between 5 and 15 mg/kg, with 10 mg/kg of antibody (for example, human anti-PD-1 antibody) being a specific embodiment.

Specific examples of an anti-CTLA4 antibody useful in the methods of the invention are Ipilimumab, a human anti-CTLA4 antibody, administered at a dose of, for example, about 10 mg/kg, and Tremelimumab a human anti-CTLA4 antibody, administered at a dose of, for example, about 15 mg/kg. See also Sammartino, et al., Clinical Kidney Journal, 3(2):135-137 (2010), published online December 2009.

In other embodiments, the antagonist is a small molecule. A series of small organic compounds have been shown to bind to the B7-1 ligand to prevent binding to CTLA4 (see Erbe et al., J. Biol. Chem., 277:7363-7368 (2002). Such small organics could be administered alone or together with an anti-CTLA4 antibody to reduce inhibitory signal transduction of T cells.

c. Potentiating Agents

In some embodiments, the compositions are combined with or administered with a potentiating agent or than a compound according to formula 1. The potentiating agent acts to increase the efficacy of the immune response up-regulator, possibly by more than one mechanism, although the precise mechanism of action is not essential to the broad practice of the present invention.

In some embodiments, the potentiating agent is cyclophosphamide. Cyclophosphamide (CTX, Cytoxan®, or Neosar®) is an oxazahosphorine drug and analogs include ifosfamide (IFO, Ifex), perfosfamide, trophosfamide (trofosfamide; Ixoten), and pharmaceutically acceptable salts, solvates, prodrugs and metabolites thereof (US patent application 20070202077 which is incorporated in its entirety). Ifosfamide (MITOXANA®) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Liang J, Huang M, Duan W, Yu X Q, Zhou S. Design of new oxazaphosphorine anticancer drugs. Curr Pharm Des. 2007; 13(9):963-78. Review). These include mafosfamide (NSC 345842), glufosfamide (D19575, beta-D-glucosylisophosphoramide mustard), S-(−)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety.

While CTX itself is nontoxic, some of its metabolites are cytotoxic alkylating agents that induce DNA crosslinking and, at higher doses, strand breaks. Many cells are resistant to CTX because they express high levels of the detoxifying enzyme aldehyde dehydrogenase (ALDH). CTX targets proliferating lymphocytes, as lymphocytes (but not hematopoietic stem cells) express only low levels of ALDH, and cycling cells are most sensitive to DNA alkylation agents.

Low doses of CTX (<200 mg/kg) can have immune stimulatory effects, including stimulation of anti-tumor immune responses in humans and mouse models of cancer (Brode & Cooke Crit Rev. Immunol. 28:109-126 (2008)). These low doses are sub-therapeutic and do not have a direct anti-tumor activity. In contrast, high doses of CTX inhibit the anti-tumor response. Several mechanisms may explain the role of CTX in potentiation of anti-tumor immune response: (a) depletion of CD4+CD25+FoxP3+ Treg (and specifically proliferating Treg, which may be especially suppressive), (b) depletion of B lymphocytes; (c) induction of nitric oxide (NO), resulting in suppression of tumor cell growth; (d) mobilization and expansion of CD11b+Gr-1+ MDSC. These primary effects have numerous secondary effects; for example following Treg depletion macrophages produce more IFN-γ and less IL-10. CTX has also been shown to induce type I IFN expression and promote homeostatic proliferation of lymphocytes.

Treg depletion is most often cited as the mechanism by which CTX potentiates the anti-tumor immune response. This conclusion is based in part by the results of adoptive transfer experiments. In the AB1-HA tumor model, CTX treatment at Day 9 gives a 75% cure rate. Transfer of purified Treg at Day 12 almost completely inhibited the CTX response (van der Most et al. Cancer Immunol. Immunother. 58:1219-1228 (2009). A similar result was observed in the HHD2 tumor model: adoptive transfer of CD4+CD25+ Treg after CTX pretreatment eliminated therapeutic response to vaccine (Taieb, J. J. Immunol. 176:2722-2729 (2006)).

Numerous human clinical trials have demonstrated that low dose CTX is a safe, well-tolerated, and effective agent for promoting anti-tumor immune responses (Bas, & Mastrangelo Cancer Immunol. Immunother. 47:1-12 (1998)).

The optimal dose for CTX to potentiate an anti-tumor immune response, is one that lowers overall T cell counts by lowering Treg levels below the normal range but is subtherapeutic (see Machiels et al. Cancer Res. 61:3689-3697 (2001)).

In human clinical trials where CTX has been used as an immunopotentiating agent, a dose of 300 mg/m$^2$ has usually been used. For an average male (6 ft, 170 pound (78 kg) with a body surface area of 1.98 m$^2$), 300 mg/m$^2$ is 8 mg/kg, or 624 mg of total protein. In mouse models of cancer, efficacy has been seen at doses ranging from 15-150 mg/kg, which relates to 0.45-4.5 mg of total protein in a 30 g mouse (Machiels et al. Cancer Res. 61:3689-3697 (2001), Hengst et al Cancer Res. 41:2163-2167 (1981), Hengst Cancer Res. 40:2135-2141 (1980)).

For larger mammals, such as a primate, such as a human, patient, such mg/m$^2$ doses may be used but unit doses administered over a finite time interval may also be used. Such unit doses may be administered on a daily basis for a finite time period, such as up to 3 days, or up to 5 days, or up to 7 days, or up to 10 days, or up to 15 days or up to 20 days or up to 25 days, are all specifically contemplated by the invention. The same regimen may be applied for the other potentiating agents recited herein.

In other embodiments, the potentiating agent is an agent that reduces activity and/or number of regulatory T lymphocytes (T-regs), such as Sunitinib) (SUTENT®), anti-TGFβ or Imatinib)(GLEEVAC®). The recited treatment regimen may also include administering an adjuvant.

Useful potentiating agents also include mitosis inhibitors, such as paclitaxol, aromatase inhibitors (e.g. Letrozole) and angiogenesis inhibitors (VEGF inhibitors e.g. Avastin, VEGF-Trap) (see, for example, Li et al., Vascular endothelial growth factor blockade reduces intratumoral regulatory T cells and enhances the efficacy of a GM-CSF-secreting cancer immunotherapy. Clin Cancer Res. 2006 Nov. 15; 12(22):6808-16.), anthracyclines, oxaliplatin, doxorubicin, TLR4 antagonists, and IL-18 antagonists.

d. Anti-Inflammatories

Other suitable therapeutic agents include, but are not limited to, anti-inflammatory agents. The anti-inflammatory agent can be non-steroidal, steroidal, or a combination thereof. One embodiment provides oral compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acemetacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

EXAMPLES

Example 1: Synthesis of Compounds 1 and 2

Based on the structures of the human SUV39H1 protein, molecular docking was used to screen a NCI small molecule virtual chemical library. A list of hit compounds with high affinity for the catalytic domain of the SUV39H1 protein was generated. In vitro HMTase enzymatic activity assays with a defined biochemical assay system identified a compound that effectively inhibits SUV39H1 methyltransferase activity in a dose-dependent manner. Structure-function study was performed and an analoging approach was used to design compounds with high enzymatic inhibitory activity and high solubility. The synthesis procedure, shown in Scheme 1 below, was developed to synthesize the compounds. Compounds of general formula I were identified as SUV39H1 inhibitors.

Synthesis of compound 1 (referred to in Example 1 as "5a") and compound 2 (referred to in Example 1 as "5b") was conducted by Leadgen Labs LLC using commercially available reagents and using methods described in the literature (Carter, P., Fitzjohn, S., Halazy, S., Magnus, P. Studies on the Synthesis of the Antitumor Agent CC-1065. Synthesis of PDE I and PDE 11, Inhibitors of Cyclic Adenosine-3',5'-monophosphate Phosphodiesterase Using the 3,3'-Bipyrrole Strategy. *J. Am. Chem. Soc.,* 1987, 109 (9), pp 2711-2717).

Synthesis

Compounds 1 and 2 may be prepared as illustrated in Scheme 1 below.

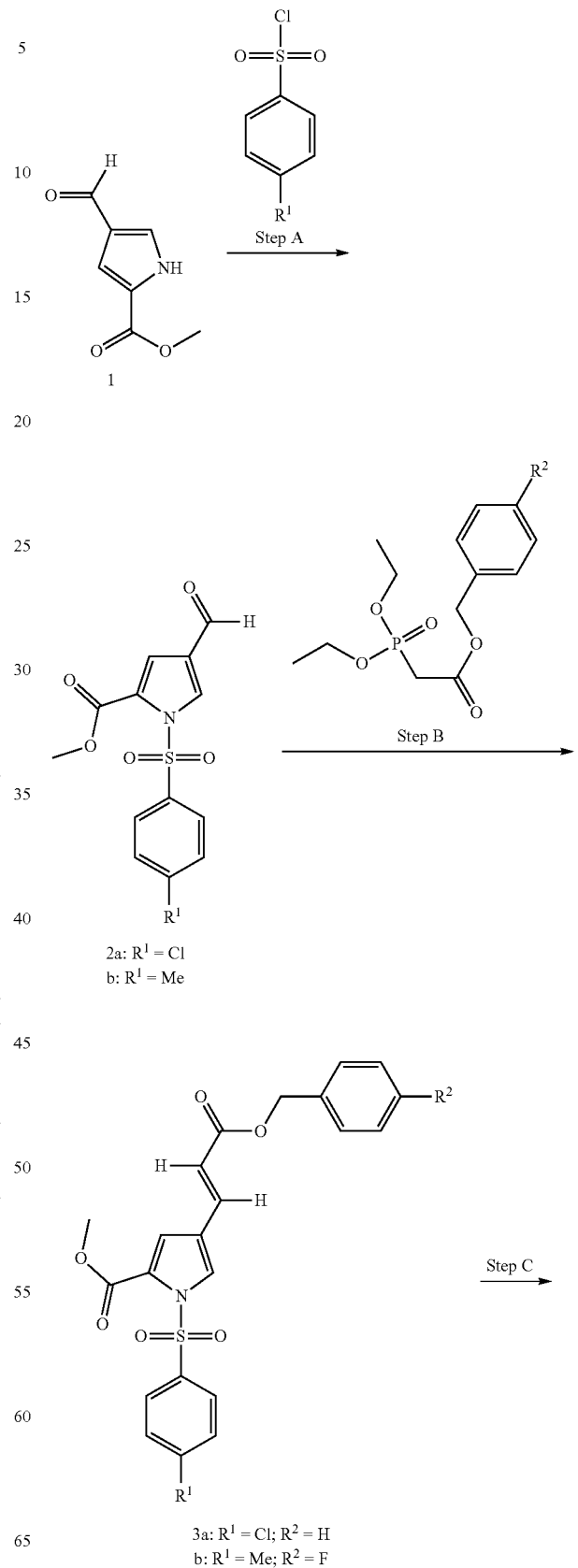

SCHEME 1. SYNTHESIS OF COMPOUNDS 1 AND 2

-continued

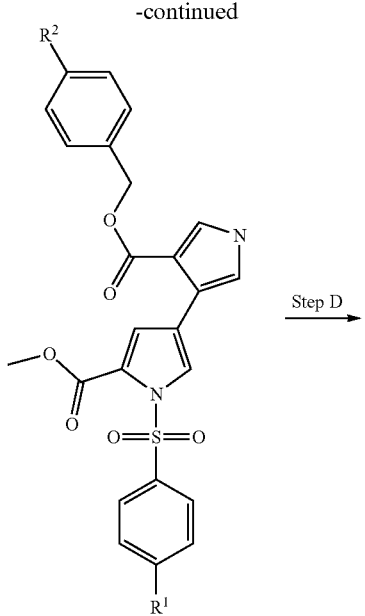

4a: R¹ = Cl; R² = H
b: R¹ = Me; R² = F

5a: R¹ = Cl; R² = H
b: R¹ = Me; R² = F

Step A:

Synthesis of Methyl 1-(4-chlorobenzenesulfonyl)-4-formyl-1H-pyrrole-2-carboxylate (2a)

Solution of pyrrole 1 (1.0 g, 6.5 mmol) in THF (15 mL) was slowly added to a suspension of NaH (0.36 g, 60% in mineral oil, 9.0 mmol) in THF (15 mL). The reaction mixture was then stirred for 1 h at r.t. followed by slow addition of p-ClPhSO₂Cl (1.65 g, 7.8 mmol) in 15 mL of THF. Reaction mixture was then stirred at r.t. overnight followed by quenching with $CH_3COOH$. After solvent was evaporated, the crude product was purified by column chromatography using hexane/EtOAc=7/3. Product 2a was isolated with the yield of 1.7 g, 70%.

Synthesis of Methyl 4-formyl-1-(4-methylbenzenesulfonyl)-1H-pyrrole-2-carboxylate (2b)

The procedure for 2a was applied. Product 2b was isolated with the yield of 1.4 g, 70%.

Step B:

Synthesis of Methyl 4-[(1E)-3-(benzyloxy)-3-oxo-prop-1-en-1-yl]-1-(4-chlorobenzenesulfonyl)-1H-pyrrole-2-carboxylate (3a)

$(EtO)_2P(O)CH_2CO_2Bn$ (1.69 g, 5.9 mmol) was added dropwise at −30° C. to a suspension of NaH (0.29 g 60% in mineral oil, 6.7 mmol) in THF (12 mL) and the mixture was then warmed up to 0° C. After the mixture was cooled to −30° C., the pyrrole 2a (1.7 g, 5.2 mmol) in THF (10 mL) was added at −10° C. After 5 min of stirring the mixture was quenched with 10% aqueous $NH_4Cl$ (7 mL), and the THF was evaporated under reduced pressure. The residue was extracted with $CH_2Cl_2$ (3×50 mL), dried ($Na_2SO_4$), and evaporated to give a tan solid (2.1 g). Recrystallization from acetone gave 3a: 1.56 g, 74%.

Synthesis of Methyl 4-[(1E)-3-[(4-fluorophenyl)methoxy]-3-oxoprop-1-en-1-yl]-1-(4-ethylbenzenesulfonyl)-1H-pyrrole-2-carboxylate (3b)

The procedure for 3a was applied and produced a yield of product 3b of 1.42 g, 65%.

Step C:

Synthesis of Methyl 4-{4-[(benzyloxy)carbonyl]-1H-pyrrol-3-yl}-1-(4-chlorobenzenesulfonyl)-1H-pyrrole-2-carboxylate (4a)

Freshly prepared LiHMDS [prepared from HMDS (0.88 g, 5.4 mmol) and 2.5 M n-BuLi (1.56 mL, 3.9 mmol) in THF (8 mL)] was added at −78° C. to a solution of TosMIC (0.64 g, 3.3 mmol) and 3a (1.13 g, 2.5 mmol) in THF (25 mL). After stirring for 15 min at −70° C., the reaction mixture was quenched with 10% aqueous $NH_4Cl$ (8 mL) and evaporated under reduced pressure to remove THF. The residue was then extracted with $CH_2Cl_2$ (4×20 mL), dried ($Na_2SO_4$), and filtered. After evaporation the residue was chromatographed over silica gel using 5% EtOAc/25% petroleum ether/70% $CH_2Cl_2$ to give 4a. Yield 0.55 g, 45%

Synthesis of Methyl 4-(4-{[(4-fluorophenyl)methoxy]carbonyl}-1H-pyrrol-3-yl)-1-(4-methylbenzenesulfonyl)-1H-pyrrole-2-carboxylate (4b)

The procedure for 4a was applied. Yield 0.75 g, 44%.

Step D:

Synthesis of 1-Benzyl 7-methyl 6-(4-chlorobenzenesulfonyl)-4,5-dioxo-3H,4H,5H,6H-pyrrolo[3,2-e]indole-1,7-dicarboxylate (5a)

Oxalyl chloride (0.11 mL, 1.3 mmol) was added dropwise to a solution of the bipyrrole 4a (0.52 g, 1.0 mmol) in $CH_2Cl_2$ (20 mL) at 0° C. More oxalyl chloride (0.06 mL) was slowly added in an hour, and the mixture was left at 0°

Figure 2A:
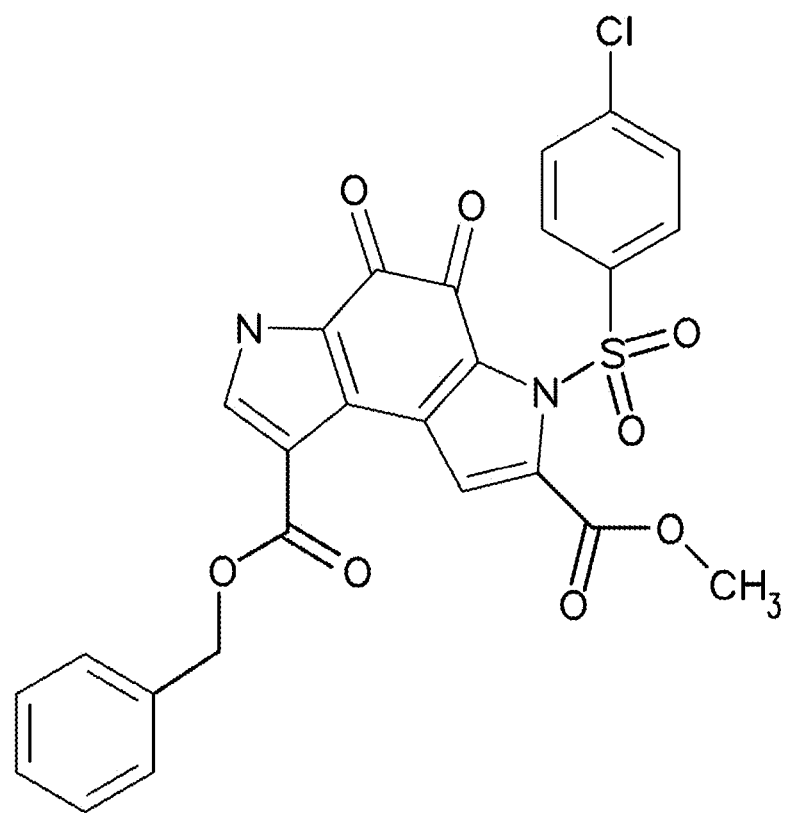
FIG. 2A is the chemical structure of compound 1.

C. for 24 h. The mixture was cooled to −78° C., and SnCl$_4$ (0.118 mL, 1.0 mmol) was added dropwise. After 1.5 h, the mixture was quenched by dropwise addition of water (4.0 mL). The CH$_2$Cl$_2$ layer was separated, and the aqueous phase was extracted with CH$_2$Cl$_2$ (3×10 mL). Combined organic phases were dried (Na$_2$SO$_4$) and evaporated under reduced pressure. The residue was then chromatographed on silica gel using CHCl$_3$/MeOH=25/1. Compound 5a was obtained with a yield of 67 mg, 12%. FIG. 2A shows the chemical structure of compound 5a (compound 1).

Synthesis of 1-(4-Fluorophenyl)methyl 7-methyl 6-(4-methylbenzenesulfonyl)-4,5-dioxo-3H,4H,5H, 6H-pyrrolo[3,2-e]indole-1,7-dicarboxylate (5b)

Figure 2B:
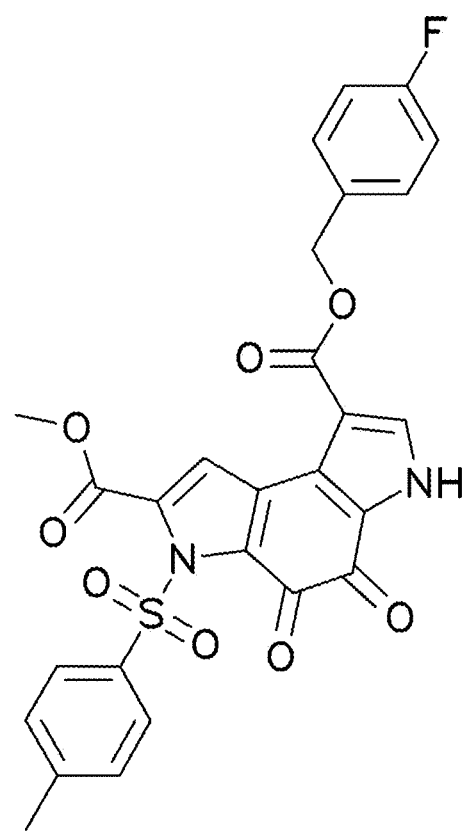
FIG. 2B is the chemical structure of compound 2.

The procedure for 4a was applied. Compound 5b was obtained with a yield of 61 mg, 8%. FIG. 2B shows the chemical structure of compound 5b (compound 2).

Analysis $^1$H NMR spectra were recorded at 400 MHz and $^{13}$C NMR spectra were recorded at 100 MHz at room temperature using CDCl$_3$ as a solvent. Chemical shifts were reported in ppm relative either to TMS as internal standard or to the residual solvent peak. The following abbreviations were used to describe spin multiplicity: s=singlet, d=doublet, t=triplet, q=quartet, m=multiplet, brs=broad singlet, dd=doublet of doublets. The LC/MS was recorded on Agilent 1100 with LC/MSD SLMobile Phase: A-H$_2$O+0.1% HCOOH; B-MeCN+0.1HCOOH.

Figure 3A:
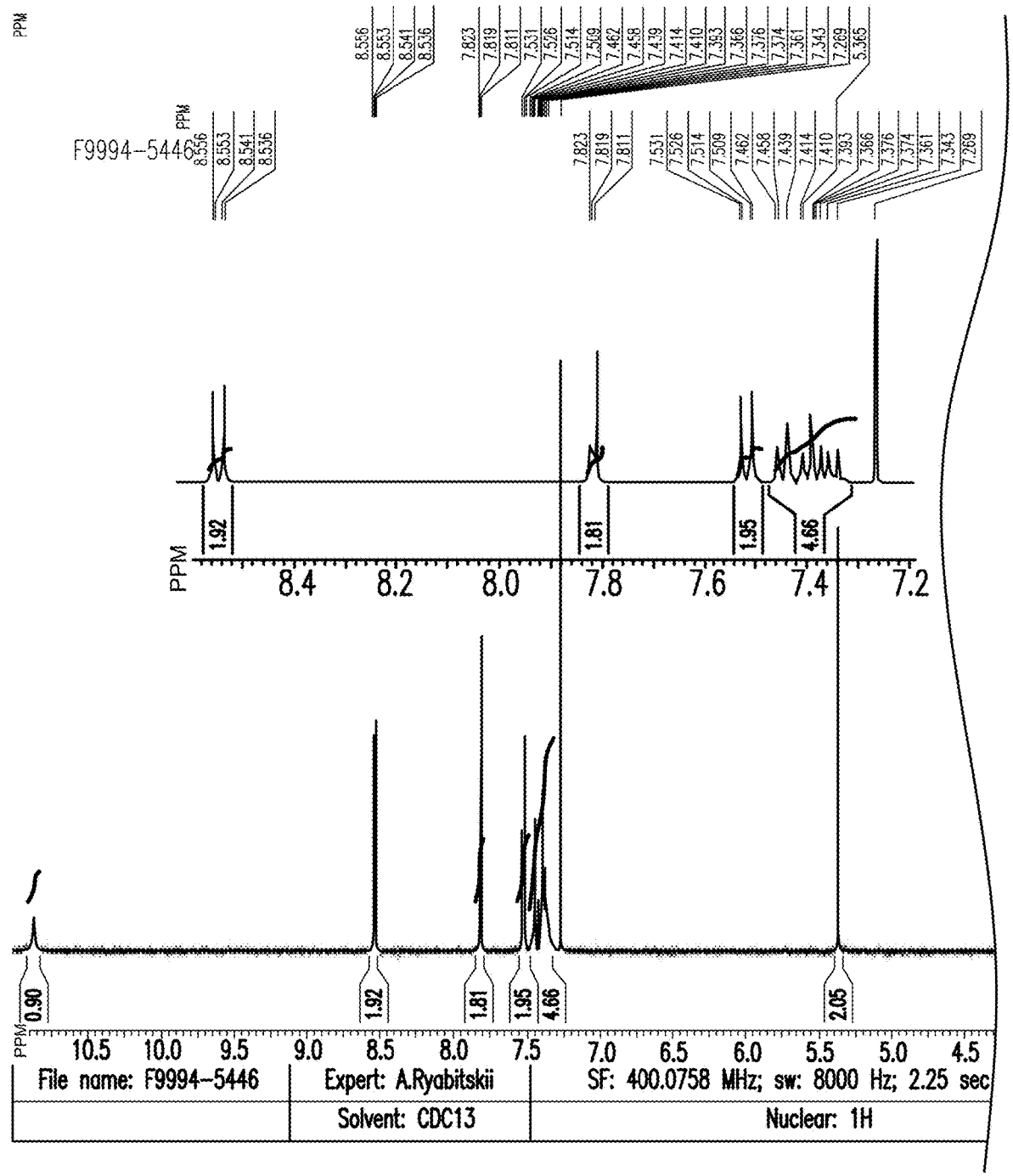
FIG. 3A is the $^1$H NMR spectra of compound 1.
Figure 3A:
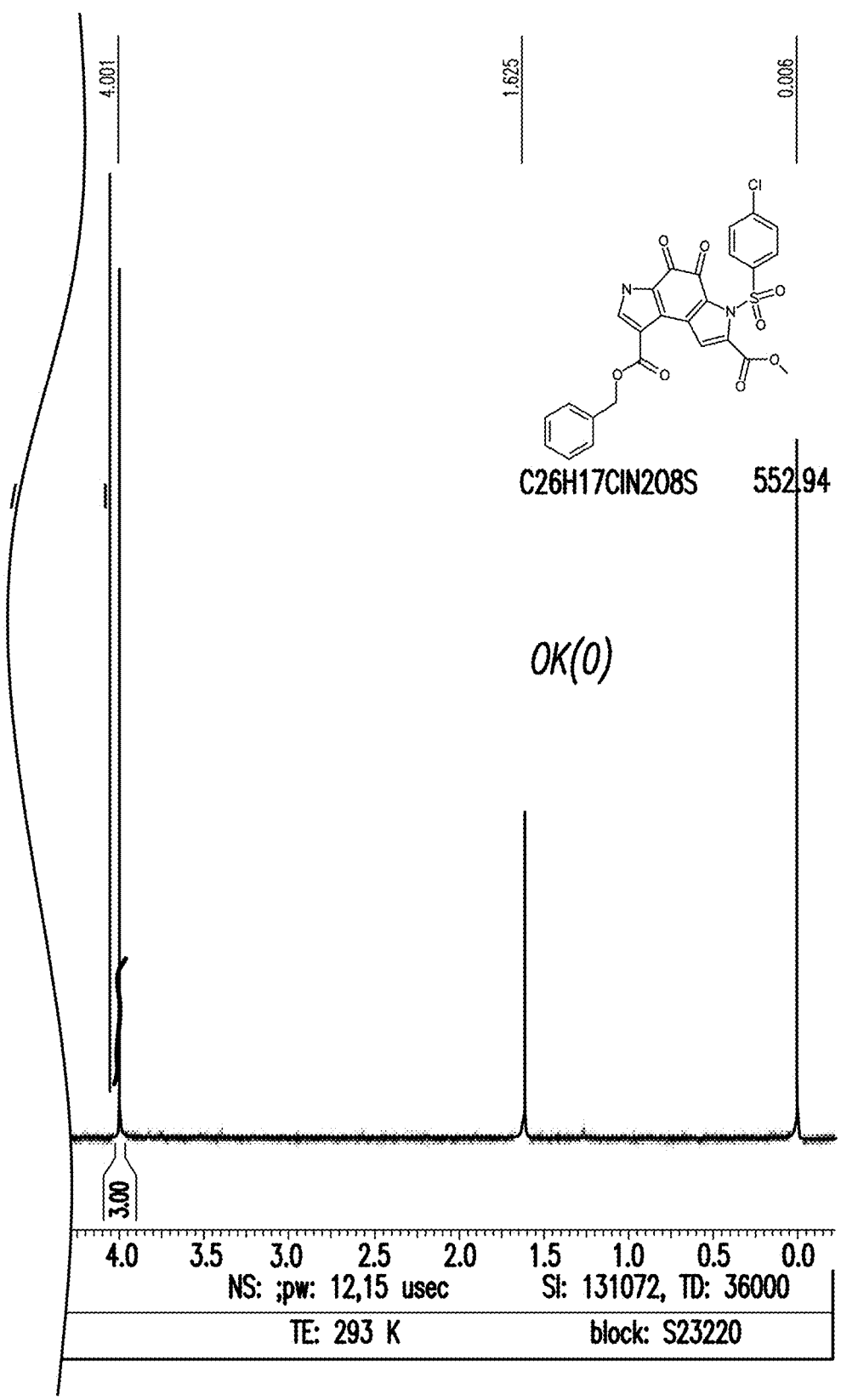
Figure 3B:
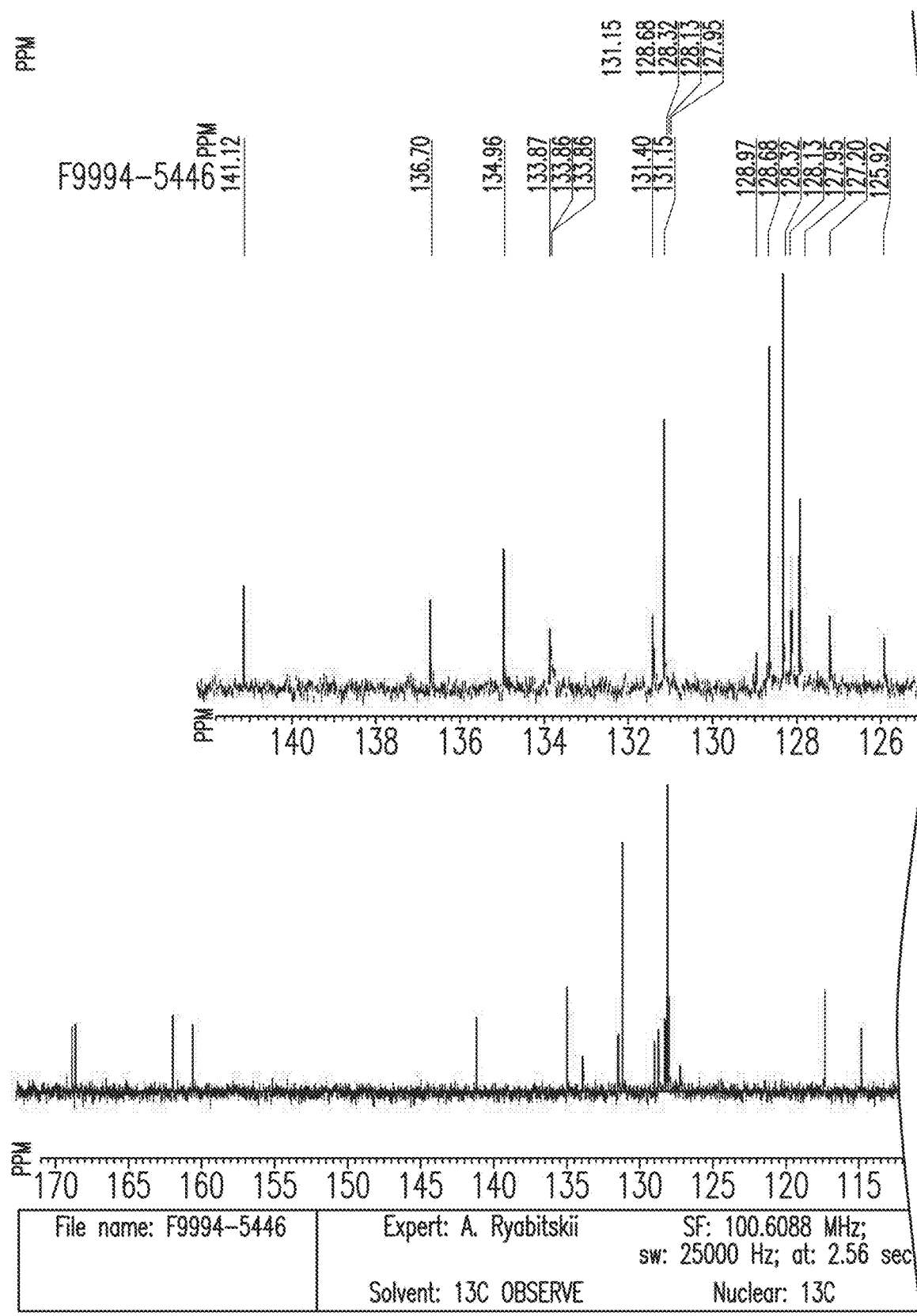
FIG. 3B is the $^{13}$C NMR spectra of compound 1.
Figure 3B:
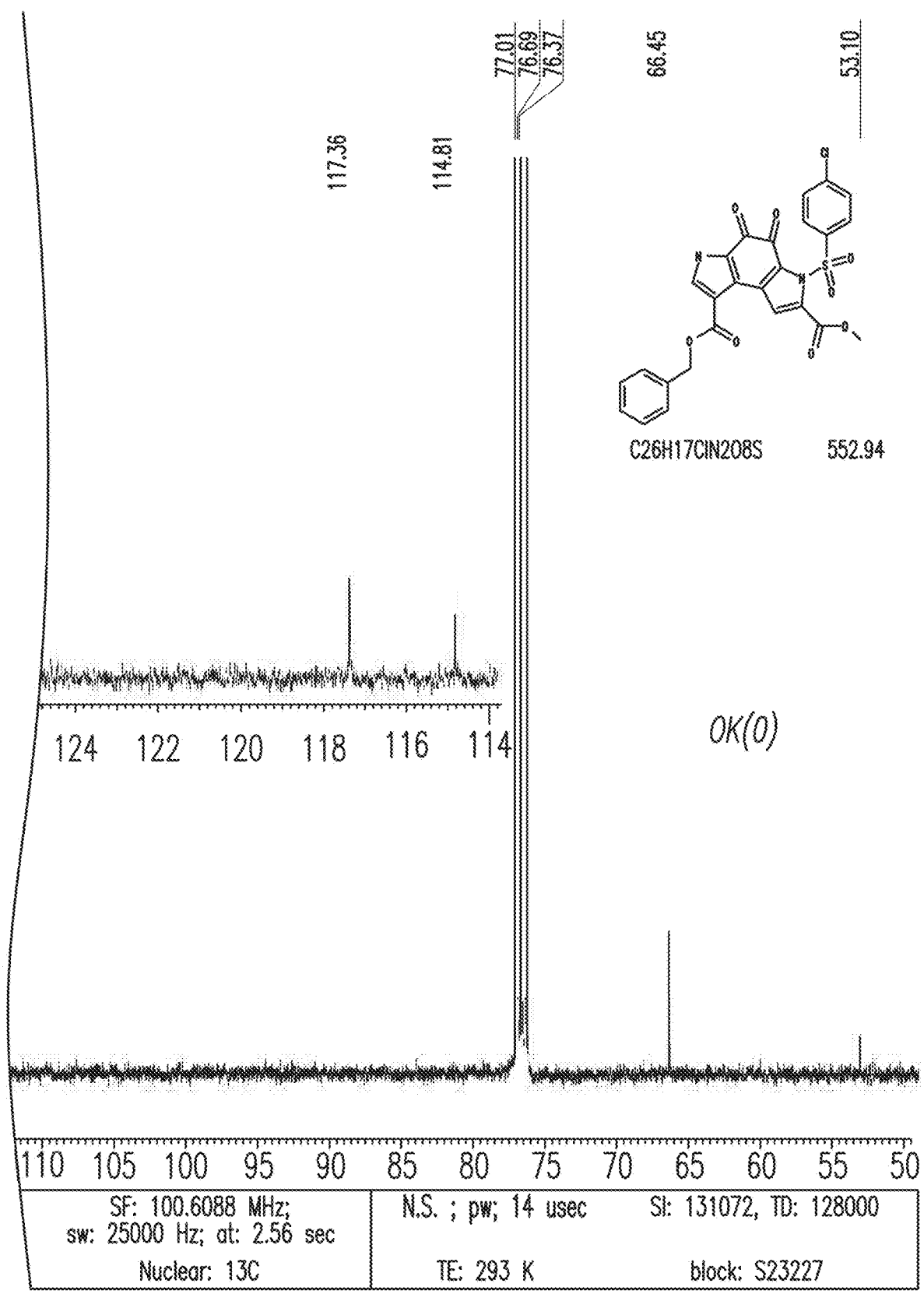

5a: 1-Benzyl 7-methyl 6-(4-chlorobenzenesulfonyl)-4,5-dioxo-3H,4H,5H,6H-pyrrolo[3,2-e]indole-1,7-dicarboxylate FIGS. 3A and 3B show the $^1$H NMR spectra and the $^{13}$C NMR spectra of compound 5a, respectively. Beige crystalline powder; m.p. 141-152° C.; $^1$H NMR (400 MHz, CDCl$_3$, δ) 11.05-11.02 (m, 1H), 8.56 (d, J=0.8 Hz, 1H), 8.54 (d, J=0.8 Hz, 1H), 7.82-7.81 (m, 2H), 7.53-7.51 (m, 2H), 7.45-7.30 (m, 5H), 5.37 (s, 2H), 4.00 (s, 3H); $^{13}$C NMR (100 MHz, CDCl$_3$, δ) 169.3, 169.2, 141.1, 136.7, 135.0, 133.9, 133.9, 133.9, 131.4, 131.2, 128.7, 128.3, 128.1, 128.0, 127.2, 125.9, 117.4, 114.8, 66.5, 53.1.

Figure 3C:
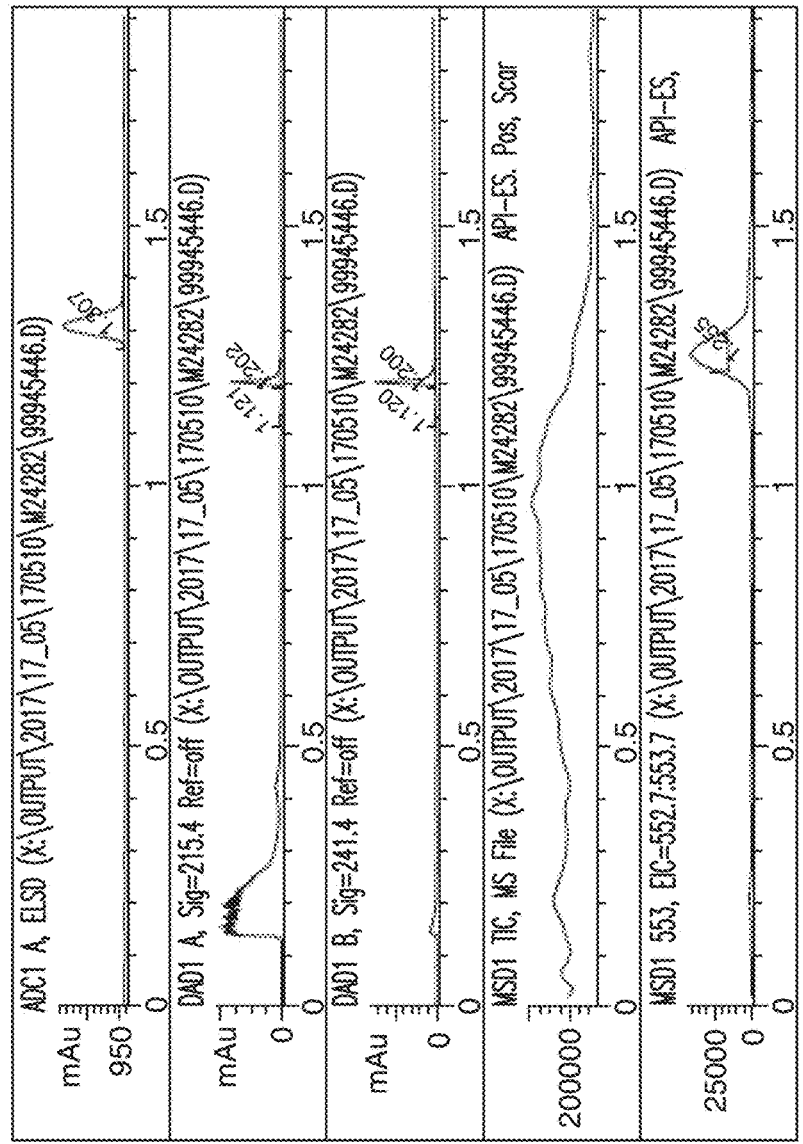
FIG. 3C is the LC/MS spectra of compound 1.
Figure 3C:
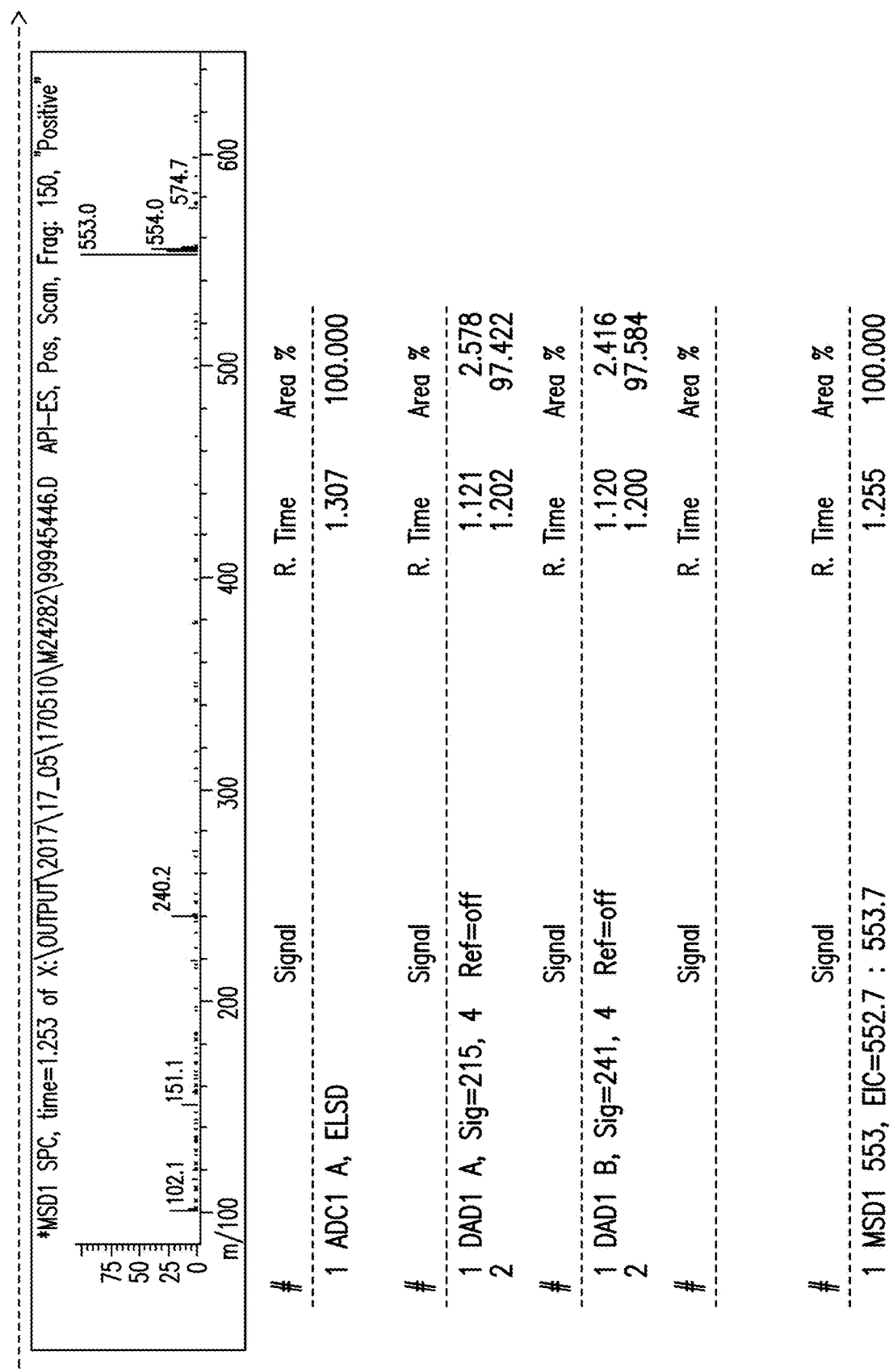

FIG. 3C shows the LC/MS spectra of compound 5a. LC/MS for C$_{26}$H$_{17}$ClN$_2$O$_8$S [M+H]$^+$ 552.95, found 553.0.

Figure 4A:
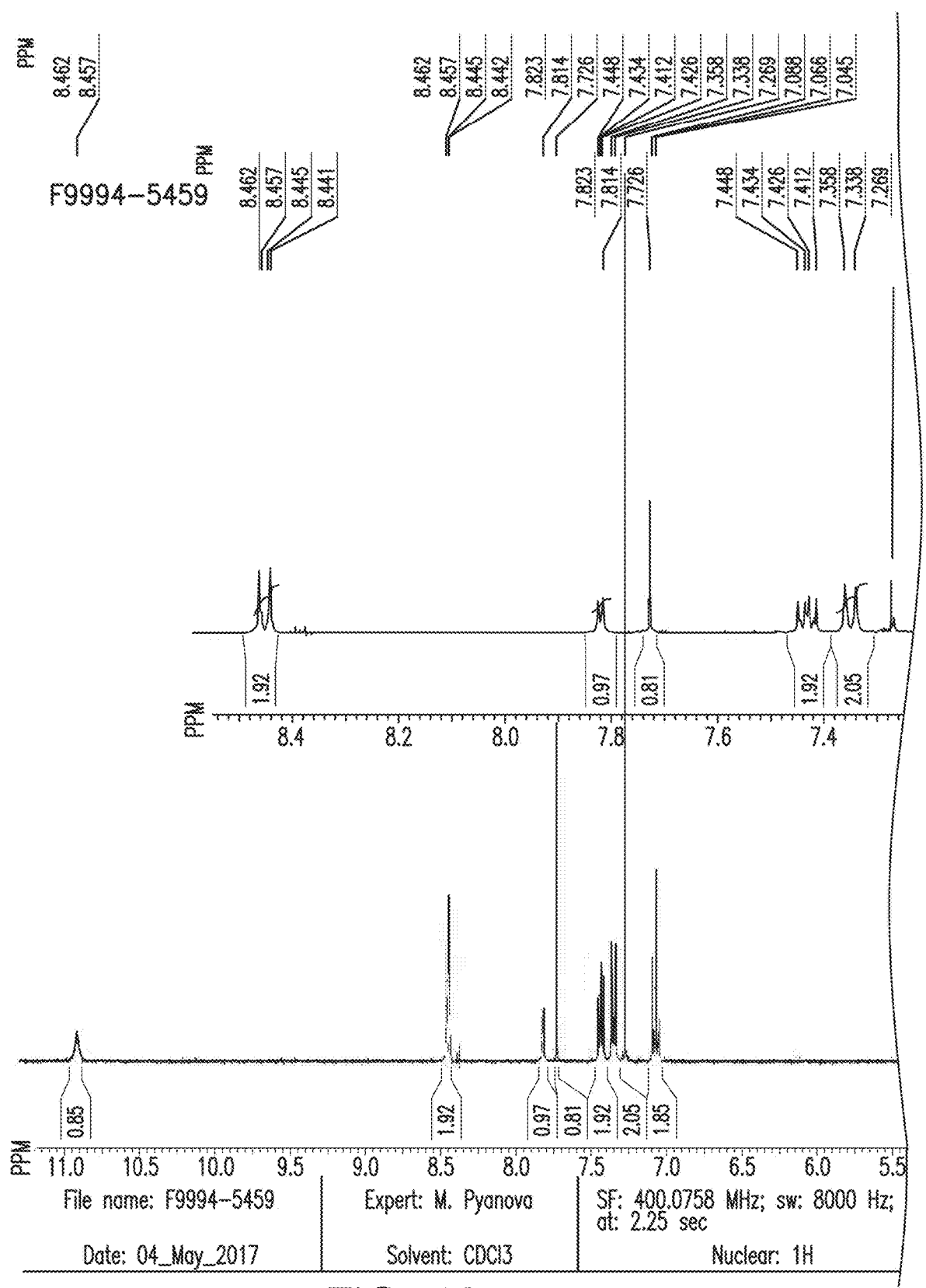
FIG. 4A is the $^1$H NMR spectra of compound 2.
Figure 4A:
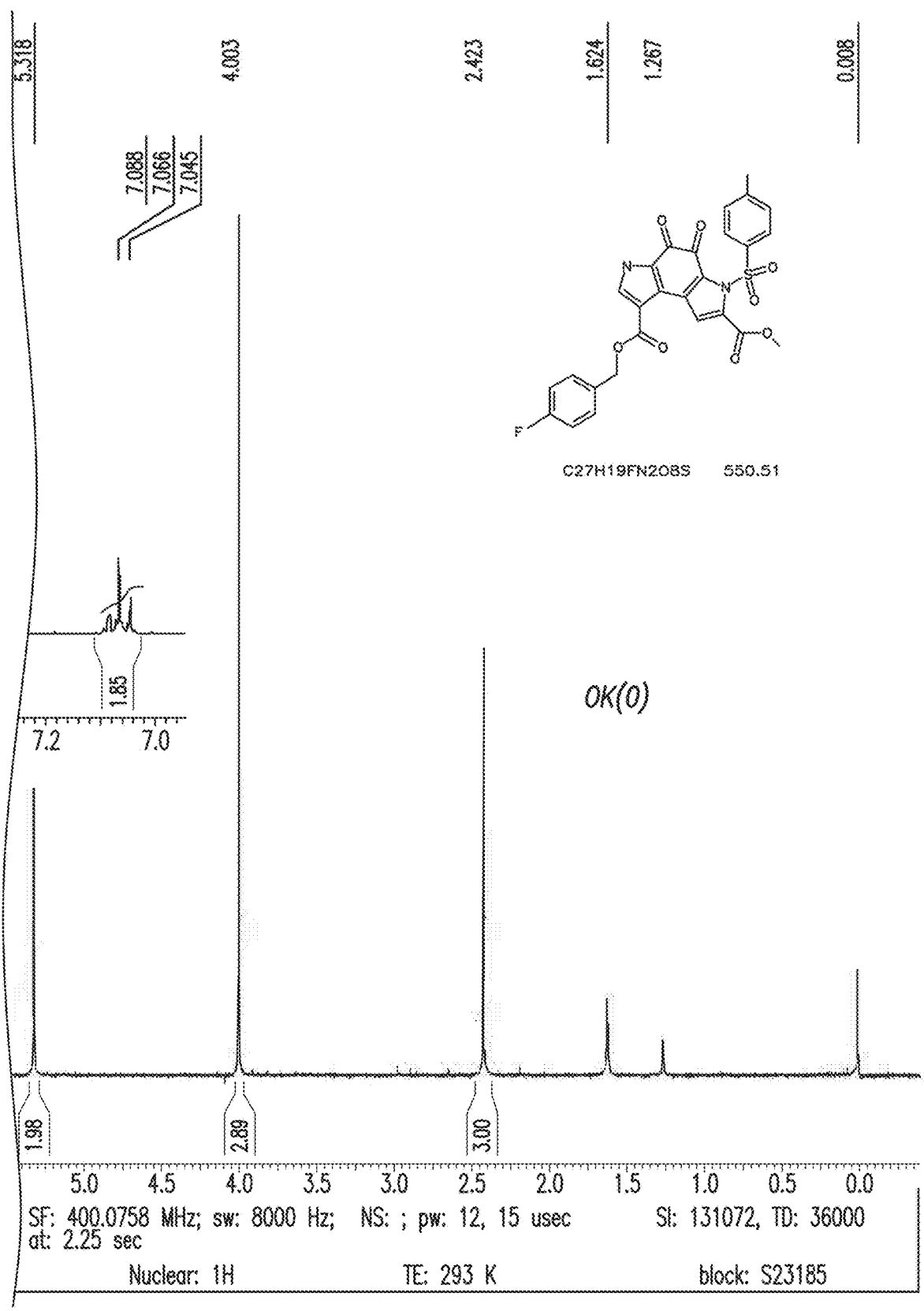
Figure 4B:
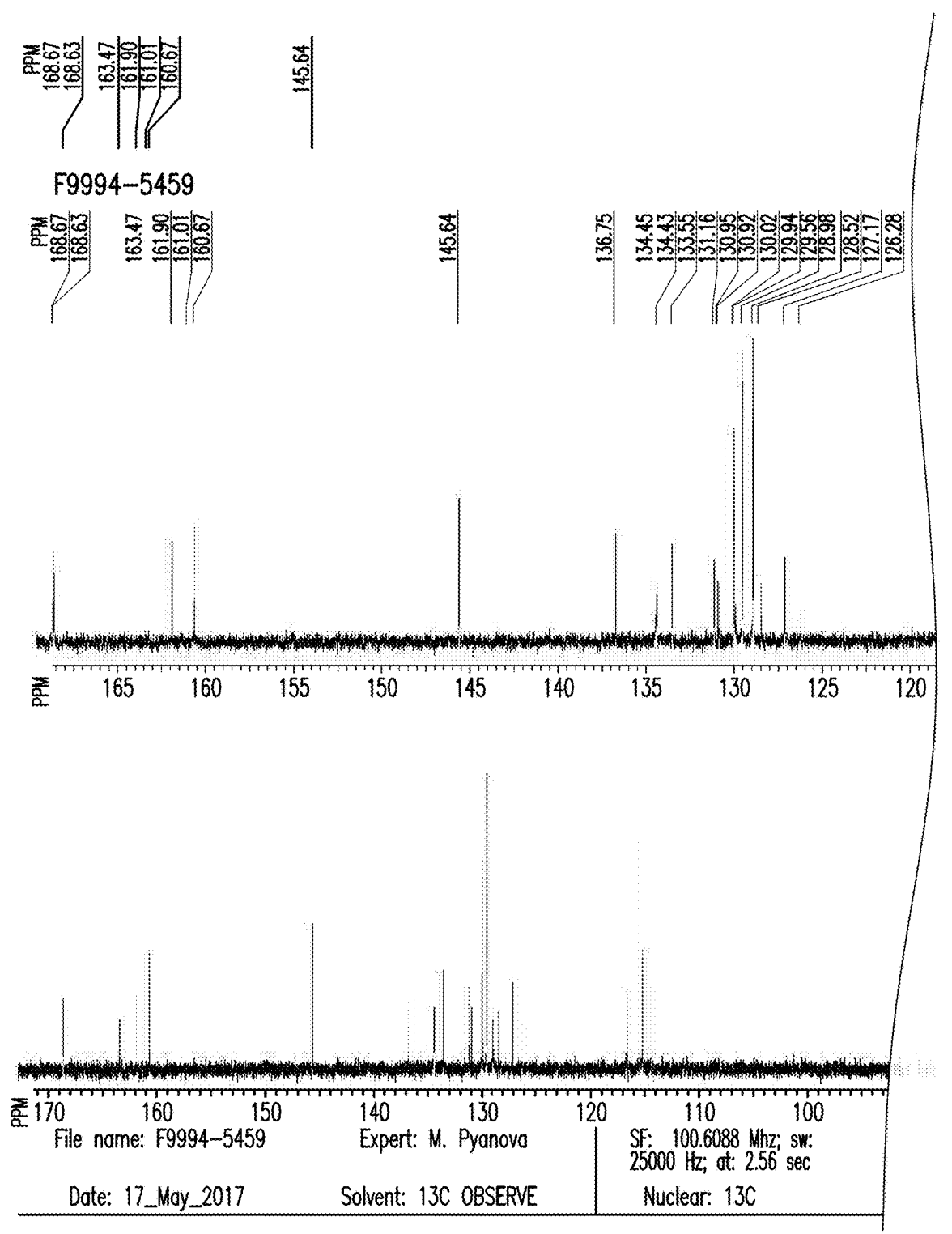
FIG. 4B is the $^{13}$C NMR spectra of compound 2.
Figure 4B:
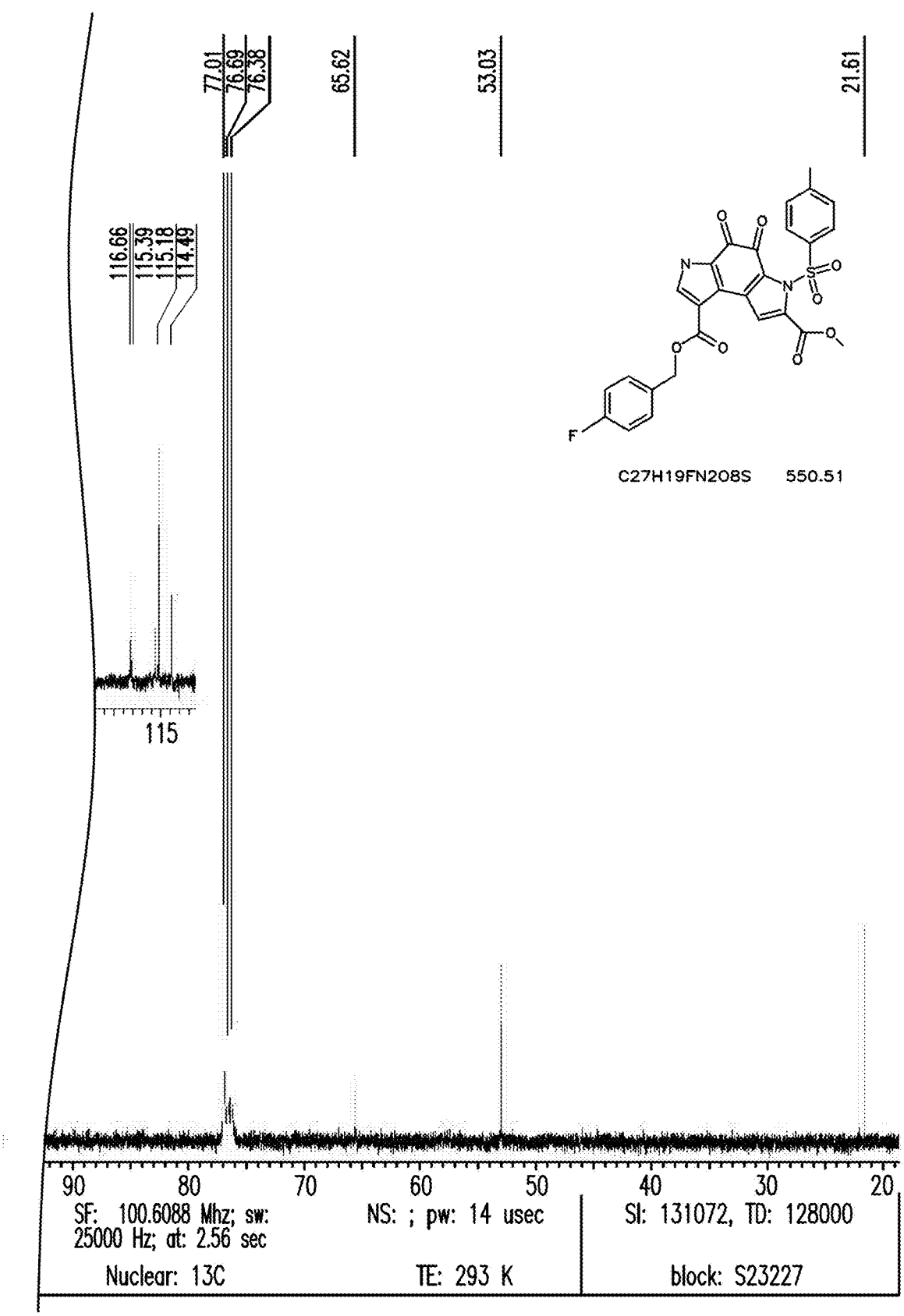

5b: 1-(4-Fluorophenyl)methyl 7-methyl 6-(4-methylbenzenesulfonyl)-4,5-dioxo-3H,4H,5H,6H-pyrrolo [3,2-e]indole-1,7-dicarboxylate FIGS. 4A and 4B show the $^1$H NMR spectra and the $^{13}$C NMR spectra of compound 5b, respectively. Red crystalline powder; m.p. 121.5-134.5° C.; $^1$H NMR (400 MHz, CDCl$_3$, δ) 10.92 (d, J=0.8 Hz, 1H) 8.46-8.44 (m, 2H), 7.82-7.81 (m, 1H), 7.44-7.42 (m, 1H), 7.45-7.34 (m, 2H), 7.36-7.29 (m, 2H), 7.09-7.05 (m, 2H) 5.32 (s, 2H), 4.00 (s, 3H), 2.42 (s, 3H); $^{13}$C NMR (100 MHz, CDCl$_3$, δ) 168.7, 168.6, 163.5, 161.9, 161.0, 160.7, 145.6, 136.8, 134.5, 134.4, 133.6, 131.2, 131.0, 130.9, 129.9, 129.0, 128.5, 127.2, 126.3, 116.7, 115.4, 115.2, 114.5, 65.6, 53.0, 21.6.

Figure 4C:
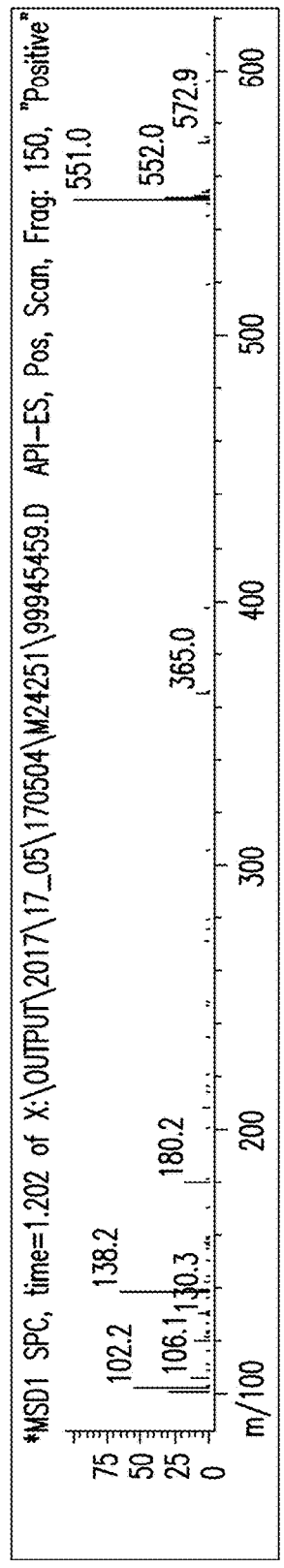
FIG. 4C is the LC/MS spectra of compound 2.

FIG. 4C shows the LC/MS spectra of compound 5b. LC/MS for C$_{27}$H$_{19}$FN$_2$O$_8$S [M+H]$^+$550.52, found 551.0.

Example 2: Cytotoxic T Lymphocyte (CTL) Tumor-Infiltration Levels in MSS and MSI Human Colon Carcinoma Materials and Methods Human MSS and MSI colon carcinoma specimens were analyzed by immunohistochemical staining of CD8 T cells.

Results

Figure 5:
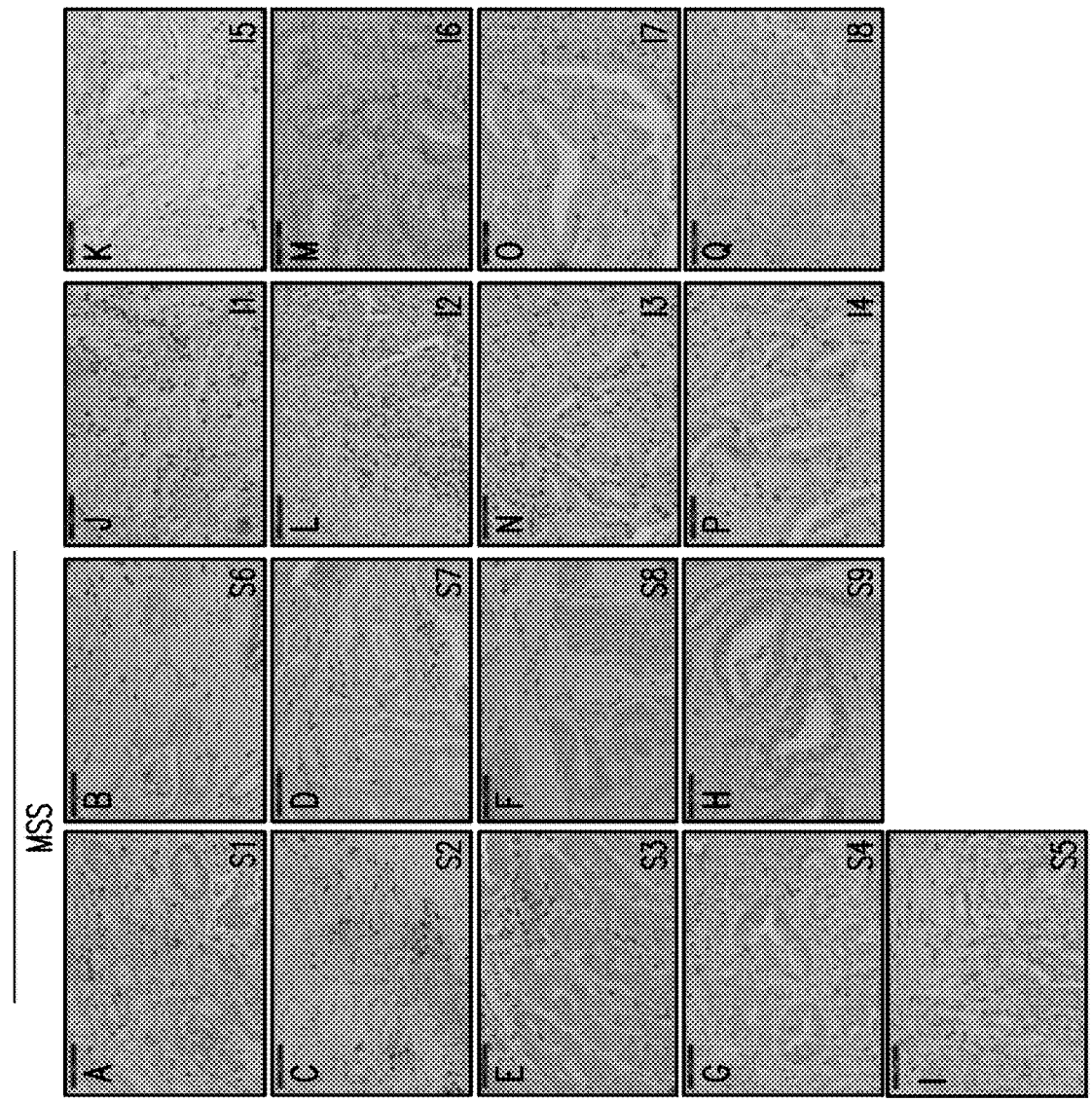
FIG. 5 shows immunohistochemical staining of CD8 T cells in human MSS and MSI colon carcinoma.
Figure 6:
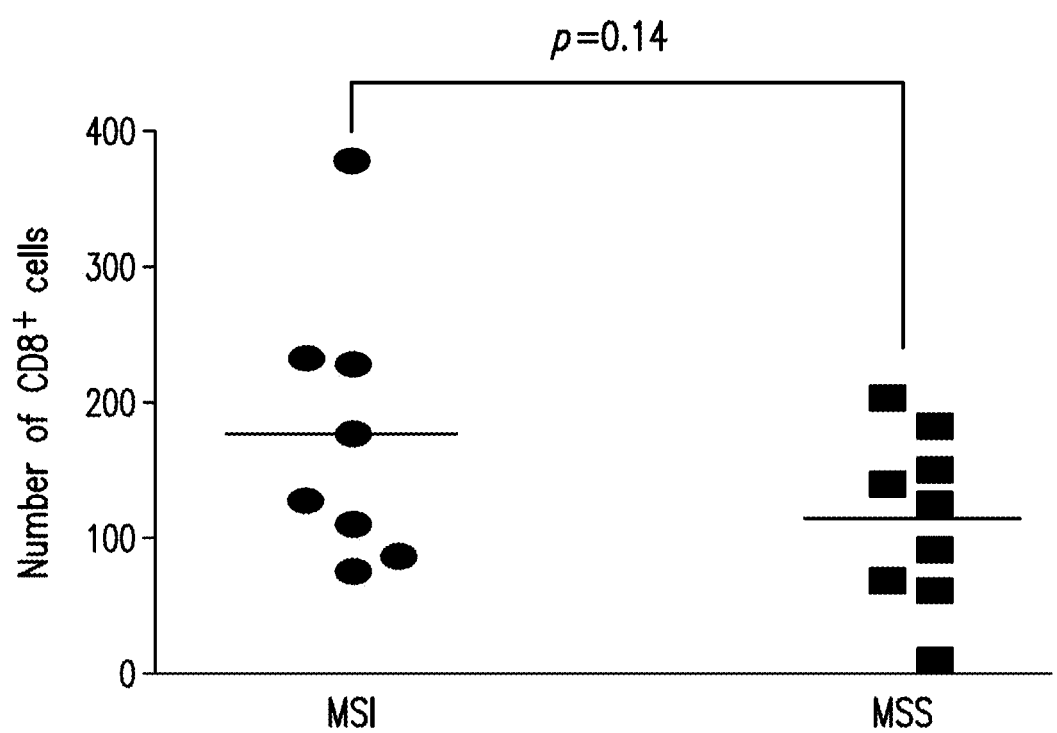
FIG. 6 is a graph that shows CTL tumor infiltration levels in human MSI and MSS colon carcinoma specimens. The X-axis represents the specimen type and the Y-axis represents number of CD8+ cells. Each dot represents number of CD8+ CTLs in one view area of a tumor specimen.

Human MSS and MSI colon carcinoma specimens were analyzed by immunohistochemical staining of CD8 T cells. As expected, all eight MSI colon carcinoma specimens exhibited medium to high levels of tumor-infiltrating CTLs (FIG. 5). However, eight of the nine MSS colon carcinoma specimens also exhibited medium levels of tumor-infiltrating CTLs. No statistically significant difference in CTL tumor infiltration levels was observed between MSI and MSS colon carcinoma specimens (FIG. 6).

Example 3: Fas and SUV39H1 mRNA Levels in Normal Human Colon and Human Colorectal Carcinoma Materials and Methods Numerous samples of normal human colon tissues and colon carcinoma tissues in the NCI TCGA database were analyzed for Fas and SUV39H1 mRNA levels.

Results

Figure 7A:
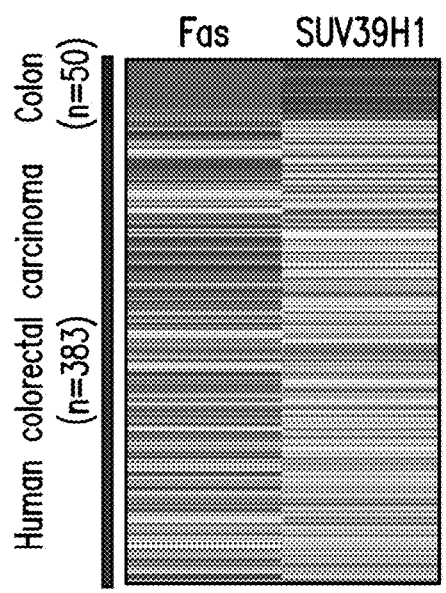
FIG. 7A is a heat map showing the Fas and SUV39H1 mRNA levels present in normal human colon tissue and colon carcinoma tissue samples. Red bars represent up-regulation and blue bars indicate down-regulation.

The TCGA database was screened for altered gene expression between human colon carcinoma and normal colon tissues (FIG. 7A). SUV39H1, which is an H3K9me3-specific histone methyltransferase, was significantly elevated in the tumor tissue (FIG. 7B).

Figure 7B:
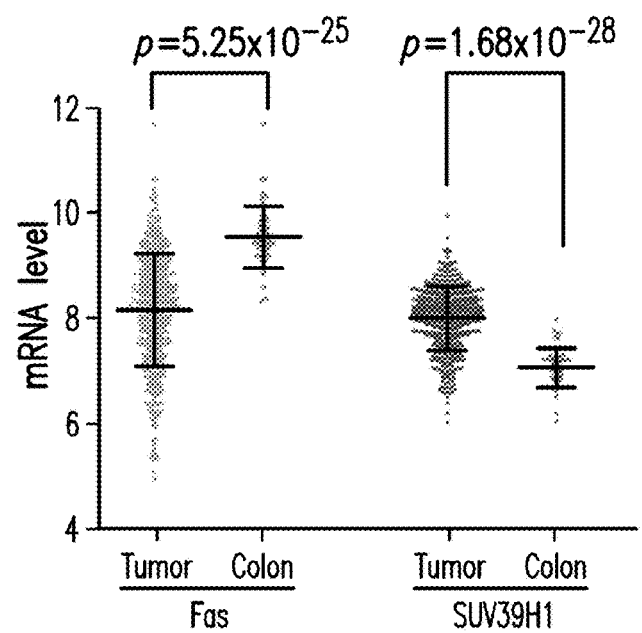
FIG. 7B is a dot plot comparing the SUV39H1 mRNA levels from normal colon tissue and colon carcinoma tissue.

Analysis of the samples of normal human colon tissues and colon carcinoma tissues revealed that the expression levels of SUV39H1 were significantly higher in human colon carcinomas than in normal colon tissues, whereas the expression level of Fas was significantly lower in human colon carcinoma tissues than in normal colon tissues (FIG. 7B).

Example 4: SUV39H1 mRNA Levels in Tumor Cells and Tumor-Infiltrating CTLs in MC38 Mouse Colon Carcinoma Materials and Methods CD45$^-$ tumor cells and CD8$^+$ CTLs were isolated from fresh MC38 tumor tissues in C$_{57}$BL/6 mice. mRNA analysis to determine levels of SUV39H1 was performed.

Figure 7C:
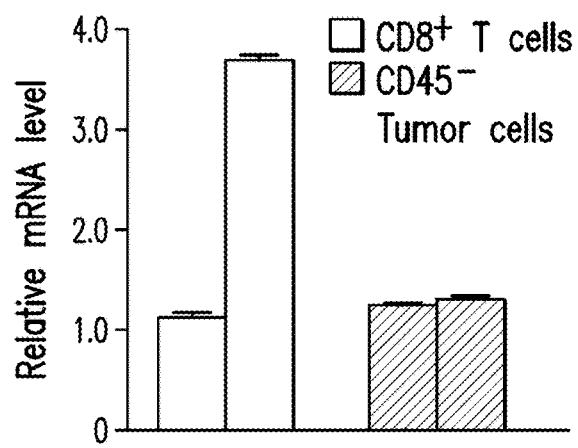
FIG. 7C is a bar graph showing SUV39H1 mRNA levels in CD8$^+$ T cells and CD45 tumor cells. The white bars represent SUV39H1 mRNA levels in CD8$^+$ tumor infiltrating CTLs from two tumor bearing mice. The hatched bars represent SUV39H1 mRNA levels of CD45-depleted tumor cells from two tumor bearing mice. The Y-axis represents relative mRNA level.
Figure 7D:
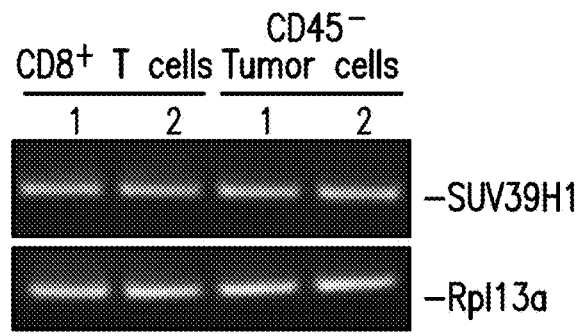
FIG. 7D is an agarose gel showing SUV39H1 DNA fragments in CD8$^+$ T cells and CD45$^-$ T cells. Rp113a was used as a normalization control.
Figure 8A:
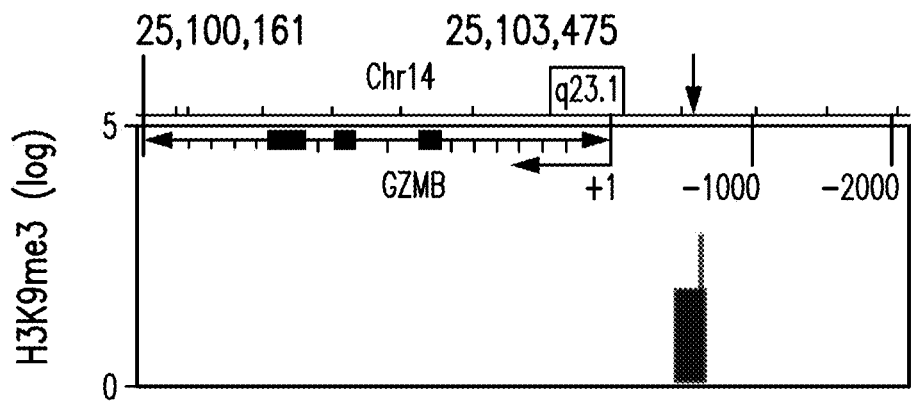
FIG. 8 shows H3K9me3 expression levels in four human T-cell promoter regions, GZMB (FIG. 8A), PRF1 (FIG. 8B), FASLG (FIG. 8C), and IFNG (FIG. 8D). The H3K9me3 peaks are presented as green bars. The H3K9me3 peaks in gene promoter regions are indicated by red arrows.
Figure 8B:
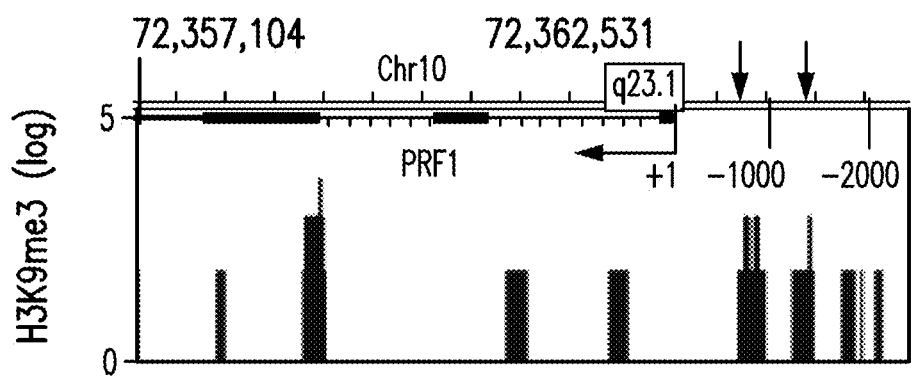
Figure 8C:
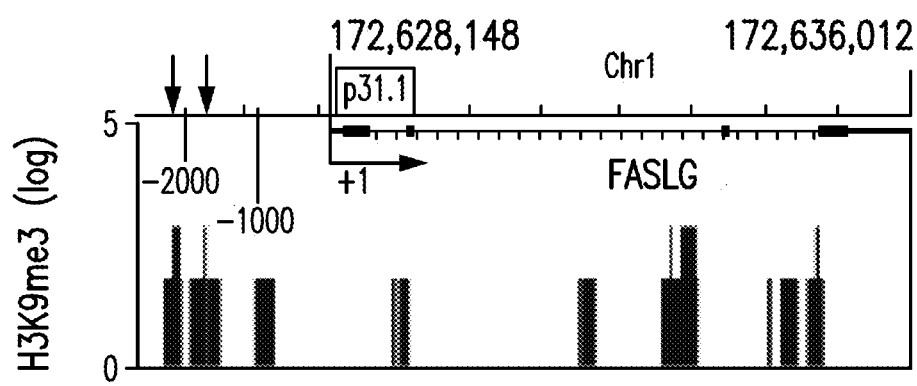
Figure 8D:
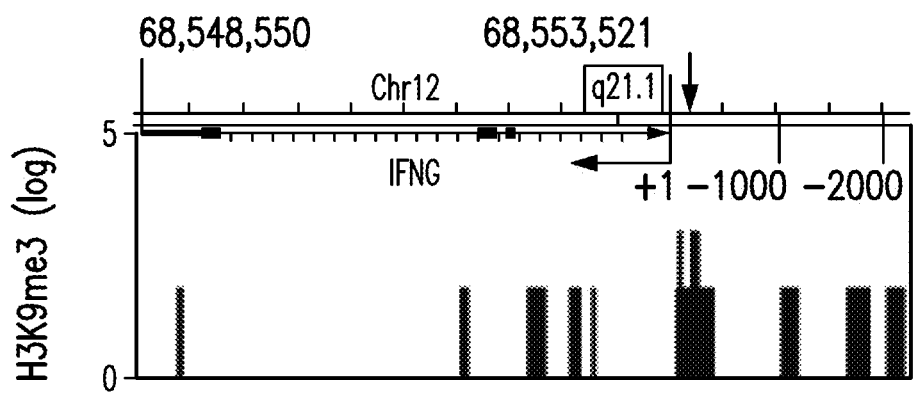

Results:

FIG. 7C-D show that SUV39H1 is highly expressed in both tumor-infiltrating CTLs and CD45$^-$ tumor cells in mouse colon carcinoma models.

Example 5: Enriched H3K9me3 in Promoter Regions of Effectors in Quiescent T Cells Materials and Methods:

Analysis of H3K9me ChIP-seq data in the Gene Expression Omnibus (GEO) Database (accession # GSM1058783) was performed to determine the levels of H3K9me3 enrichment in the promoter regions of GZMB, PRF1, FASLG and IFNG in human T cells. Analogously, mouse T cells from C57BL/6 were isolated from mouse spleens and ChIP analysis was performed using H3K9me3-specific antibody.

Results:

FIG. 8 shows that H3K9me3 levels were enriched in the promoter regions of GZMB (FIG. 8A), PRF1 (FIG. 8B), FASLG (FIG. 8C) and IFNG (FIG. 8D) in human T cells. The H3K9me3 peaks in gene promoter regions are indicated by red arrows.

FIG. 9 shows that H3K9me3 was also enriched in the promoter regions of GZMB (FIG. 9B), PRF1 (FIG. 9D), FASLG (FIG. 9F) and IFNG (FIG. 9H) in resting mouse T cells.

These observations indicate that expression of T cell effectors was silenced by H3K9me3-mediated epigenetic mechanism in resting T cells.

Example 6: Determination of EC50 of Compound 1 ("F5446")

Materials and Methods

F5446 was sent to Reaction Biology Corp. (Malvern Pa.) to validate its inhibitory activity and to determine its $EC_{50}$ for SUV39H1. F5446 was assayed in a 10-dose $EC_{50}$ mode with 3-fold serial dilutions using recombinant human SUV39H1 protein as the methyltransferase, S-(methyl-3H) Adenosyl-L-Methionine as the substrate, and H3 peptide (N1-21) as the template in the presence of indicated doses of F5446. The $EC_{50}$ was calculated with Prizm Program.

Results

Figure 10:
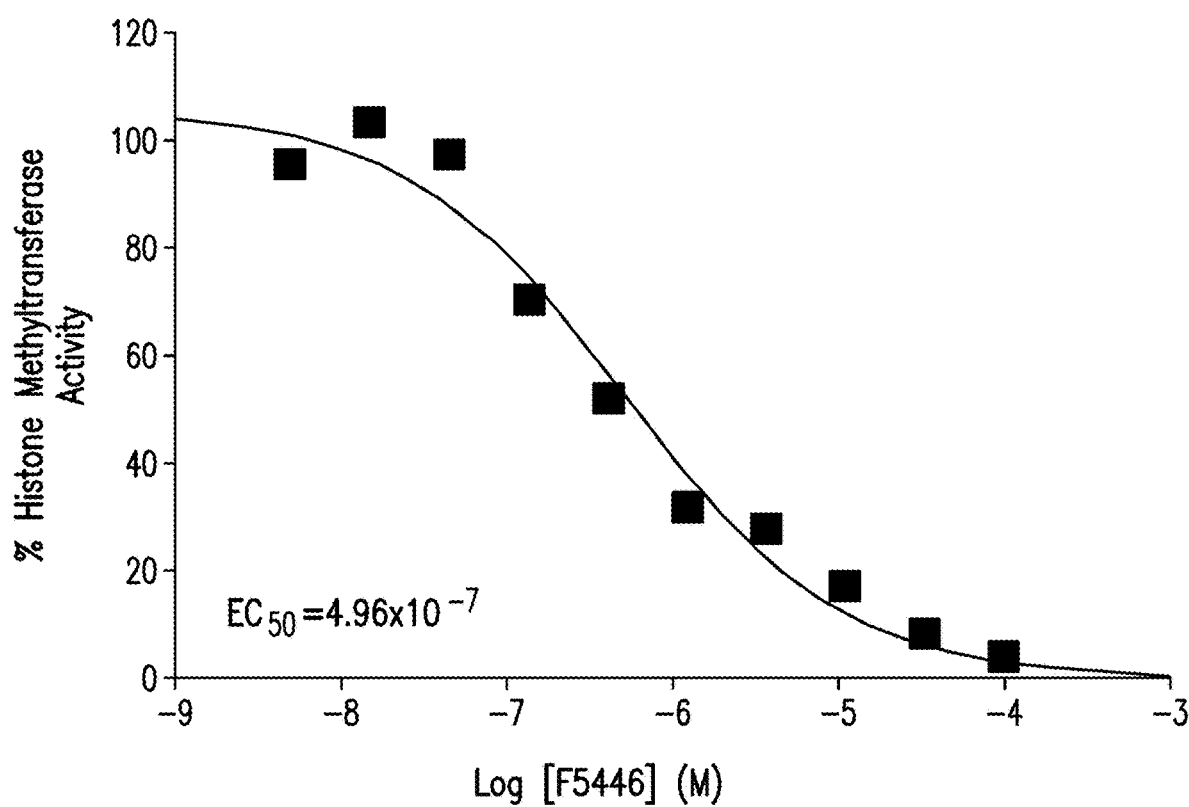
FIG. 10 is a line graph showing the EC$_{50}$ of compound 1 against recombinant human SUV39H1 in vitro. The X-axis represents concentration of compound 1 and the Y-axis represents percent histone methyltransferase activity.

As shown in FIG. 10, the F5446 compound has an EC50 of $4.96 \times 10^{-7}$ M against recombinant human SUV39H1 in vitro.

Example 7: F5446 Induces Human Colon Carcinoma Cell Apoptosis

Materials and Methods

Figure 13A:
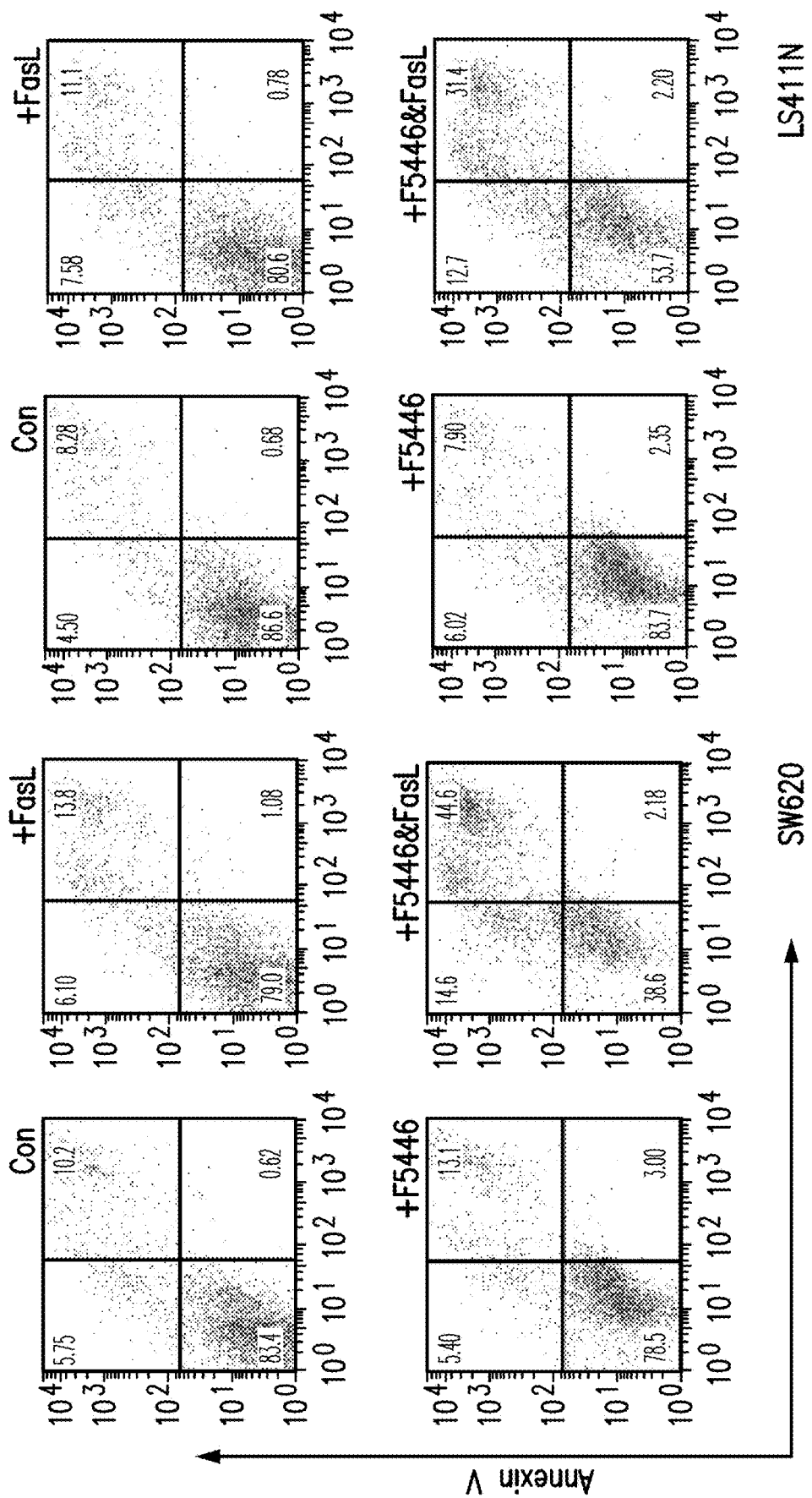
FIG. 13A shows flow cytometry plots analyzing cells cultured in the presence of compound 1 and/or FasL.

SW620 and LS411N cells were cultured in the presence of F5446 at doses of 0.01, 0.05, 0.25, and 1 μM for 2 days. Cells were stained with propidium iodide ("PI") and annexin V and analyzed for apoptosis by flow cytometry. FIG. 13A shows representative flow cytometry plots.

Results

Figure 11:
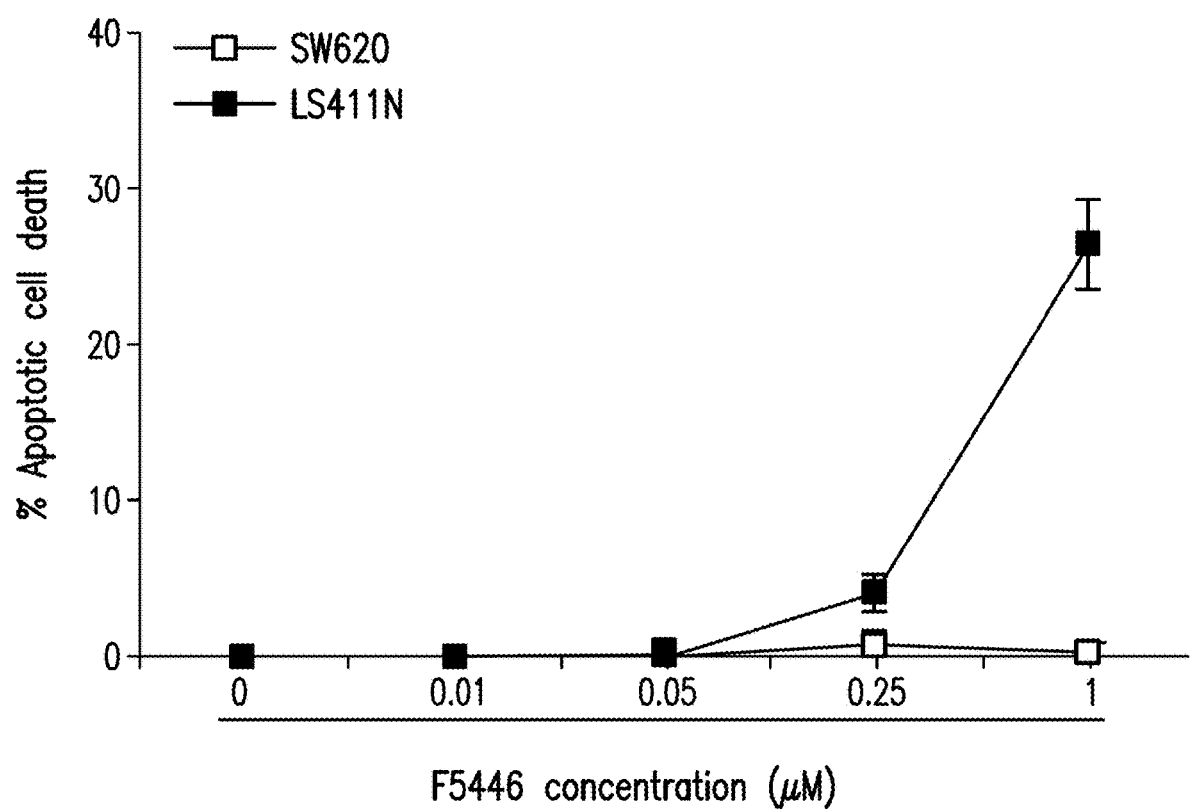
FIG. 11 is a line graph showing the percentage of apoptotic cell death at various concentrations of compound 1 for SW620 cells (□) and LS411N cells (■). The X-axis represent concentration of compound 1 (μM) and the Y-axis represents percent apoptotic cell death.

F5446 induced human colon carcinoma cell death in a dose-dependent manner. FIG. 11 shows the percentage of apoptotic cell death for the SW620 and LS411N cells at various concentrations of F5446. Apoptotic cell death was calculated as the difference between the percentage of $PI^+$ Annexin $V^+$ cells in the presence of F5446 and the percentage of $PI^+$ Annexin $V^+$ cells in the absence of F5446.

Example 8: F5446 Increases Fas Expression in Tumor Cells

Materials and Methods

Figures 12A, 12B:
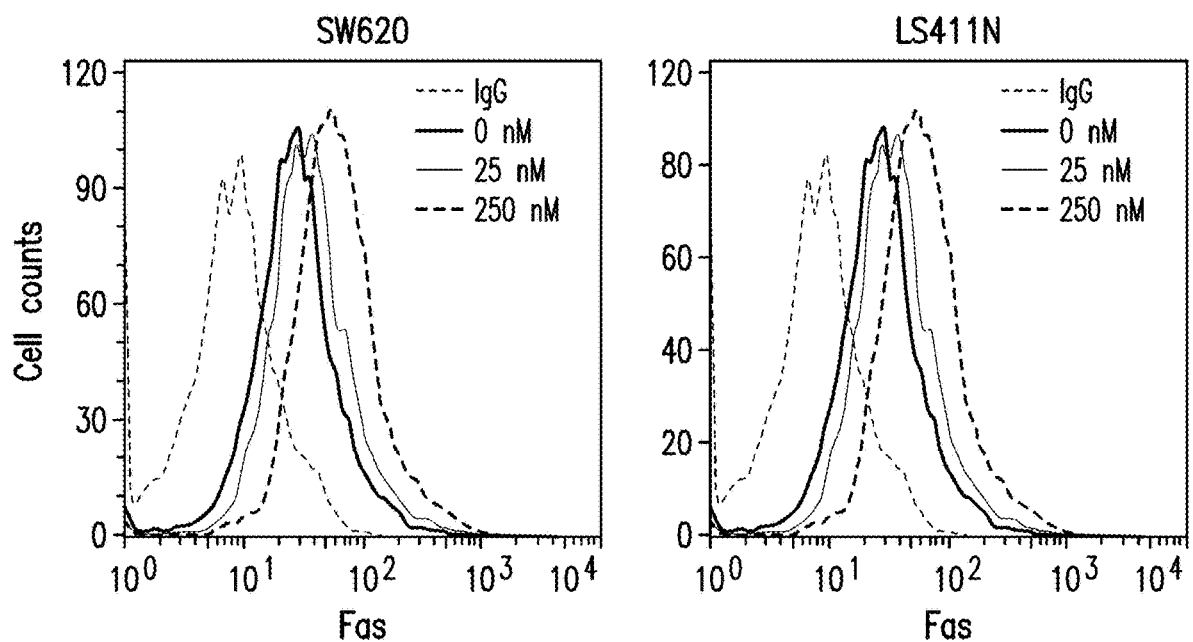
FIGS. 12A-12B show flow cytometry graphs analyzing Fas protein levels in SW620 cells (FIG. 12A) and LS411N cells (FIG. 12B).

SW620 and LS411N cells were cultured in the presence of F5446 for 3 days. Fas protein levels were analyzed by flow cytometry (FIG. 12A-12B).

Results

Figure 12C:
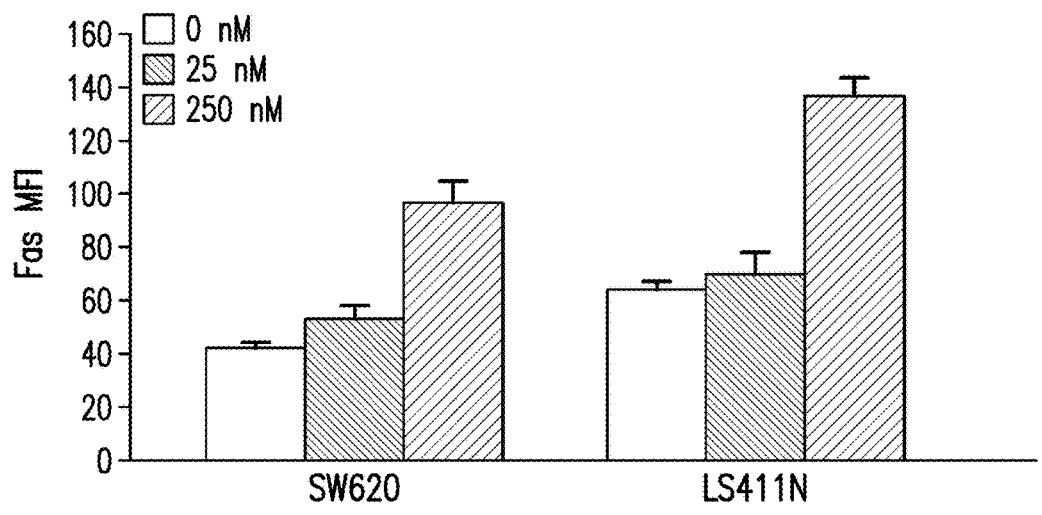
FIG. 12C is a bar graph showing the MFI of Fas in SW620 and LS411N cells at 0 nM (white bar), 25 nM (thin hatched bar), and 250 nM (wide hatched bar) of compound 1.

The F5446 compound up-regulated tumor cell surface Fas expression. The MFI of Fas was quantified and is shown in FIG. 12C.

Example 9: F5446 Overcomes Human Colon Carcinoma Cell Resistance to FasL-Induced Apoptosis Materials and Methods SW620 and LS411N cells were cultured in the presence of F5446 and FasL, either alone or in combination, for 3 days. Cells were stained with PI and Annexin V and analyzed for apoptosis. FIG. 13A shows representative images of flow cytometry plots.

Results

Figure 13B:
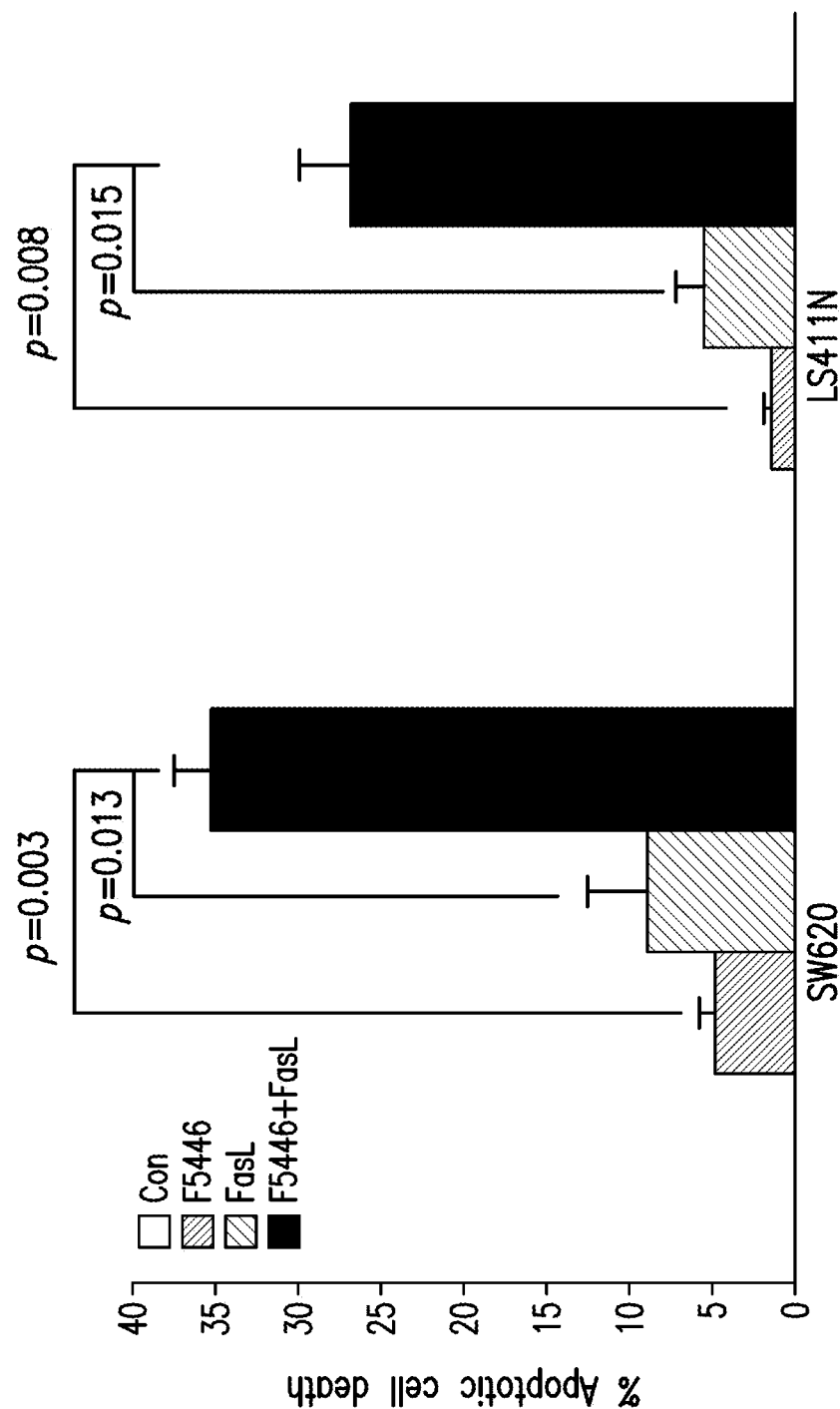
FIG. 13B is a bar graph showing the percentage of apoptotic cell death in SW620 and LS411N cells untreated (white bar), treated with compound 1 (thin hatched bar), treated with FasL (wide hatched bar), or treated with both compound 1 and FasL (black bar).

The F5446 compound significantly increased human colon carcinoma cells to FasL-induced apoptosis when used at a sublethal dose. FIG. 13B shows the percentage of apoptotic cell death. Apoptotic cell death was calculated as the difference between the percentage of $PI^+$ Annexin $V^+$ cells in the presence of F5446, FasL, or both and the percentage of $PI^+$ Annexin V+ cells in the absence of F5446 or FasL.

Example 10: Toxicity of F5446

Materials and Methods

F5446 was injected into mice at a dose of 10 mg/kg body weight every 2 days for 6 days. Mouse survival was recorded. Serum was collected from the mice and analyzed for liver enzyme profiles at the University of Georgia Veterinary Diagnostic Laboratories.

Results

Figure 14:
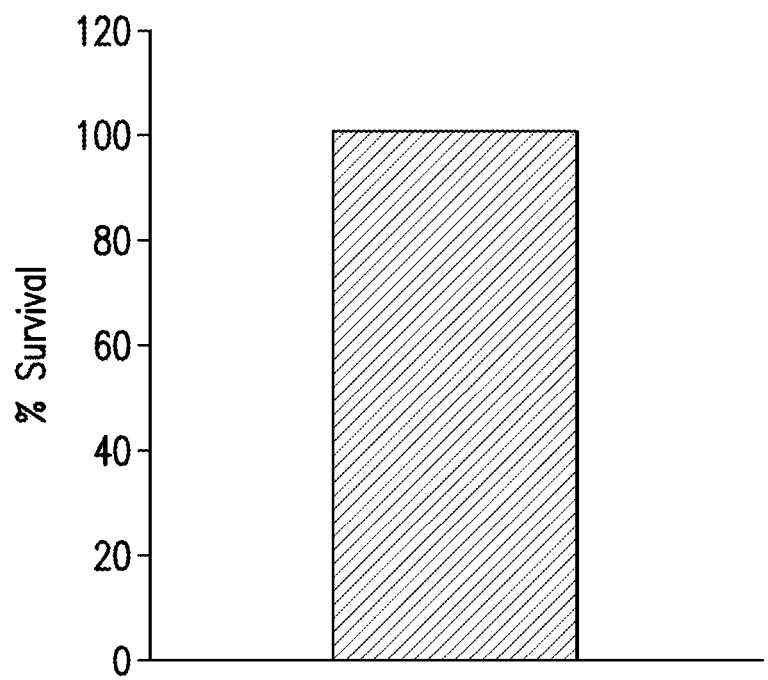
FIG. 14 is a bar graph showing the percentage of mouse survival after treatment with compound 1.

FIG. 14 shows the survival rate of the mice in the present toxicity study. Mice had a 100% survival rate at a F5446 dose as high as 10 mg/kg body weight (FIG. 14). The liver enzyme profile in the F5446-treated mice is shown below in Table 1.

TABLE 1

| LIVER ENZYME PROFILE IN F5446-TREATED MICE | | |
|---|---|---|
| Protein/Enzyme | Control | F5446 |
| ALP (U/L) | 98.3 | 60.3 |
| ALT (U/L) | 68.5 | 71.3 |
| AST (U/L) | 206 | 444.3 |
| GGT (U/L) | <3 | <3 |
| Cholesterol (mg/dl) | 131.3 | 119 |
| Total Bilirubin (mg/dl) | 0.1 | 0.1 |
| Total protein (g/dl) | 5.4 | 5.7 |
| Albumin (g/dl) | 3.6 | 3.3 |

The liver enzyme profile analysis revealed that F5446 did not cause toxic levels of liver enzymes in vivo.

Example 11: F5446 Inhibits H3K9me3 at the FAS Promoter Region in Human Colon Carcinoma Cells Materials and Methods SW620 and LS411N cells were treated with F5446 at 25, and 250 nM for 2 days and analyzed by ChIP using H3K9me3-specific antibody. The H3K9me3 antibody-immunoprecipitated DNA was amplified by PCR with FAS promoter DNA-specific primers and normalized to input genomic DNA.

Results

Figure 15A:
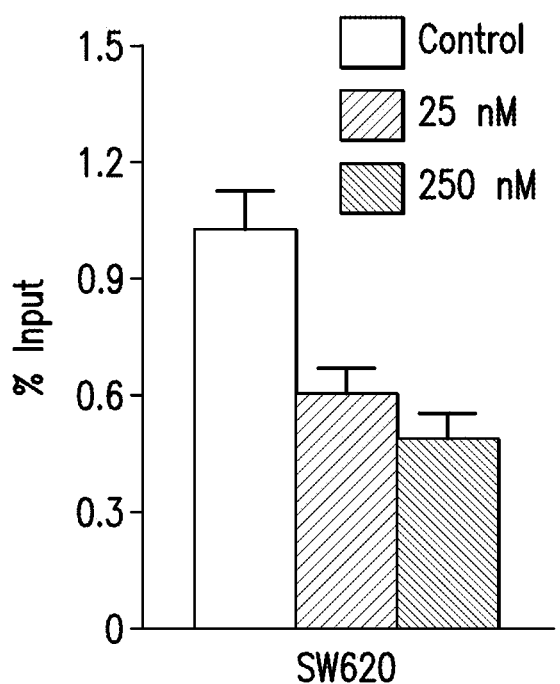
FIGS. 15A-15B are bar graphs showing the inhibition of H3K9me3 by compound 1.
Figure 15B:
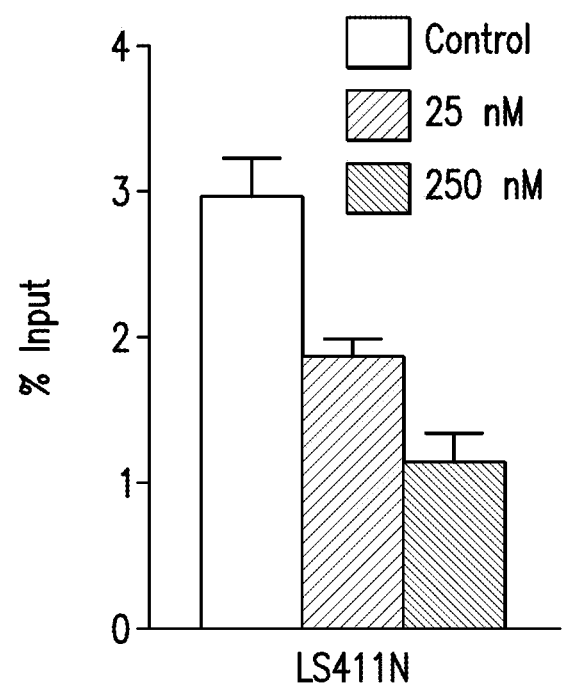

FIG. 15A-B shows that F5446 inhibits H3K9me3 at the FAS promoter region in human colon carcinoma cells.

Example 12: The SUV39H1-H3K9me3 Pathway Represses Effector Expression in T Cells Materials and Methods $CD3^+$ T cells were purified from spleens of C57BL/6 mice. The cells were stimulated in anti-CD3/CD28-coated plates for 2 days in the absence or presence of F5446 (50 nM). The resting, stimulated and treated T cells were then analyzed by ChIP (Chromatin Immunoprecipitation) with anti-H3K9me3 antibody and gene-specific PCR primers.

Results

Figure 16A:
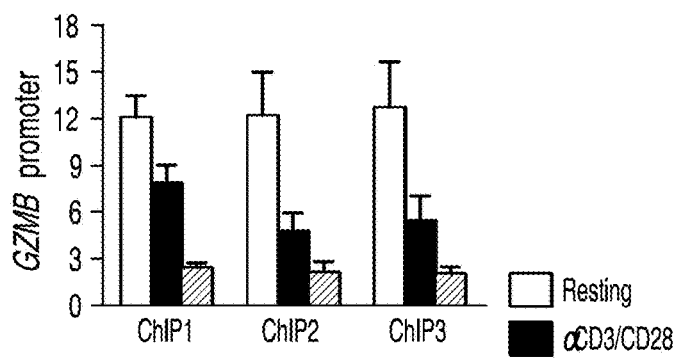
FIGS. 16A-16D are bar graphs showing H3K9me3 expression in four promoter regions (GZMB, FIG. 16A; FASLG, FIG. 16B; PRF1, FIG. 16C; and IFNG, FIG. 16D) of CD3+ T cells (white bar), activated CD3+ T cells (black bar), and activated CD3+ T cells treated with compound 1 (hatched bar).
Figure 16B:
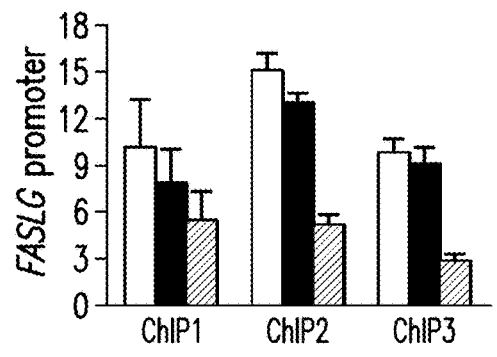
Figure 16C:
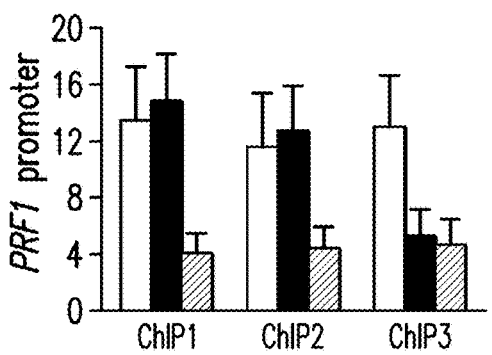
Figure 16D:
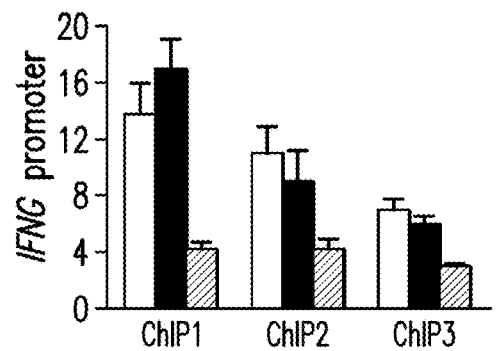
Figure 16E:
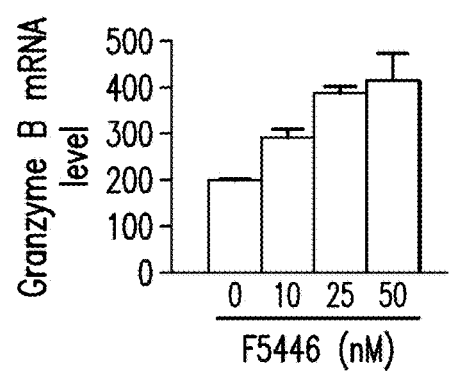
FIG. 16E-16H are bar graphs showing expression levels of four effectors (granzyme B, FIG. 16E; FasL, FIG. 16F; perforin, FIG. 16G; and IFNγ, FIG. 16H) in stimulated CD3+ T cells treated with increasing doses of compound 1.
Figure 16F:
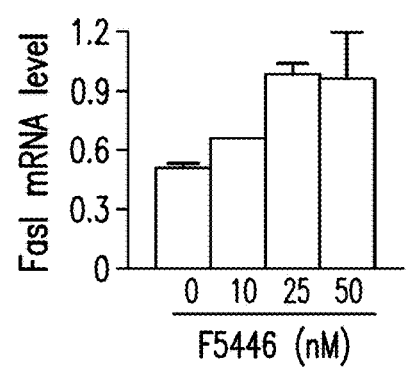
Figure 16G:
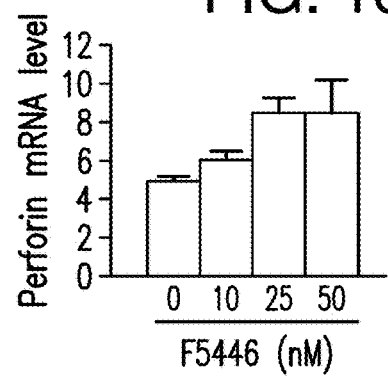
Figure 16H:
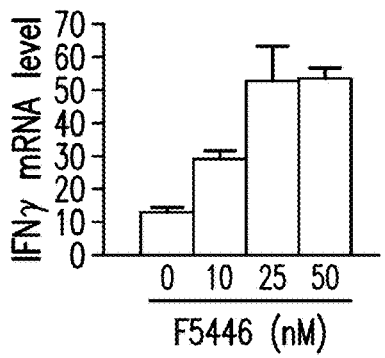
Figure 17A:
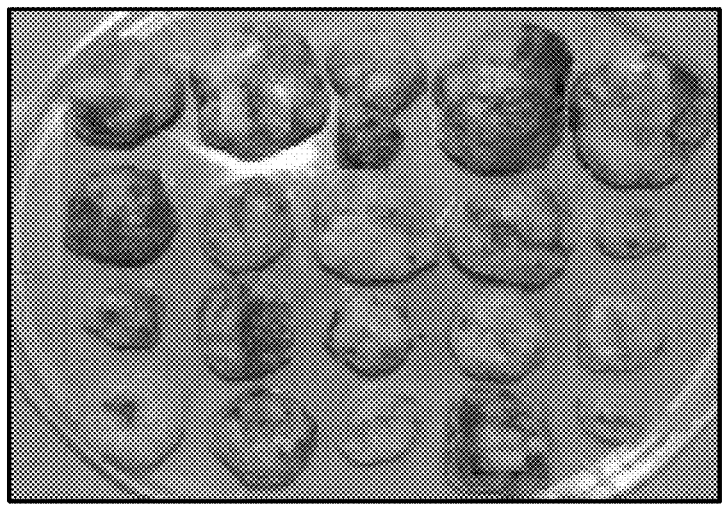
FIG. 17A shows tumor size in C$_{57}$BL/6 mice treated with compound 1.
Figure 17B:
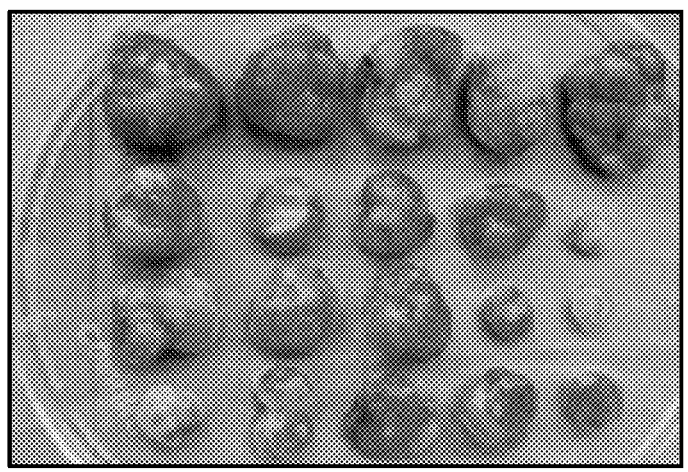
FIG. 17B shows tumor size in BALB/c mice treated with compound 1.
Figure 18A:
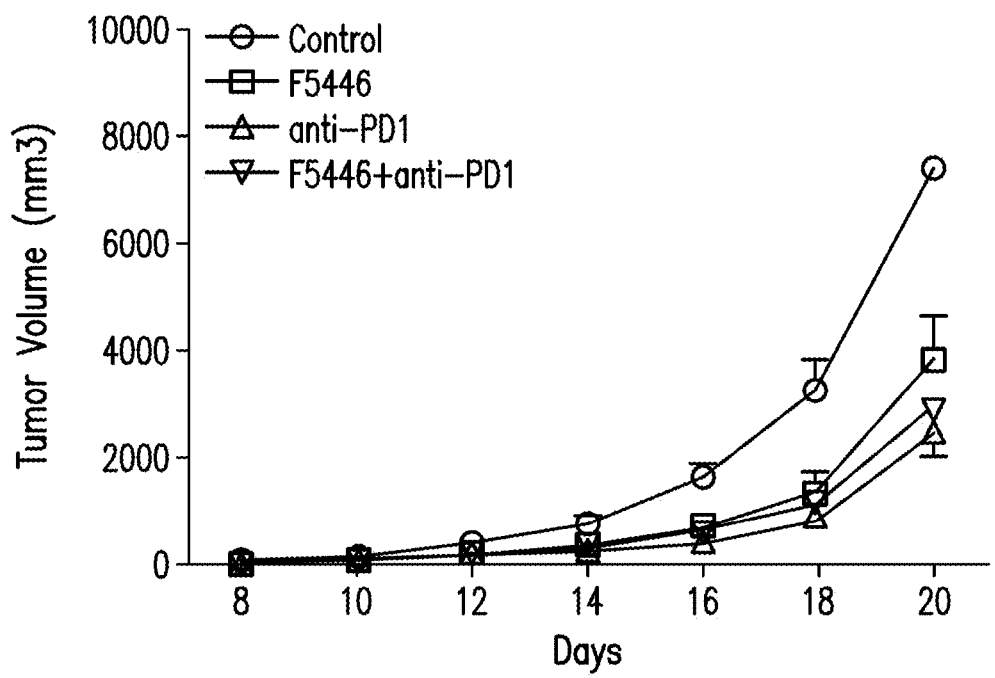
FIG. 18A is a line graph showing change in tumor volume (mm$^3$) over time (days) in tumor bearing C$_{57}$BL/6 mice either untreated (○), treated with compound 1 (□), treated with anti-PD1 (Δ), or treated with compound 1 and anti-PD1 (▼).
Figure 18B:
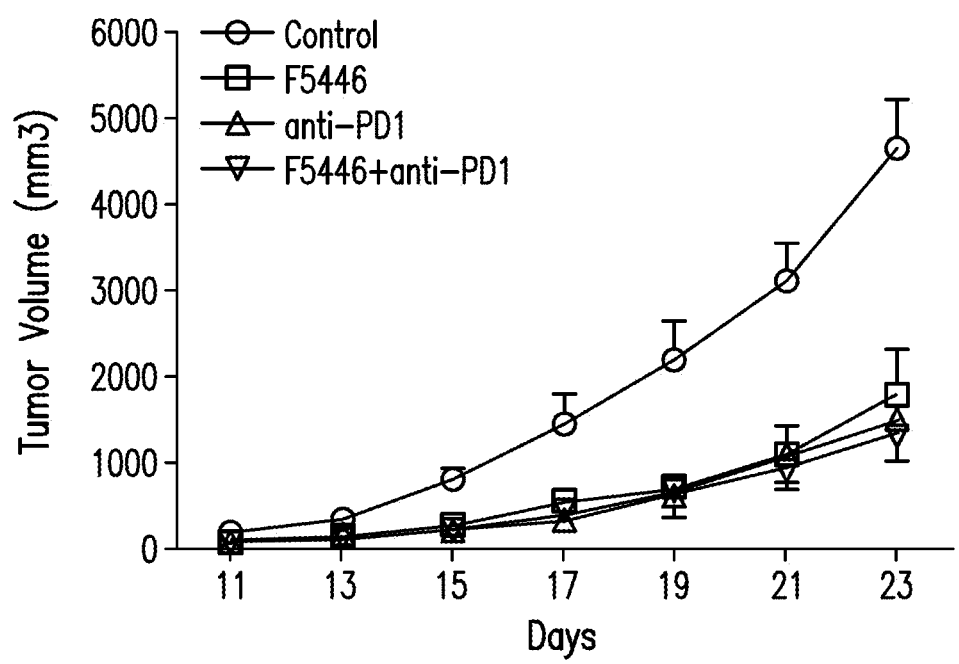
FIG. 18B is a line graph showing change in tumor volume (mm$^3$) over time (days) in tumor bearing BALB/c mice either untreated (○), treated with compound 1 (□), treated with anti-PD1 (△), or treated with compound 1 and anti-PD1 (▽).
Figure 19A:
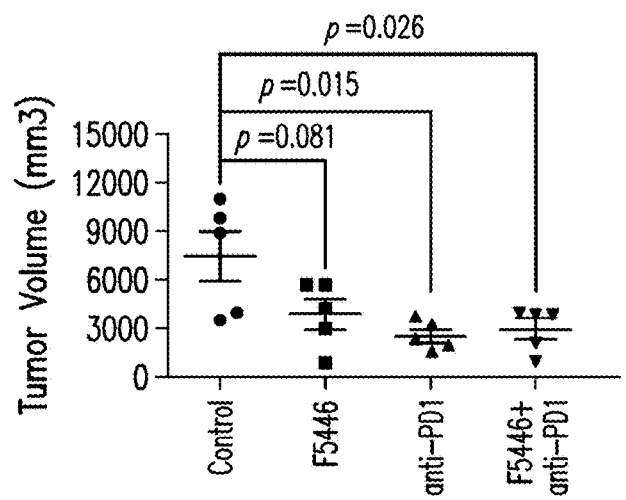
FIG. 19A is a graph showing tumor volume (mm³) in tumor bearing $C_{57}BL/6$ mice either untreated (●), treated with compound 1 (■), treated with anti-PD1 (▲), or treated with compound 1 and anti-PD1 (▼).
Figure 19B:
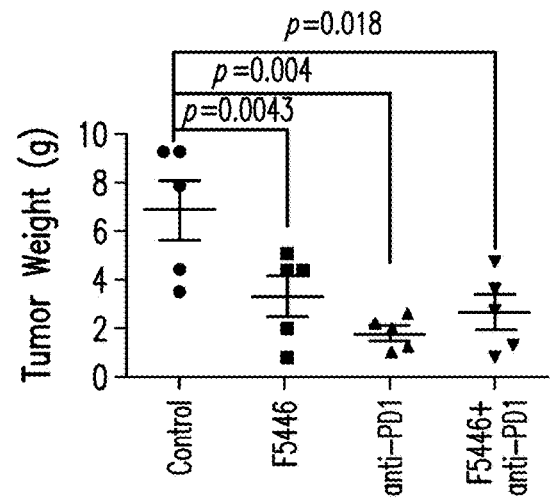
FIG. 19B is a graph showing tumor weight (g) in tumor bearing $C_{57}BL/6$ mice either untreated (D), treated with compound 1 (■), treated with anti-PD1 (▲), or treated with compound 1 and anti-PD1 (▼).
Figure 19C:
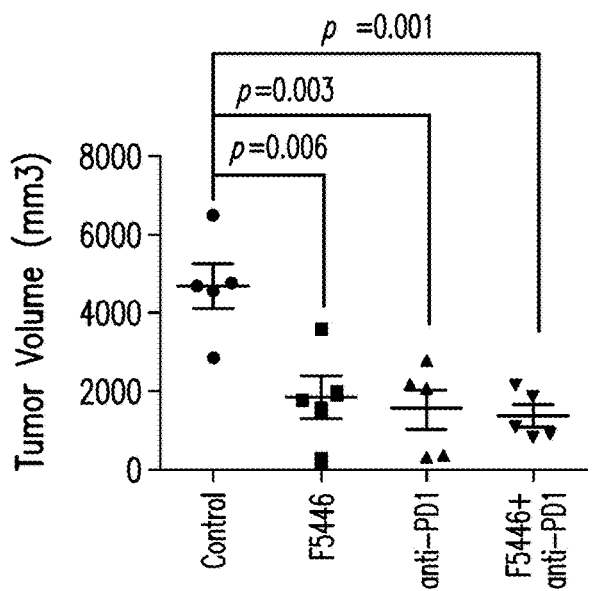
FIG. 19C is a graph showing tumor volume (mm³) in tumor bearing BALB/C mice either untreated (●), treated with compound 1 (■), treated with anti-PD1 (▲), or treated with compound 1 and anti-PD1 (▼).
Figure 19D:
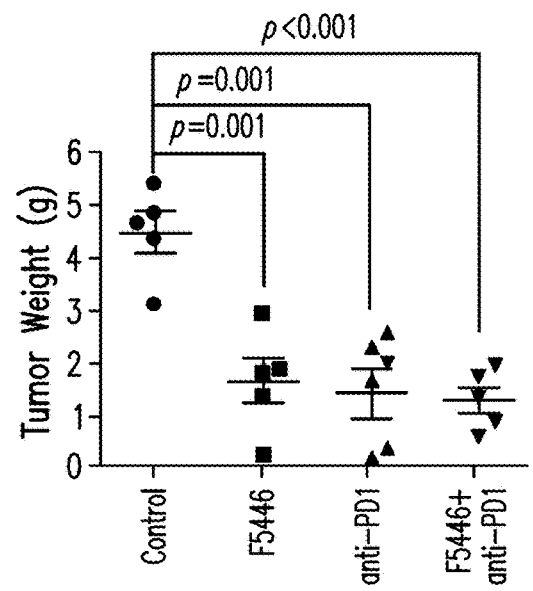
FIG. 19D is a graph showing tumor weight (g) in tumor bearing BALB/C mice either untreated (●), treated with compound 1 (■), treated with anti-PD1 (▲), or treated with compound 1 and anti-PD1 (▼).
Figure 21A:
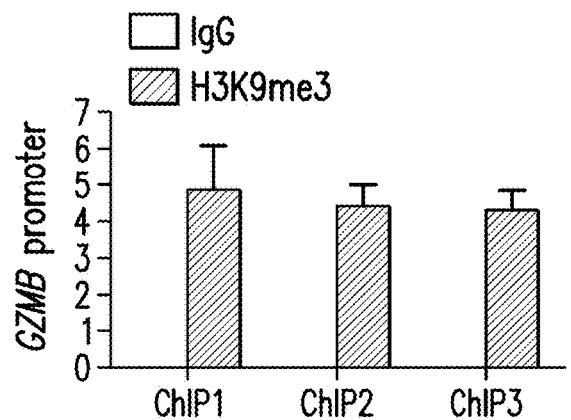
FIG. 21A-D are bar graphs showing expression of H3K9me3 in promoter regions of effector genes (GZMB, FIG. 21A; FASLG, FIG. 21B; PRF1, FIG. 21C, and IFNG, FIG. 20D) in CD8⁺ T cells.
Figure 21B:
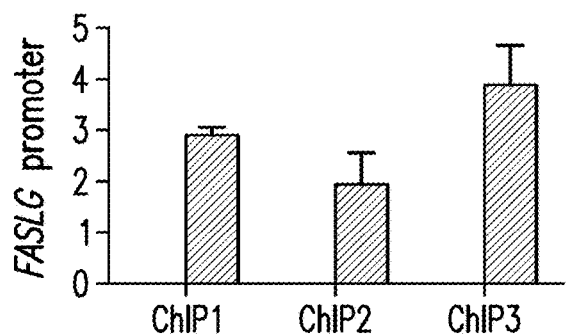
Figure 21C:
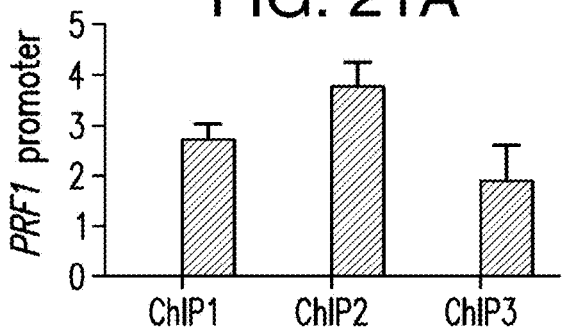
Figure 21D:
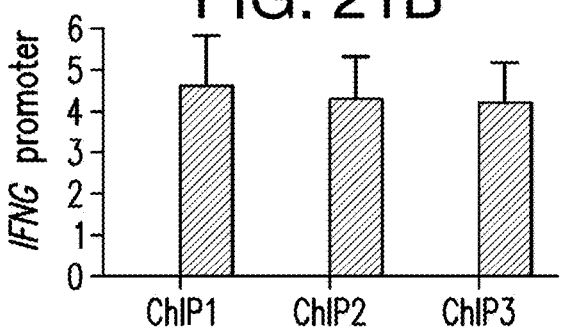
Figure 21E:
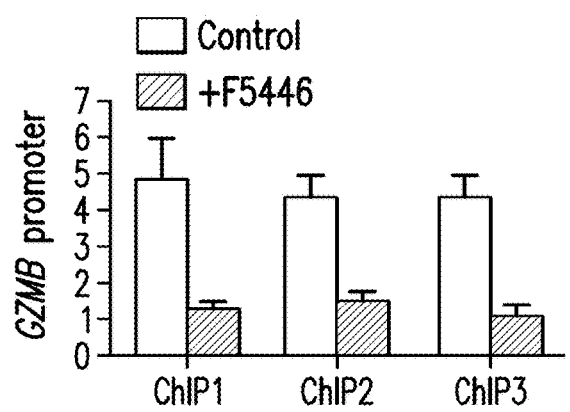
FIG. 21E-F are bar graphs that show expression of H3K9me3 in promoter regions of effector genes (GZMB, FIG. 21E; FASLG, FIG. 21F; PRF1, FIG. 21G, and IFNG, FIG. 20H) in CD8⁺ T cells treated with compound 1.
Figure 21F:
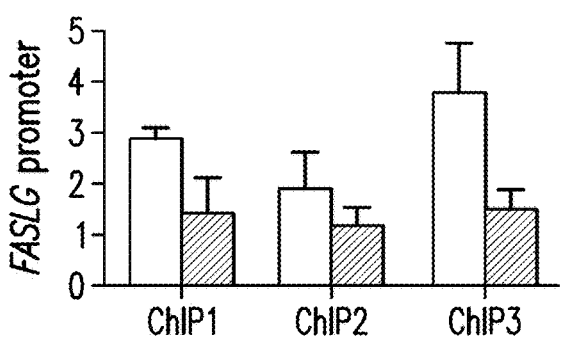
Figure 21G:
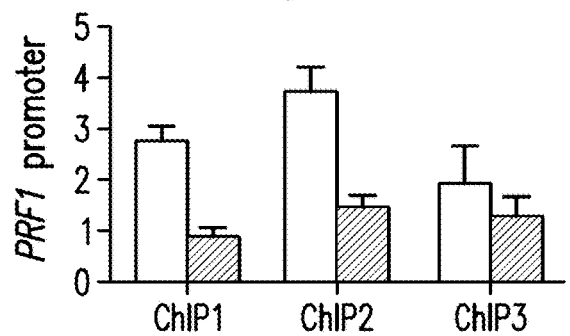
FIG. 21I-J are bar graphs that show expression of effector genes (granzyme B, FIG. 21I; perforin, FIG. 21J; FasL, FIG. 21K; and IFNγ, FIG. 21L) in CD8⁺ Tcells untreated (white bar) or treated with compound 1 (hatched bar).
Figure 21H:
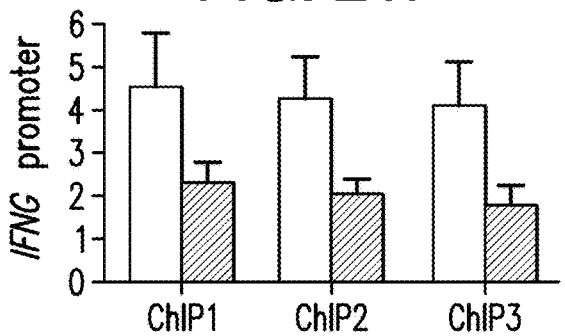

Stimulation of T cells decreased H3K9me3 levels at the promoter regions of GZMB and PRF1 (FIGS. 16A and 16C). FIG. 16A-16D shows that F5446 treatment reduced H3K9me3 levels in the promoter regions of GZMB (FIG. 16A), PRF1 (FIG. 16B), FASLG (FIG. 16C) and IFNG (FIG. 16D) in activated T cells.

FIG. 16E-16H shows varied levels of expression of GZMB (FIG. 16E), PRF1 (FIG. 16F), FASLG (FIG. 16G) and IFNG (FIG. 16H) in activated T cells treated with F5446. F5446 increased expression of all four effector genes in a dose-dependent manner.

Example 13: F5446 Increases T Cell Expression to Suppress Colon Carcinoma Growth In Vivo Materials and Methods Two different tumor cells were injected into two different strains of mice. MC38 cells ($1.5 \times 10^5$ cells/mouse) were injected to thirty C57BL/6 mice subcutaneously. CT26 cells ($2 \times 10^5$ cells/mouse) were injected to thirty BALB/c mice subcutaneously. Twenty mice from each strain with relatively similar sizes of tumors were randomized into four groups at day 8 after tumor cell injection. The four groups of tumor-bearing mice were treated with IgG/solvent (control), F5446 (10 mg/kg), anti-PD-1 mAb (200 mg/mouse), and F5446+anti-PD-1 mAb, respectively, every two days for 14 days.

Results

Tumor bearing mice were treated with IgG, F5446, anti-PD-1 mAb, and F5446+anti-PD-1. Both F5446 and anti-PD-1 treatments suppressed the established tumor growth in a time-dependent manner (FIGS. 17A-17B and 18A-18B). Both F5446 and anti-PD-1 treatments significantly reduced tumor growth as measured by tumor size and tumor weight (FIG. 19A-19D). However, F5446 and anti-PD-1 did not show additive or synergistic effects. To determine whether inhibition of SUV39H1 increases T cell effector expression in vivo, tumor tissues were analyzed for the expression of the four effector genes. qPCR analysis revealed that F5446 treatment significantly increased the expression levels of granzymeB (FIGS. 20A and 20E), perforin (FIGS. 20B and 20F), FasL (FIGS. 20C and 20G) and IFNγ (FIGS. 20D and 20H).

Example 14: SUV39H1-H3K9me3 Pathway Represses T Cell Effector Expression in Tumor Infiltrating CTLs In Vivo Materials and Methods CD8+ CTLs were isolated from tumor tissues of the control and the F5446-treated groups of CT26 tumor bearing mice (from Example 13). ChIP analysis of H3K9me3 level in the promoter regions of GZMB, PRF1, FASLG and IFNG was performed. Further a qPCR analysis was performed to determine the expression levels of all four promoter regions.

Results

CD8+ CTLs were isolated from tumor tissues of the control and the F5446-treated groups. ChIP analysis of H3K9me3 level in the promoter regions of GZMB (FIG. 21A), PRF1 (FIG. 21B), FASLG (FIG. 21C) and IFNG (FIG. 21D) indicated that H3K9me3 is enriched in the promoter regions of these four T cell effector genes. Treatment with F5446 decreased H3K9me3 levels in the promoter regions of all 4 effector genes in the tumor-infiltrating CTLs (FIG. 21E-21H). qPCR analysis determined that the expression levels of granzymeB, perforin, FasL and IFNγ were significantly increased by F5446 treatment (FIG. 21I-21L). Taken together, these data indicate that F5446 targets SUV39H1 and suppresses colon tumor growth at least in part through inhibiting H3K9me3 to increase the expression level of granzyme B, perforin, Fasl and IFNγ in tumor-infiltrating CTLs in the tumor microenvironment.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

What is claimed is:

1. A compound defined according to formula (I) as follows:

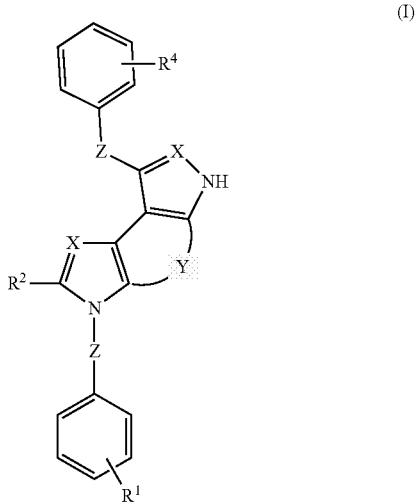

where:
$R^1$ and $R^4$ are each independently selected from —H, halogen, —$NO_2$, —O-alkyl, —N-alkyl, —S-alkyl, —$NH_2$, —COO—($C_1$-$C_{16}$)-alkyl, or $CONR^5R^6$,
$R^2$ is selected from —H, halogen, —O-alkyl, —N-alkyl, —S-alkyl, —($C_1$-$C_{33}$)-alkyl, -heteroaryl, -aryl, -acyl, or —COO—($C_1$-$C_{16}$)-alkyl,
X is —CH or —N,
Z is selected from —$SO_2$, —SO, —($C_1$-$C_{33}$) alkyl, —($C_1$-$C_{33}$) alkenyl, C(O)OCH2, —O, or S—S,
Y is selected from —C═O—C═O, —($C_1$-$C_4$)-alkyl, —CH═CH—, —O, —S, or —$CH_2R^7CH_2$,
$R^5$ and $R^6$ are each independently selected from —H, —($C_1$-$C_4$)-alkyl, —($C_1$-$C_3$)-alkoxy-($C_2$-$C_4$)-alkyl, or OH—($C_2$-$C_4$)-alkyl,
$R^7$ is —S, or —O, and n is 1 to 33.

2. The compound of claim 1, wherein:
$R^1$ and $R^4$ are each independently selected from —H, —F, —Cl, —Br, —I, —$NO_2$, —O—($C_1$-$C_{20}$)-alkyl, —N—($C_1$-$C_{20}$)-alkyl, —S—($C_1$-$C_{20}$)-alkyl, —$NH_2$, —COO—($C_1$-$C_{16}$)-alkyl, or —$CONR^5R^6$, where $R^5$ and $R^6$ are each independently selected from —H, —($C_1$-$C_4$)-alkyl, —($C_1$-$C_3$)-alkoxy-($C_2$-$C_4$)-alkyl, or —OH—($C_2$-$C_4$)-alkyl, $R^2$ is selected from —H, —F, —Cl, —Br, —I, —O—($C_1$-$C_{20}$)-alkyl, —N—($C_1$-$C_{20}$)-alkyl, —S—($C_1$-$C_{20}$)-alkyl, —($C_1$-$C_{20}$)-alkyl, —($C_3$-$C_{20}$)-heteroaryl, —($C_6$-$C_{20}$)-aryl, acyl, or —COO—($C_1$-$C_{12}$)-alkyl, X is —CH or —N, Z is selected from —$SO_2$, —SO, —($C_1$-$C_{20}$) alkyl, —($C_1$-$C_{20}$) alkenyl, C(O)OCH2, —O, — or —SS, where n is 1 to 20, and Y is selected from —C=O—C=O, —($C_1$-$C_3$)-alkyl, —CH=CH—, [—N], —O, —S, —$CH_2SCH_2$, —$CH_2OCH_2$, or —$CH_2NCH_2$.

3. The compound of claim 1, wherein:

$R^1$ and $R^4$ are each independently be selected from —H, —F, —Cl, —$NO_2$, —O—($C_1$-$C_{12}$)-alkyl, —N—($C_1$-$C_{12}$)-alkyl, —S—($C_1$-$C_{12}$)-alkyl, —$NH_2$, or —COO—($C_1$-$C_{12}$)-alkyl, $R^2$ is selected from —H, —F, —Cl, —Br, —I, —O—($C_1$-$C_{12}$)-alkyl, —N—($C_1$-$C_{12}$)-alkyl, —S—($C_1$-$C_{12}$)-alkyl, —($C_1$-$C_{12}$)-alkyl, —($C_3$-$C_{14}$)-heteroaryl, —($C_6$-$C_{14}$)-aryl, $R_y$—CO— where $R_y$ is a —($C_1$-$C_{12}$)-alkyl, —($C_3$-$C_6$)-cycloalkyl, or phenyl, or —COO—($C_1$-$C_4$)-alkyl, X is —CH or —N, Z is selected from —$SO_2$, —SO, —($C_1$-$C_{12}$) alkyl, —($C_1$-$C_{12}$) alkenyl, C(O)OCH2, or —O, where n is 1 to 12, and Y is selected from —C=O—C=O, —($C_1$-$C_2$)-alkyl, or —CH=CH—.

4. The compound of claim 1, having the following structure:

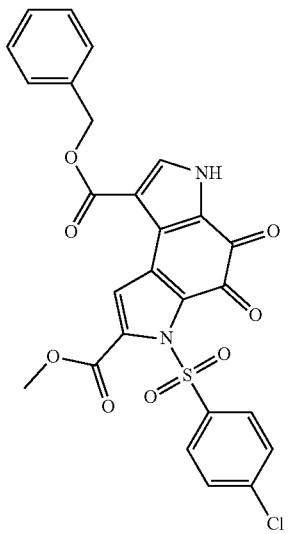 [SMILES: COC(=O)c1cc2c(n1S(=O)(=O)c1ccc(Cl)cc1)C(=O)C(=O)c1[nH]cc(C(=O)OCc3ccccc3)c1-2]

5. A pharmaceutical composition, comprising:
the compound of claim 1,
a hydrate or pharmaceutically acceptable salt, or
any combination thereof.

6. The pharmaceutical composition of claim 5, wherein the compound is present in an amount effective to inhibit SUV39H1 methyltransferase activity and induce or increase Fas receptor expression on cancer cells.

7. The pharmaceutical composition of claim 5, further comprising a pharmaceutically acceptable excipient.

8. The pharmaceutical composition of claim 5, wherein the composition is formulated for parenteral administration.

9. The pharmaceutical composition of claim 8, wherein the composition is formulated for parenteral administration selected from the group consisting of intramuscular, intraperitoneal, intravitreal, intravenous, and subcutaneous administration.

10. The pharmaceutical composition of claim 5, wherein the composition is formulated for enteral administration.

11. The pharmaceutical composition of claim 5, wherein the composition is formulated as an extended release formulation.

12. The pharmaceutical composition of claim 5, further comprising an effective amount of an anti-PD-1 or anti-PD-L1 immunotherapy.

13. The pharmaceutical composition of claim 12, wherein the compound is 1-Benzyl 7-methyl 6-(4-chlorobenzenesulfonyl)-4,5-dioxo-3H,4H,5H,6H-pyrrolo[3,2-e]indole-1,7-dicarboxylate.

14. The pharmaceutical composition of claim 5, further comprising an effective amount of a chemotherapeutic agent.

15. The pharmaceutical composition of claim 5, wherein the composition comprises the compound having the following structure:

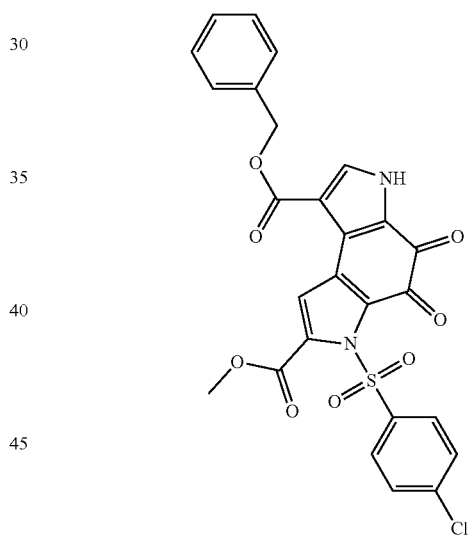

or an enantiomer, hydrate, pharmaceutically acceptable salt, stereoisomer, tautomer, or derivative thereof.

16. A method of treating cancer in a subject having cancer, comprising:
administering to the subject an effective amount of the pharmaceutical composition of claim 5 to increase apoptosis of cancer or tumor cells in the subject.

17. The method of claim 16, wherein the cancer is colorectal cancer or pancreatic cancer.

18. The method of claim 16, further comprising administering to the subject an effective amount of a chemotherapeutic agent or an anti-PD-1/PD-L1 immunotherapy in combination or alternation with the pharmaceutical composition of claim 5.

* * * * *

UNITED STATES PATENT AND TRADEMARK OFFICE
CERTIFICATE OF CORRECTION

PATENT NO. : 10,577,371 B2
APPLICATION NO. : 16/134306
DATED : March 3, 2020
INVENTOR(S) : I. Lebedyeva et al.

It is certified that error appears in the above-identified patent and that said Letters Patent is hereby corrected as shown below:

On the Title Page

Item (72) In the Inventors:
Please add as fourth inventor Thomas Albers (Augusta, GA, US)

Signed and Sealed this
Sixteenth Day of July, 2024

Katherine Kelly Vidal
*Director of the United States Patent and Trademark Office*